(12) United States Patent
Stevenson et al.

(10) Patent No.: US 7,751,903 B2
(45) Date of Patent: *Jul. 6, 2010

(54) FREQUENCY SELECTIVE PASSIVE COMPONENT NETWORKS FOR IMPLANTABLE LEADS OF ACTIVE IMPLANTABLE MEDICAL DEVICES UTILIZING AN ENERGY DISSIPATING SURFACE

(75) Inventors: Robert A. Stevenson, Canyon Country, CA (US); Warren S. Dabney, Orchard Park, NY (US); Christine A. Frysz, Orchard Park, NY (US); Buehl E. Truex, Glendora, CA (US); Henry R. Halperin, Pikesville, MD (US); Albert C. Lardo, Baltimore, MD (US)

(73) Assignee: Greatbatch Ltd., Clarence, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/489,921

(22) Filed: Jun. 23, 2009

(65) Prior Publication Data
US 2010/0023000 A1    Jan. 28, 2010

Related U.S. Application Data

(63) Continuation-in-part of application No. 10/123,534, filed on Apr. 15, 2002.

(60) Provisional application No. 60/283,725, filed on Apr. 13, 2001.

(51) Int. Cl.
*A61N 1/08* (2006.01)

(52) U.S. Cl. .......................................... 607/63; 607/60

(58) Field of Classification Search .................. None
See application file for complete search history.

(56) References Cited

U.S. PATENT DOCUMENTS

| 4,188,598 | A |   | 2/1980 | Hunt |
| 4,320,763 | A |   | 3/1982 | Money |
| 4,424,551 | A |   | 1/1984 | Stevenson et al. |
| 5,197,468 | A |   | 3/1993 | Proctor et al. |
| 5,217,010 | A |   | 6/1993 | Tsitlik et al. |
| 5,333,095 | A |   | 7/1994 | Stevenson et al. |
| 5,334,045 | A | * | 8/1994 | Cappa et al. ................ 439/506 |
| 5,591,218 | A |   | 1/1997 | Jacobson |
| 5,735,887 | A | * | 4/1998 | Barreras et al. .............. 607/60 |

(Continued)

OTHER PUBLICATIONS

Roger Christoph Luchinger, "Safety Aspects of Cardiac Pacemakers in Magnetic Resonance Imaging," a dissertation submitted to the Swiss Federal Institute of Technology Zurich, 2002, Zurich.

(Continued)

*Primary Examiner*—Carl H. Layno
*Assistant Examiner*—Jon-Eric C. Morales
(74) *Attorney, Agent, or Firm*—Kelly Lowry & Kelley, LLP

(57) ABSTRACT

Decoupling circuits are provided which transfer energy induced from an MRI pulsed RF field to an energy dissipating surface. This is accomplished through broadband filtering or by resonant filtering. In a passive component network for an implantable leadwire of an active implantable medical device, a frequency selective energy diversion circuit is provided for diverting high-frequency energy away from a leadwire electrode to a point or an area spaced from the electrode, for dissipation of high-frequency energy.

61 Claims, 35 Drawing Sheets

U.S. PATENT DOCUMENTS

| | | | |
|---|---|---|---|
| 5,772,693 A * | 6/1998 | Brownlee | 607/123 |
| 5,824,029 A | 10/1998 | Weijand et al. | |
| 6,099,524 A | 8/2000 | Lipson et al. | |
| 6,370,427 B1 * | 4/2002 | Alt et al. | 607/4 |
| 6,759,388 B1 | 7/2004 | Marchant et al. | |
| 6,765,779 B2 | 7/2004 | Stevenson et al. | |
| 6,871,091 B2 | 3/2005 | Wilkinson et al. | |
| 6,898,454 B2 | 5/2005 | Atalar et al. | |
| 6,901,292 B2 | 5/2005 | Hrdlicka et al. | |
| 6,944,489 B2 | 9/2005 | Zeijlemaker et al. | |
| 6,985,775 B2 | 1/2006 | Reinke et al. | |
| 7,155,271 B2 | 12/2006 | Halperin et al. | |
| 7,174,219 B2 | 2/2007 | Wahlstrand et al. | |
| 7,276,474 B2 | 10/2007 | Marchant et al. | |
| 7,319,905 B1 * | 1/2008 | Morgan et al. | 607/129 |
| 7,363,090 B2 | 4/2008 | Halperin | |
| 2001/0031995 A1 * | 10/2001 | Molin | 607/20 |
| 2001/0051787 A1 * | 12/2001 | Haller et al. | 604/66 |
| 2003/0050557 A1 | 3/2003 | Susil | |
| 2005/0070972 A1 | 3/2005 | Wahlstrand et al. | |
| 2005/0222658 A1 | 10/2005 | Hoegh et al. | |
| 2006/0009819 A1 * | 1/2006 | Przybyszewski | 607/63 |
| 2007/0112398 A1 | 5/2007 | Stevenson | |
| 2007/0168005 A1 | 7/2007 | Gray | |
| 2007/0288058 A1 | 12/2007 | Halperin et al. | |
| 2008/0049376 A1 | 2/2008 | Stevenson | |
| 2008/0071313 A1 | 3/2008 | Stevenson | |
| 2008/0116997 A1 | 5/2008 | Dabney | |
| 2008/0132987 A1 | 6/2008 | Westlund | |
| 2008/0161886 A1 | 7/2008 | Stevenson et al. | |

OTHER PUBLICATIONS

C. Gabriel, S. Gabriel and E. Corthout, "I. Dielectric Properties of Biological Tissues: Literature Survey," 1996, IOP Publishing Ltd.

S. Gabriel, R.W. Lau and C. Gabriel, "II. Dielectric Properties of Biological Tissues: Measurements and the Freuency Range 0 Hz to 20 GHz,"Phys. Med. Biol. 41, 1996, pp. 2251-2269, IOP Publishing Ltd.

S. Gabriel, R.W. Lau and C. Gabriel, "III. The Dielectric Properties of Biological Tissues: Parametric Models for the Dielectric Spectrum of Tissues," Phys. Med. Biol. 41, 1996, pp. 2271-2293, IOP Publishing Ltd.

Constantine A. Balinis, "Advanced Engineering Electromagnetics," 1989, John Wiley & Sons.

Robert C. Susil, Henry R. Halperin, Christopher J. Yeung, Albert C. Lardo and Ergin Atalar, "Multifunctional Interventional Devices for MRI: A Combined Electrophysiology/MRI Catheter," Magnetic Resonance in Medicine, 47: 594-600, 2002.

Mauritis K. Konings, Lambertus W. Bartels, Henk F.M. Smits and Chris J.G. Bakker, "Heating Around Intravascular Guidewires by Resonating RF Waves," Journal of Magnetic Resonance Imaging, 12:79-85, 2000.

Michael J. Weiner, Wilson Greatbatch, Patrick R. Connelly, U.S. Appl. No. 60/269,817, filed Feb. 20, 2001, entitled "Electromagnetic Interference Immune Cardiac Assist System."

Bruce L. Wilkoff M.D., "ICD Extraction Infected/Redundant Leads—Everyday Clinical Practice," Cleveland Clinic, ICD Lead Extraction, Every Day Practice.

Frank G. Shellock, Ph.D., "MRI Issues for Neuromodulation Devices," Institute for Magnetic Resonance Safety, Education, and Research (IMRSER).

* cited by examiner

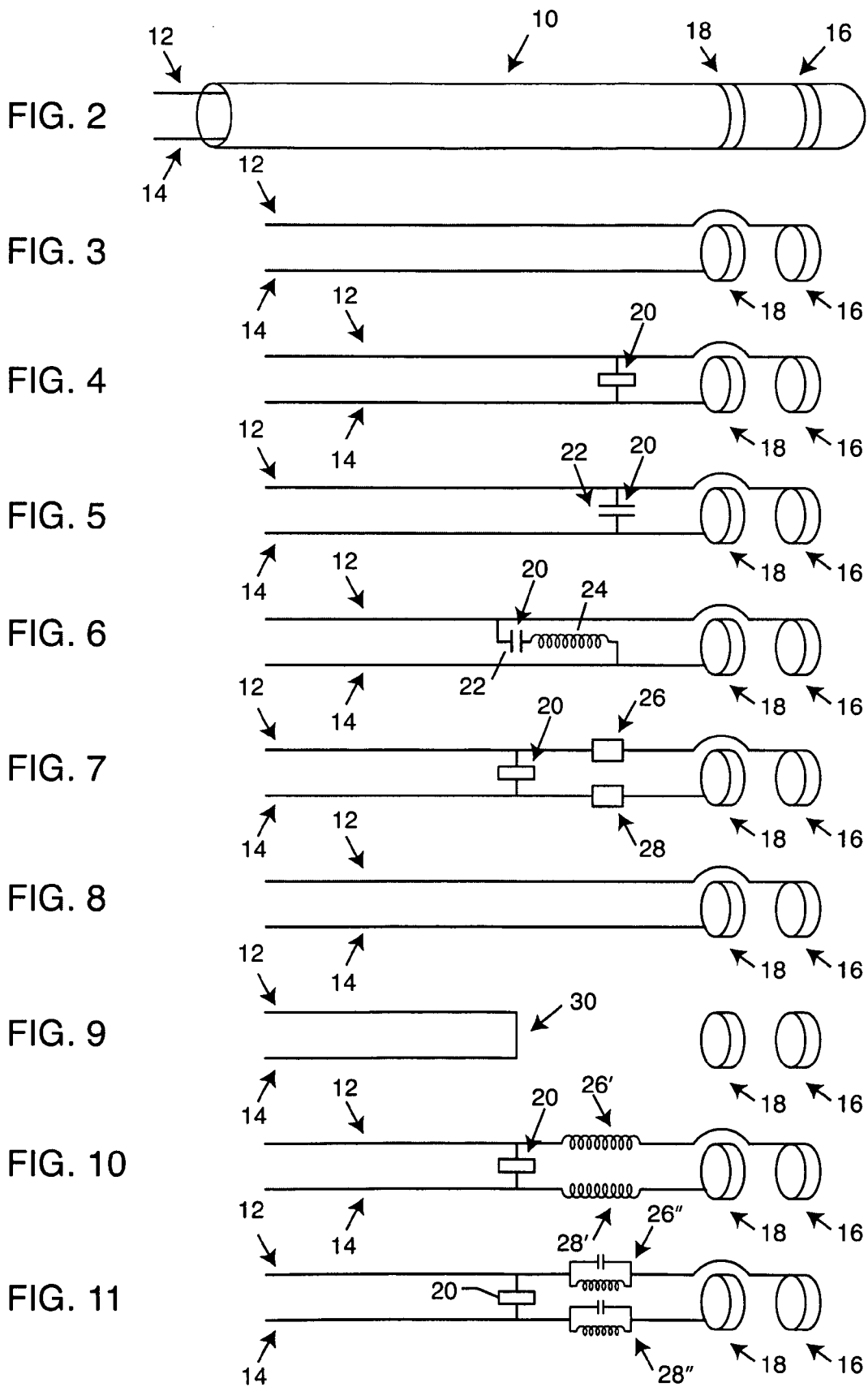

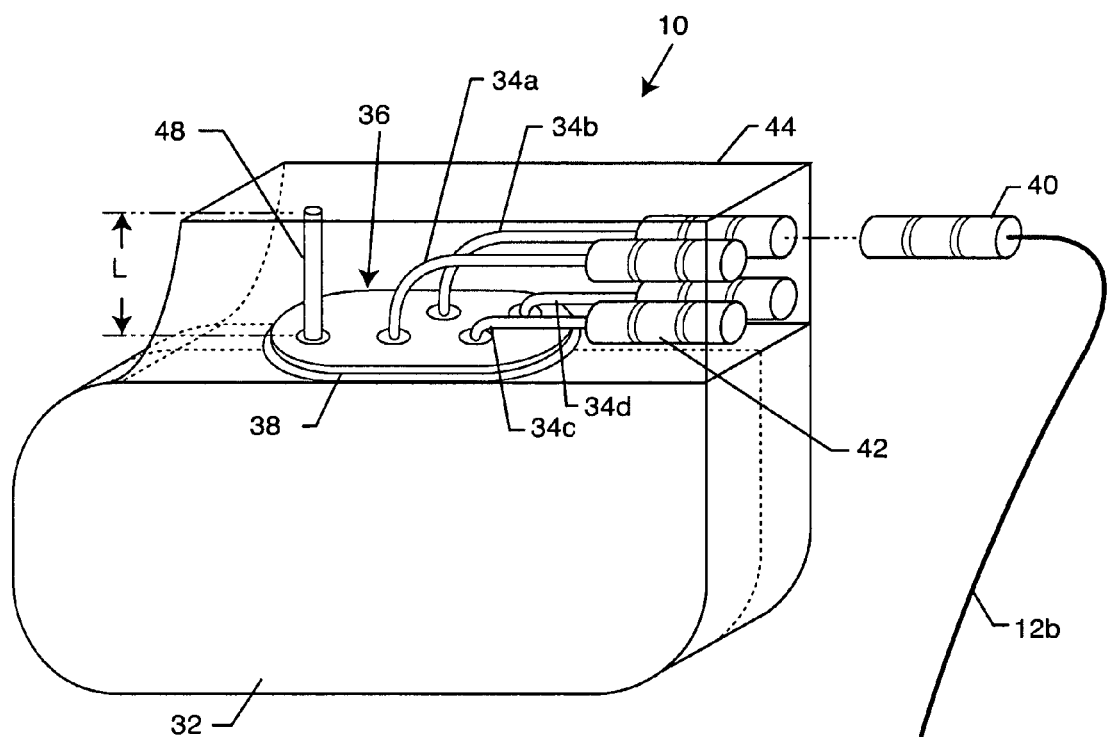
FIG. 12
PRIOR ART
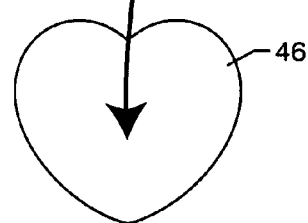

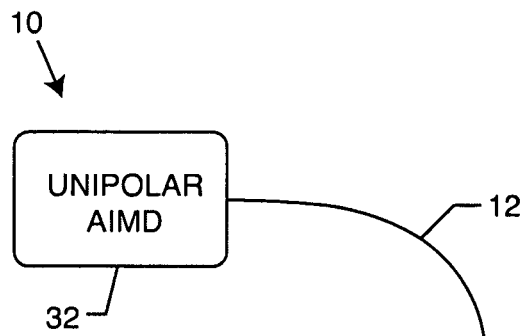
FIG. 13
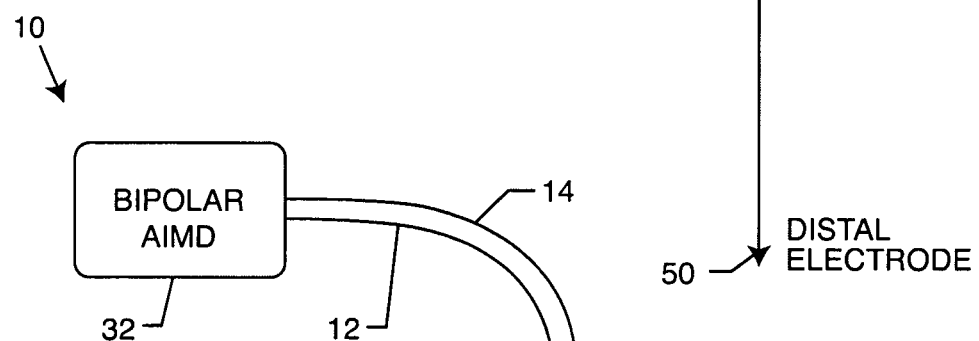
FIG. 14
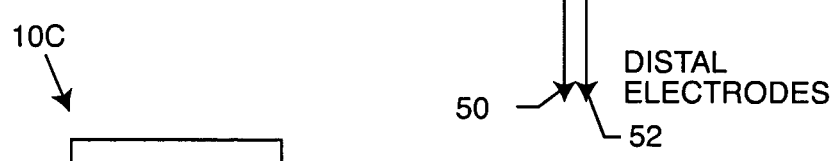
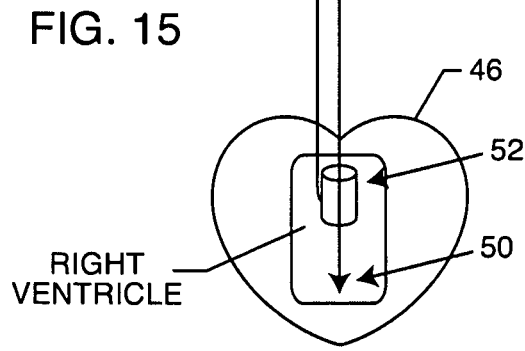
FIG. 15

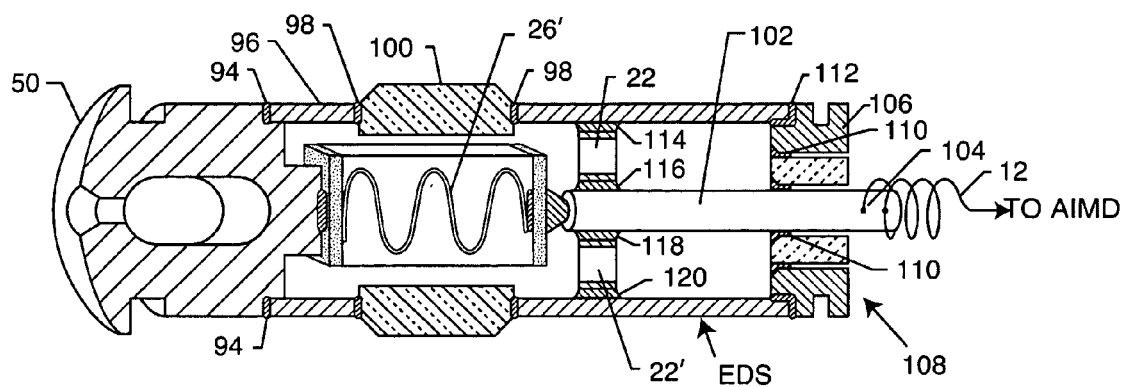
FIG. 30
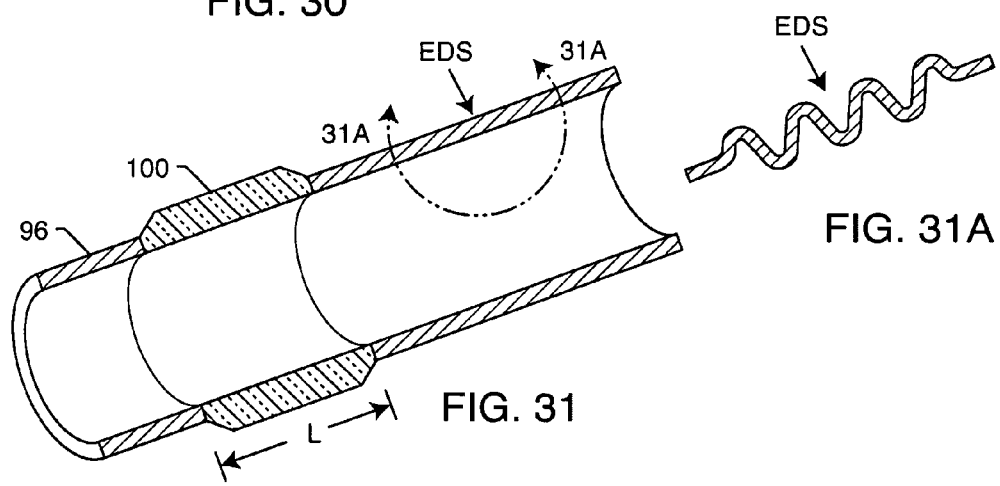
FIG. 31A
FIG. 31
FIG. 32
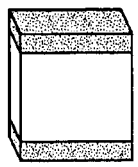
FIG. 33A
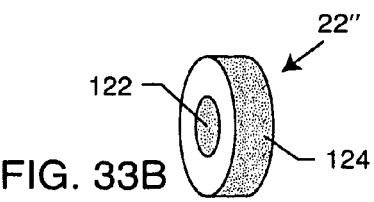
FIG. 33B WHERE  C = CAPACITANCE IN FARADS
L = INDUCTANCE IN HENRYS
R = RESISTANCE (INCLUDES RESISTANCE OF INDUCTOR, HOOK-UP WIRE & CAPACITOR EQUILIVANT SERIES RESISTANCE (ESR)

RESONANT FREQUENCY  = $F_r$

WHERE  $F_R = \dfrac{1}{2\pi\sqrt{LC}}$

WHERE $F_R$ IS IN HERTZ

FREQUENCY SELECTIVE PASSIVE COMPONENT NETWORKS FOR IMPLANTABLE LEADS OF ACTIVE IMPLANTABLE MEDICAL DEVICES UTILIZING AN ENERGY DISSIPATING SURFACE

BACKGROUND OF THE INVENTION

This invention generally relates to the problem of energy induced into implanted leads during medical diagnostic procedures such as magnetic resonant imaging (MRI). Specifically, the radio frequency (RF) pulsed field of MRI can couple to an implanted lead in such a way that electromagnetic forces (EMFs) are induced in the lead. The amount of energy that is induced is related to a number of complex factors, but in general, is dependent upon the local electric field that is tangent to lead and the integral of the tangential electric field strength along the lead. In certain situations, these EMFs can cause currents to flow into distal electrodes or in the electrode interface with body tissue. It has been documented that when this current becomes excessive, that overheating of said electrode or overheating of the associated interface with body tissue can occur. There have been cases of damage to such body tissue which has resulted in loss of capture of cardiac pacemaking pulses, tissue damage, severe enough to result in brain damage or multiple amputations, and the like. The present invention relates generally to methods of redirecting said energy to other locations other than a distal tip electrode-to-tissue interface. The redirection of this RF energy is generally done by use of frequency selective devices, such as inductors, capacitors and filtered networks. In general, this is accomplished through frequency selective low pass filters or series resonant LC trap filters wherein the RF energy can be redirected to another surface or is converted to heat. These implantable lead systems are generally associated with active implantable medical devices (AIMDs), such as cardiac pacemakers, cardioverter defibrillators, neurostimulators and the like. Implantable leads can also be associated with external devices, such as external pacemakers, externally worn neurostimulators (such as pain control spinal cord stimulators) and the like.

Compatibility of cardiac pacemakers, implantable defibrillators and other types of active implantable medical devices with magnetic resonance imaging (MRI) and other types of hospital diagnostic equipment has become a major issue. If one goes to the websites of the major cardiac pacemaker manufacturers in the United States, which include St. Jude Medical, Medtronic and Boston Scientific (formerly Guidant), one will see that the use of MRI is generally contra-indicated with pacemakers and implantable defibrillators. See also:

(1) Safety Aspects of Cardiac Pacemakers in Magnetic Resonance Imaging", a dissertation submitted to the Swiss Federal Institute of Technology Zurich presented by Roger Christoph Luchinger, Zurich 2002;
(2) "1. Dielectric Properties of Biological Tissues: Literature Survey", by C. Gabriel, S. Gabriel and E. Cortout;
(3) "II. Dielectric Properties of Biological Tissues: Measurements and the Frequency Range 0 Hz to 20 GHz", by S. Gabriel, R. W. Lau and C. Gabriel;
(4) "III. Dielectric Properties of Biological Tissues: Parametric Models for the Dielectric Spectrum of Tissues", by S. Gabriel, R. W. Lau and C. Gabriel; and
(5) "Advanced Engineering Electromagnetics, C. A. Balanis, Wiley, 1989;
(6) Systems and Methods for Magnetic-Resonance-Guided Interventional Procedures, Patent Application Publication US 2003/0050557, Susil and Halperin et. al, published Mar. 13, 2003;
(7) Multifunctional Interventional Devices for MRI: A Combined Electrophysiology/MRI Catheter, by, Robert C. Susil, Henry R. Halperin, Christopher J. Yeung, Albert C. Lardo and Ergin Atalar, MRI in Medicine, 2002; and
(8) Multifunctional Interventional Devices for Use in MRI, U.S. Patent Application Ser. No. 60/283,725, filed Apr. 13, 2001.

The contents of the foregoing are all incorporated herein by reference.

However, an extensive review of the literature indicates that MRI is indeed often used with pacemaker, neurostimulator and other active implantable medical device (AIMD) patients. The safety and feasibility of MRI in patients with cardiac pacemakers is an issue of gaining significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker patients means that pacemaker and implantable cardioverter defibrillator (ICD) wearers are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF Pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that would be found in implanted leadwires or devices. For example, for magnetic resonance imaging devices operating at the same magnetic field strength and also at the same SAR level, considerable variations have been found relative to heating of implanted leadwires. It is speculated that SAR level alone is not a good predictor of whether or not an implanted device or its associated leadwire system will overheat.

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 5 Tesla. At the recent International Society for Magnetic Resonance in Medicine (ISMRM), which was held on 5 and 6 Nov. 2005, it was reported that certain research systems are going up as high as 11.7 Tesla and will be ready sometime in 2009. This is over 100,000 times the magnetic field strength of the earth. A static magnetic field can induce powerful mechanical forces and torque on any magnetic materials implanted within the patient. This would include certain components within the cardiac pacemaker itself and or leadwire systems. It is not likely (other than sudden system shut down) that the static MRI magnetic field can induce currents into the pacemaker leadwire system and hence into the pacemaker itself. It is a basic principle of physics that a magnetic field must either be time-varying as it cuts across the conductor, or the conductor itself must move within the magnetic field for currents to be induced.

The second type of field produced by magnetic resonance imaging is the pulsed RF field which is generated by the body coil or head coil. This is used to change the energy state of the protons and elicit MRI signals from tissue. The RF field is homogeneous in the central region and has two main components: (1) the magnetic field is circularly polarized in the actual plane; and (2) the electric field is related to the magnetic field by Maxwell's equations. In general, the RF field is switched on and off during measurements and usually has a frequency of 21 MHz to 64 MHz to 128 MHz depending upon the static magnetic field strength. The frequency of the RF pulse varies by the Lamor equation with the field strength of the main static field where: RF PULSED FREQUENCY in MHz=(42.56) (STATIC FIELD STRENGTH IN TESLA).

The third type of electromagnetic field is the time-varying magnetic gradient fields designated $B_x$, $B_y$, $B_z$, which are used for spatial localization. These change their strength along different orientations and operating frequencies on the order of 1 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. The gradient field is not considered by many researchers to create any other adverse effects.

It is instructive to note how voltages and electro-magnetic interference (EMI) are induced into an implanted leadwire system. At very low frequency (VLF), voltages are induced at the input to the cardiac pacemaker as currents circulate throughout the patient's body and create voltage drops. Because of the vector displacement between the pacemaker housing and, for example, the tip electrode, voltage drop across the resistance of body tissues may be sensed due to Ohms Law and the circulating current of the RF signal. At higher frequencies, the implanted leadwire systems actually act as antennas where voltages (EMFs) are induced along their length. These antennas are not very efficient due to the damping effects of body tissue; however, this can often be offset by extremely high power fields (such as MRI pulsed fields) and/or body resonances. At very high frequencies (such as cellular telephone frequencies), EMI signals are induced only into the first area of the leadwire system (for example, at the header block of a cardiac pacemaker). This has to do with the wavelength of the signals involved and where they couple efficiently into the system.

Magnetic field coupling into an implanted leadwire system is based on loop areas. For example, in a cardiac pacemaker unipolar lead, there is a loop formed by the leadwire as it comes from the cardiac pacemaker housing to its distal tip, for example, located in the right ventricle. The return path is through body fluid and tissue generally straight from the tip electrode in the right ventricle back up to the pacemaker case or housing. This forms an enclosed area which can be measured from patient X-rays in square centimeters. The average loop area is 200 to 225 square centimeters. This is an average and is subject to great statistical variation. For example, in a large adult patient with an abdominal implant, the implanted loop area is much larger (greater than 400 square centimeters).

Relating now to the specific case of MRI, the magnetic gradient fields would be induced through enclosed loop areas. However, the pulsed RF fields, which are generated by the body coil, would be primarily induced into the leadwire system by antenna action.

At the frequencies of interest in MRI, RF energy can be absorbed and converted to heat. The power deposited by RF pulses during MRI is complex and is dependent upon the power (Specific Absorption Rate (SAR) Level) and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AIMD and its associated leadwire(s). For example, it will make a difference how much EMF is induced into a pacemaker leadwire system as to whether it is a left or right pectoral implant. In addition, the routing of the lead and the lead length are also very critical as to the amount of induced current and heating that would occur. Also, distal tip design is very important as the distal tip itself can act as its own antenna wherein eddy currents can create heating. The cause of heating in an MRI environment is twofold: (a) RF field coupling to the lead can occur which induces significant local heating; and (b) currents induced between the distal tip and tissue during MRI RF pulse transmission sequences can cause local Ohms Law (resistive) heating in tissue next to the distal tip electrode of the implanted lead. The RF field of an MRI scanner can produce enough energy to induce leadwire RF voltages and resulting currents sufficient to destroy some of the adjacent myocardial tissue. Tissue ablation has also been observed. The effects of this heating are not readily detectable by monitoring during the MRI. Indications that heating has occurred would include an increase in pacing threshold, venous ablation, Larynx or esophageal ablation, myocardial perforation and lead penetration, or even arrhythmias caused by scar tissue. Such long term heating effects of MRI have not been well studied yet for all types of AIMD leadwire geometries. There can also be localized heating problems associated with various types of electrodes in addition to tip electrodes. This includes ring electrodes or pad electrodes. Ring electrodes are commonly used with a wide variety of implanted devices including cardiac pacemakers, and neurostimulators, and the like. Pad electrodes are very common in neurostimulator applications. For example, spinal cord stimulators or deep brain stimulators can include a plurality of pad electrodes to make contact with nerve tissue. A good example of this also occurs in a cochlear implant. In a typical cochlear implant there would be sixteen ring electrodes placed up into the cochlea. Several of these ring electrodes make contact with auditory nerves. Although there are a number of studies that have shown that MRI patients with active implantable medical devices, such as cardiac pacemakers, can be at risk for potential hazardous effects, there are a number of reports in the literature that MRI can be safe for imaging of pacemaker patients when a number of precautions are taken (only when an MRI is thought to be an absolute diagnostic necessity). While these anecdotal reports are of interest, they are certainly not scientifically convincing that all MRI can be safe. For example, just variations in the pacemaker leadwire length can significantly affect how much heat is generated. A paper entitled, HEATING AROUND INTRAVASCULAR GUIDEWIRES BY RESONATING RF WAVES by Konings, et al., Journal of Magnetic Resonance Imaging, Issue 12:79-85 (2000), does an excellent job of explaining how the RF fields from MRI scanners can couple into implanted leadwires. The paper includes both a theoretical approach and actual temperature measurements. In a worst-case, they measured temperature rises of up to 74 degrees C. after 30 seconds of scanning exposure. The contents of this paper are incorporated herein by reference.

The effect of an MRI system on the function of pacemakers, ICDs, neurostimulators and the like, depends on various factors, including the strength of the static magnetic field, the pulse sequence, the strength of RF field, the anatomic region being imaged, and many other factors. Further complicating this is the fact that each patient's condition and physiology is different and each manufacturer's pacemaker and ICD designs also are designed and behave differently. Most experts still conclude that MRI for the pacemaker patient should not be considered safe.

It is well known that many of the undesirable effects in an implanted leadwire system from MRI and other medical diagnostic procedures are related to undesirable induced EMFs in the leadwire system and/or RF currents in its distal tip (or ring) electrodes. This can lead to overheating of body tissue at or adjacent to the distal tip.

Distal tip electrodes can be unipolar, bipolar and the like. It is very important that excessive current not flow at the interface between the distal tip electrode and body tissue. In a typical cardiac pacemaker, for example, the distal tip electrode can be passive or of a screw-in helix type as will be more fully described. In any event, it is very important that excessive RF current not flow at this junction between the distal tip electrode and for example, myocardial or nerve tissue. This is because tissue damage in this area can raise the capture threshold or completely cause loss of capture. For pacemaker dependent patients, this would mean that the pacemaker would no longer be able to pace the heart. This would, of course, be life threatening for a pacemaker dependent patient. For neurostimulator patients, such as deep brain stimulator patients, the ability to have an MRI is equally important.

Accordingly, there is a need for novel RF impeding and/or diverting circuits, which are frequency selective and are constructed of passive components for implantable leadwires. The purpose of these circuits is to prevent MRI induced energy from reaching the distal tip electrode or its interface with body tissue. By redirecting said energy to locations at a point distant from the distal electrodes, this minimizes or eliminates hazards associated with overheating of said distal electrodes during diagnostic procedures, such as MRI. Such circuits should decouple and transfer energy which is induced from the MRI pulsed RF field to an energy dissipating surface. The present invention fulfills these needs and provides other related advantages.

SUMMARY OF THE INVENTION

The present invention includes frequency selective impeding and diverting (decoupling) circuits which transfer energy which is induced from the MRI pulsed RF field to an energy dissipating surface (EDS). In this way, RF energy can be shunted harmlessly into the bulk of a probe or catheter, body tissues distant from the distal electrodes, or into flowing blood or other body fluids thereby directing such energy away from a distal tip electrode.

In other words, a novel energy dissipating surface is provided with means for decoupling RF signals from implantable leadwires selectively to said energy dissipating surface. Referring to Provisional Application Ser. No. 60/283,725, Paragraph 4.5, it is stated, "In the previous studies, concerns have been raised about the safety of using metallic structures in MR scanners. Radio frequency energy (MHz)—transmitted from the scanner in order to generate the MR signal—can be deposited on the interventional device. This results in high electrical fields around the instrument and local tissue heating. This heating tends to be most concentrated at the ends of the electrical structure." This is certainly true of the implanted leadwires associated with AIMDs. "We can address this safety issue using the methods of the invention. The concern is that the surface ring electrodes, which directly contact the tissue, could cause local tissue changes including burns." The present invention is extended beyond the leadwires of probes and catheters to include the distal tip electrodes associated with the implanted leads of devices such as pacemakers, cardioverter defibrillators, neurostimulators and the like. All of these devices have a distal electrode which contacts body tissue in order to deliver pacing pulses or sense biologic activity. It is extremely important that that interface junction not overheat and cause localized tissue damage or burning.

The '725 Provisional Application explains the need to cut/remove the electrodes from the circuit in the MHz frequency range. This is accomplished with the inductor circuit elements. In the MHz frequency range, the surface ring electrodes are not connected to the rest of the electrical leads. Therefore, the ends of the leads are now buried inside of the catheter. The coupled high electric fields will now be located inside of the catheter instead of in the tissue. This results in significant reduction and unwanted tissue heating.

In the '725 Provisional Application, the inside of the catheter, of course, includes a body with a specific thermal mass and specific thermal properties. Over time, it will rise in temperature and therefore heat surrounding body tissue. However, this temperative rise is minimal due to the large area and thermal mass of the catheter which acts as an energy dissipating area or surface. Also, any such minimal heating that does occur is in body tissue in an area that is distant from the therapy electrode(s). Therefore, the ability for the pacing or stimulus electrode to delivery energy in the proper location will not be compromised. By spreading the RF energy over a larger surface area (i.e. inside the catheter) the temperature rise is therefore reduced and the resulting small amount of heat is generally dissipated into bulk body tissues instead of at a specific point.

This is accomplished through broad band filtering such as capacitance coupling, or by resonant filtering such as creating resonant circuits consisting of a series inductor and capacitor. These general concepts are described in U.S. Provisional Patent Application No. 60/283,725, and U.S. Patent Application Publication No. 2003/0050557, the contents of which are incorporated herein by reference. Using series bandstop filters is described in U.S. Pat. No. 7,363,090 and U.S. Patent Application Publication Nos. 2007-0112398 A1, 2008-0071313 A1, 2008-0049376 A1, 2008-0132987 A1, 2008-0116997 A1, the contents of which are incorporated herein by reference.

There are three types of electromagnetic fields used in an MRI unit. The first type is the main static magnetic field designated $B_0$ which is used to align protons in body tissue. The field strength varies from 0.5 to 3 Tesla in most of the currently available MRI units in present clinical use. The second electromagnetic field is the pulsed RF field which is given by the Lamor Frequency. The Lamor Frequency formula is 42.56 (static field strength in Tesla)=RF frequency. For example, for a 1.5 Tesla scanner, the frequency of the pulsed RF field is approximately 64 MHz. The third type of field is the gradient field which is used to control where the slice is that generates the image is located within body tissue.

The present invention is primarily directed to the pulsed RF field although it also has applicability to the gradient field as well. Because of the presence of the powerful static field, non-ferromagnetic components are presently used throughout the present invention. The use of ferromagnetic components is contraindicative because they have a tendency to saturate or change properties in the presence of the main static field.

In a broad sense, the present invention relates to a passive component network for an implantable leadwire of an active implantable medical device (AIMD), comprising: (1) at least one leadwire having a length extending between and to a proximal end and a tissue-stimulating or biological-sensing electrode at a distal tip end; and (2) a frequency selective energy diversion circuit for diverting and/or impeding high-frequency energy away from the electrode to a point or an area spaced from the electrode for dissipation of said high-frequency energy. The high-frequency energy may comprise an MRI frequency or a range of MRI frequencies in megahertz selected from the group of frequencies comprising 42.56 times strength in Teslas of an MRI scanner. The frequency selective energy diversion circuit may comprise a low pass filter such as a capacitor, an inductor, a Pi filter, a T filter, an LL filter, or an "n" element filter. Moreover, the frequency selective energy diversion circuit may comprise one or more series resonant LC trap filters.

An energy dissipating surface is preferably disposed at a point or an area spaced from the electrode, for example, within the blood flow of a patient. The energy dissipating surface may comprise a conductive housing, a ring electrode, a sheath, an insulative body, or a thermally conductive element. Moreover, the energy dissipating surface may comprise convolutions or fins for increasing the surface area thereof, or may comprise a roughened surface. The roughened surface may be formed through plasma or chemical etching processes, porous or fractal coatings or surfaces, whiskers, morphologically designed columnar structures, vapor, electron beam or sputter deposition of a high surface area energy conductive material, or by application of carbon nanotubes.

A leadwire housing may be provided which supports the leadwire distal tip electrode at one end thereof. The leadwire housing includes a conductive housing portion forming an energy dissipating surface, and an insulator housing portion between the leadwire distal tip electrode and the conductive housing portion.

An impeding circuit may be associated with the diversion circuit for raising the high-frequency impedance of the leadwire. The impedance circuit is disposed between the diversion circuit and the distal tip end of the at least one leadwire. The impeding circuit may comprise an inductor or a bandstop filter.

The leadwire may comprise a portion of a probe or a catheter, or it may comprise a pair of leadwires each having a length extending between and to a proximal end and a tissue-stimulating or biological-sensing electrode at a distal tip end. The diversion circuit may couple each of the leadwires to an energy dissipating surface disposed at a point or an area spaced from each of said electrodes. The diversion circuit may also be coupled between the pair of leadwires.

The diversion circuit may be mounted within a conductive housing which protects the diversion circuit from direct contact with patient body fluids. In this case, the conductive housing is preferably hermetically sealed. The active implantable medical device (AIMD) may comprise a deep brain stimulator. In this case, the conductive housing would be adapted for mounting in thermal communication with a patient's skull and/or dura. An electrode shaft assembly having a proximal end is carried by the conductive housing, and the leadwire(s) extends through the electrode shaft assembly and has the distal tip end electrode in position for contacting patient brain tissue.

Further, the energy dissipating surface may be disposed within an insulative sheath, and comprise at least a portion of a handle or pistol grip for a steerable probe or catheter. The energy dissipating surface may also comprise a plurality of spaced-part energy dissipating surfaces.

In other embodiments, a tether may be disposed between and conductively coupled with the electrode and the energy dissipating surface. The electrode may comprise a paddle electrode disposed on one side of a paddle, wherein the energy dissipating surface is disposed on a second side of the paddle. In this case, the frequency selective diversion circuit would comprise a capacitive element disposed within the paddle between the electrode and the energy dissipating surface.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 2 is a diagrammatic view of a typical probe or catheter;

FIG. 3 is a diagrammatic view of the interior of the prober or catheter of FIG. 2;

FIG. 4 is an electrical circuit diagram of the structure shown in FIG. 3, with a general impedance element connected between leadwires;

FIG. 5 is an electrical diagrammatic view similar to FIG. 4, illustrating a capacitor representing a frequency dependent reactive element between the leadwires;

FIG. 6 is a view similar to FIG. 5, wherein the general reactance element has been replaced by a capacitor in series with an inductor;

FIG. 7 is a view similar to FIGS. 4-6, showing the addition of series frequency selective reactances;

FIG. 8 is similar to FIG. 3, showing a low frequency model of the catheter and associated leads described in FIG. 2;

FIG. 9 is a view similar to FIGS. 3-8, illustrating how the distal rings are electrically isolated at a high frequency;

FIG. 10 is a view similar to FIGS. 3-9, showing the addition of series inductor components added to the frequency selective elements 20;

FIG. 11 is similar to FIGS. 3-10, illustrating frequency selective elements which incorporate parallel resonant inductor and capacitor bandstop filters;

FIG. 12 is a perspective and somewhat schematic view of a prior art active implantable medical device (AIMD) including a leadwire directed to the heart of a patient;

FIG. 13 is a diagram of a unipolar active implantable medical device;

FIG. 14 is a diagram similar to FIG. 13, illustrating a bipolar AIMD system;

FIG. 15 is a diagram similar to FIGS. 13 and 14, illustrating a bipolar leadwire system with a distal tip and ring electrodes, typically used in a cardiac pacemaker;

FIG. 30 is a sectional view of an hermetically sealed electrode assembly designed for contact with body fluid;

FIG. 31 is a perspective sectional view of a housing portion of the sealed electrode assembly of FIG. 30;

FIG. 31A is an enlarged sectional view corresponding generally with the encircled region 31A-31A of FIG. 31, and illustrating the principle of increasing the surface area of the energy dissipating surface;

FIG. 32 is a schematic circuit diagram corresponding with the sealed electrode assembly of FIG. 30;

FIG. 33A is a perspective view of an exemplary monolithic capacitor for use in the circuit of FIG. 32;

FIG. 33B is a perspective view of an exemplary unipolar feedthrough capacitor for use in the circuit of FIG. 32;

FIG. 59 is an enlarged, fragmented sectional view taken along the line 59-59 from FIG. 58, illustrating a roughened surface formed through, for example, plasma or chemical etching, or the like;

DETAILED DESCRIPTION OF THE PREFERRED EMBODIMENTS

Figure 1:
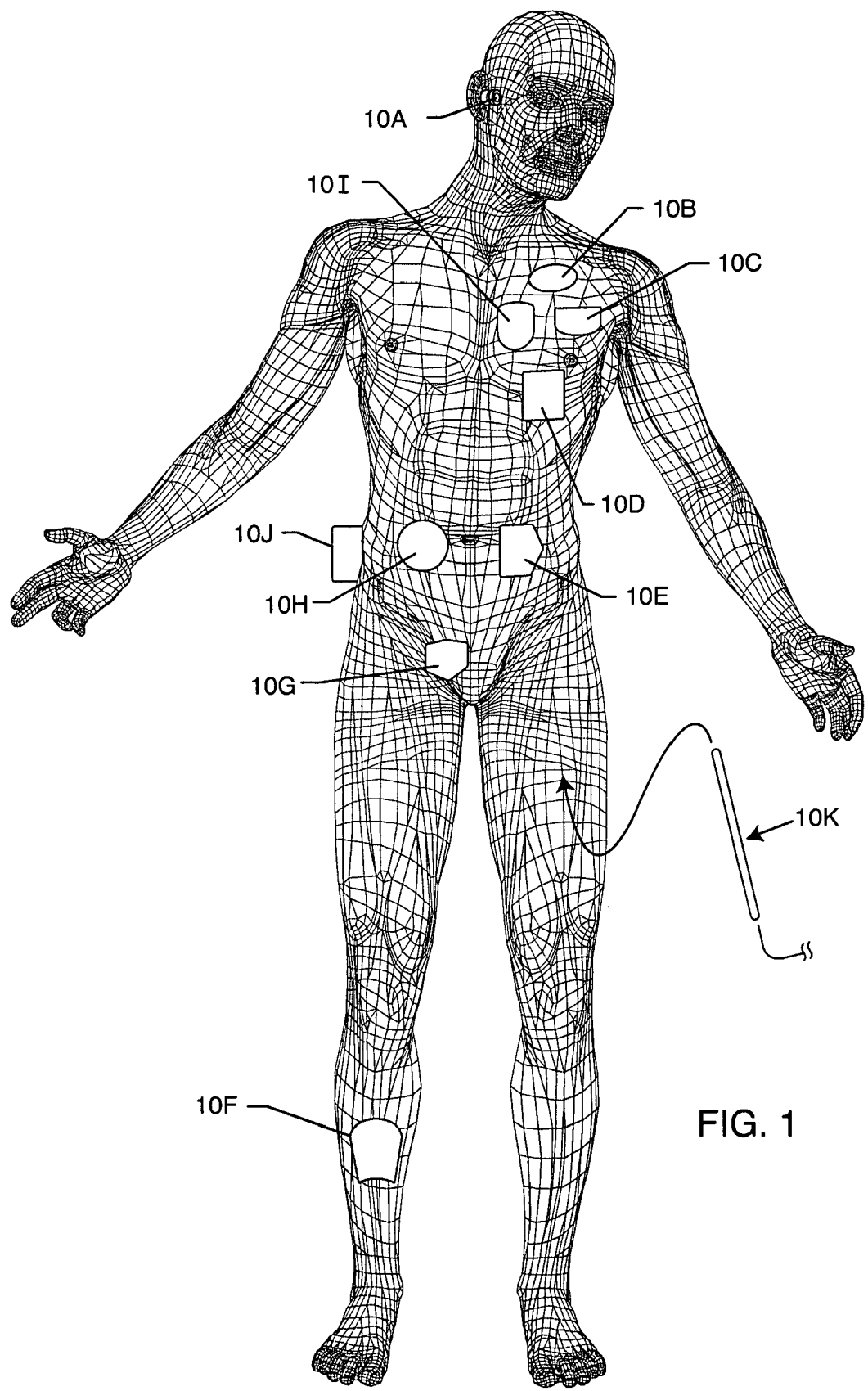
FIG. 1 is wire-formed diagram of a generic human body showing a number of active implantable medical devices (AIMDs)

FIG. 1 illustrates various types of active implantable medical devices referred to generally by the reference numeral 10 that are currently in use. FIG. 1 is a wire formed diagram of a generic human body showing a number of exemplary implanted medical devices. 10A is a family of implantable hearing devices which can include the group of cochlear implants, piezoelectric sound bridge transducers and the like. 10B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of the seizure and also providing electrical stimulation to brain tissue to prevent the seizure from actually happening. 10C shows a cardiac pacemaker which is well-known in the art. 10D includes the family of left ventricular assist devices (LVAD's), and artificial hearts, including the recently introduced artificial heart known as the Abiocor. 10E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted leadwires. 10F includes a variety of implantable bone growth stimulators for rapid healing of fractures. 10G includes urinary incontinence devices. 10H includes the family of pain relief spinal cord stimulators and anti-tremor stimulators. 10H also includes an entire family of other types of neurostimulators used to block pain. 10I includes a family of implantable cardioverter defibrillator (ICD) devices and also includes the family of congestive heart failure devices (CHF). This is also known in the art as cardio resynchronization therapy devices, otherwise known as CRT devices. 10J illustrates an externally worn pack. This pack could be an external insulin pump, an external drug pump, an external neurostimulator or even a ventricular assist device. 10K illustrates the insertion of an external probe or catheter. These probes can be inserted into the femoral artery, for example, or in any other number of locations in the human body.

Referring to U.S. Publication No. U.S. 2003/0050557, Paragraphs 79 through 82, the contents of which are incorporated herein, metallic structures, particularly leadwires, are described that when placed in MRI scanners, can pick up high electrical fields which results in local tissue heating. This heating tends to be most concentrated at the ends of the electrical structure (either at the proximal or distal lead ends). This safety issue can be addressed using the disclosed systems and methods of the present invention. The concern is that the distal electrodes, which directly contact body tissue, can cause local tissue burns.

Reference is made to U.S. Publication No. 2003/0050557 drawing, FIGS. 1A through 1G. These figures have been redrawn herein as FIGS. 2 through 11 and are described as follows in light of the present invention.

FIG. 2 is a diagrammatic view of a typical prior art device 10 such as a probe or catheter. There are two leadwires 12 and 14 which thread through the center of the illustrative probe or catheter and terminate respectively in a corresponding pair of distal conductive electrode rings 16 and 18. Leadwires 12 and 14 are electrically insulated from each other and also electrically insulated from any metallic structures located within the catheter body. The overall catheter body is generally flexible and is made of biocompatible materials, which also have specific thermal properties. In addition to flexibility, probes and catheters are typically steerable. It is well known that a push-pull wire (not shown in FIG. 2) can be run down the center of the catheter or probe in a lumen and then be attached to a catheter handle or pistol grip or other device so that the physician can carefully steer or thread the probe or catheter through the torturous path of the venous system, even into the ventricles of the heart. Such probes and catheters, for example, can be used for electrical mapping inside of a heart chamber, or for application of RF energy for ablation, which is used to treat certain cardiac arrhythmias. Probes and catheters have wide application to a variety of other medical applications. There are also combined catheters that can do electrical mapping and can also perform RF ablation. When the physician finds the area of arrhythmic electrical activity and wishes to ablate, he activates a switch which applies RF energy to the tip of the catheter (see, e.g., FIG. 55, which will be discussed herein in more detail). This would involve a third electrode right at the catheter tip of FIG. 2 (not shown). It would be extremely valuable if the catheter could be guided during real-time MRI imaging. This is important because of MRI's incredible ability to image soft tissue. In addition, when one is doing deliberate ablation, for example, around a pulmonary vein, it is important that a full circle of scar tissue be formed, for example, to stop atrial fibrillation. MRI has the ability to image the scar as it is being formed (for example, see U.S. Pat. No. 7,155,271). However, it would be highly undesirable if the MRI RF energy that is coupled to the leadwires caused the distal ablation tip or the electrode rings to overheat at an improper time, which could burn or ablate healthy tissues.

FIG. 3 shows the interior taken from FIG. 2 showing leadwires 12 and 14 which are routed to the two distal electrodes 16 and 18 as previously described in FIG. 2.

FIG. 4 shows the electrical circuit of FIG. 3 with a general frequency selective impedance element 20 connected between leadwires 12 and 14. In the present invention, the impedance element 20 can consist of a number of frequency selective elements as will be further described. In general, the first conductive leadwire 12 is electrically coupled to the first electrode 116, the second conductive leadwire 14 is electrically coupled to the second electrode 18, and the frequency dependent reactive element 20 electrically couples the first and second leadwires 12 and 14 such that high frequency energy is conducted between the first leadwire 12 and the second leadwire 14.

Referring once again to FIG. 4, the frequency dependent reactive element 20 tends to be electrically invisible (i.e., a very high impedance) at selected frequencies. The reactive element is desirably selective such that it would not attenuate, for example, low frequency biological signals or RF ablation pulses. However, for high frequency MRI RF pulsed frequencies (such as 64 MHz), this frequency reactive element 20 would look more like a short circuit. This would have the effect of sending the energy induced into the leadwires 12 and 14 by the MRI RF field back into the catheter body itself into which the leadwires are embedded. In other words, there are both RF energy and thermal conductivity to the probe or catheter body or sheath or shield which becomes an energy dissipating surface all along the lengths of leadwires 12 and 14 such that MRI induced energy that is present in these leadwires is diverted and converted to heat into the interior and along the catheter body itself. This prevents the heat build up at the extremely sensitive locations right at the ring electrodes 16 and 18 which are in intimate and direct contact with body tissue. In addition, the amount of temperature rise is very small (just a few degrees) because of the energy being dissipated over such a relatively high surface area. As previously mentioned, the high frequency RF pulsed energy from an MRI system can couple to implanted leads. This creates electromagnetic forces which can result in current flowing through the interface between electrodes that are in contact with body tissue. If this current reaches certain values, body tissue could be damaged by heat build-up. This can create scar tissue formation, tissue damage or even tissue necrosis such to the point where the AIMD can no longer deliver appropriate therapy. In certain situations, this can be life threatening for the patient.

FIG. 5 shows a capacitor 22 which represents one form of the frequency dependent reactive element 20 previously described in FIG. 4. In this case, the reactive element comprises a simple capacitor 22 connected between the first conductor or leadwire 12 and the second conductor or leadwire 18 and will have a variable impedance vs. frequency. The following formula is well known in the art: $X_c = 1/(2\pi f c)$. Referring to the equation, one can see that since frequency (f) is in the denominator, as the frequency increases, the capacitive reactance in ohms decreases. With a large number in the denominator, such as the RF pulsed frequency of a 1.5 Tesla MRI system, which is 64 MHz, the capacitive reactance drops to a very low number (essentially a short circuit). By shorting the leadwires together at this one frequency, this diverts and prevents the RF energy from reaching the distal ring electrodes 16 and 18 and being undesirably dissipated as heat into body tissue. Referring once again to FIG. 4, one can see that the impedance element 20 thereby diverts the high frequency RF energy back into the leadwires 12 and 14. By spreading this energy along the length of leadwires 12 and 14, it is converted to heat, which is dissipated into the main body of the probe, catheter or insulation sheath. In this way, the relatively large thermal mass of the probe or catheter becomes an energy dissipating surface and any temperature rise is just a few degrees C. In general, a few degrees of temperature rise is not harmful to body tissue. In order to cause permanent damage to body tissue, such as an ablation scar, it generally requires temperatures of approximately 50° C. In summary, the frequency dependent reactive element 20, which may comprise a capacitor 22 as shown in FIG. 5, forms a diversion circuit such that high frequency energy is diverted away from the distal electrodes 16 and 18 along the leadwires 12 and 14 to a point that is distant from the electrodes 16 and 18, at which point the energy is converted to heat.

FIG. 6 describes an even more efficient way of diverting high frequency energy away from the electrode and accomplishing the same objective. The general reactance element 20 described in FIG. 4 is shown in FIG. 6 to comprise the capacitor 22 in series with an inductor 24 to form an L-C trap circuit. There is a particular frequency ($f_r$) at which the capacitive reactance $X_C$ and the inductive reactance $X_L$ are equal and opposite and tend to cancel each other out. If there are no losses in such a system, this results in a perfect short circuit between leadwires 12 and 14 at the resonant frequency. The frequency of resonance is given by the equation $$f_r = \frac{1}{2\pi\sqrt{LC}},$$

wherein $f_r$ is the frequency of resonance in Hertz, L is the inductance in henries, and C is the capacitance in farads.

FIG. 7 illustrates any of the aforementioned frequency dependent impedance elements 20 with the addition of series frequency selective reactances 26 and 28. The addition of series impedance further impedes or blocks the flow of high frequency MRI induced currents to the ring electrodes 16 and 18 as will be more fully described in the following drawings.

FIG. 8 is the low frequency model of FIG. 4, 5 or 6. In this regard, FIG. 8 is identical to FIG. 3, in that, once again it shows the electrical leadwires 12 and 14 connected to the distal ring electrodes 16 and 18 of the probe or catheter 10. In the low frequency model, the frequency reactive impedance elements 20 disappear because at low frequency their impedances approach infinity. Of course, leads in a probe or catheter are electrically equivalent to leads used for cardiac pacemakers, implantable cardioverter defibrillators, neurostimulators and the like. For example, reference is made to U.S. Pat. No. 7,363,090, the contents of which are incorporated herein. Accordingly, any discussion related to probes or catheters apply equally to leadwires for all active implantable medical devices as described in FIG. 1, and vice versa. Referring once again to FIG. 8, this is also the low frequency model of the circuits shown in FIG. 7. At low frequency, the frequency selective or reactive component 20 tends to look like a very high or infinite impedance. The series reactive or frequency variable elements 26 and 28 at low frequency tend to look like a very low impedance or short circuit. Accordingly, they all tend to disappear as shown in FIG. 8.

FIG. 9 is a high frequency model that illustrates how the distal electrodes or rings 16 and 18 are electrically isolated at high frequency by shorting leadwires 12 and 14 at location 30. As previously mentioned, such shorting or current diverting could be accomplished by a series resonant L-C trap circuit. FIG. 9 also shows the electrodes 16 and 18 as cut or disconnected and electrically isolated from the rest of the circuit. This is because, at very high frequency, series selective frequency (reactive) elements 26 and 28 tend to look like a very high impedance or an open circuit. In summary, by reactive elements 20, 26 and 28 acting cooperatively, reactive element 20 diverts the high frequency energy while at the same time reactive elements 26 and 28 impede the high frequency RF energy. Accordingly, in the ideal case, the equivalent circuit of FIG. 9 is achieved. The high frequency MRI RF energy cannot reach the distal ring electrodes 16, 18 and cause undesirable heating at that critical tissue interface location.

FIG. 10 shows any of the previously described diverting frequency selective elements 20 in combination with series reactance components 26' and 28' shown in the form of a pair of inductors. It is well known to electrical engineers that the inductive reactance in ohms is given by the equation $X_L=2\pi fL$. In this case the frequency term (f) is in the numerator. Accordingly, as the frequency increases, the reactance (ohms) of the inductors also increases. When the frequency is very high (such as 64 MHz) then the reactance in ohms becomes extremely high (ideally approaches infinity and cuts off the electrodes). By having a short circuit or very low impedance between the leadwires 12 and 14 and then, at the same time, having a very high impedance in series with the electrodes from inductors 26' and 28', this provides a very high degree of attenuation to MRI RF pulsed frequencies thereby preventing such energy from reaching the distal ring electrodes 16 and 18. In FIG. 10, the line-to-line selective impedance element 20 diverts high frequency energy back into leadwires 12 and 14 while at the same time the series inductors 24' and 25' impede (or cut-off) high frequency energy. When the line-to-line element 20 is a capacitor 22 as shown in FIG. 5, then this forms what is known in the prior art as an L section low pass filter, wherein the capacitor 22 electrically cooperates with the inductors 26' and 28' (FIG. 10) to form a 2-element low pass filter. By definition, a low pass filter allows low frequencies such as biological signals to pass to and from the distal electrodes through freely without attenuation while at the same time provides a high degree of attenuation to undesirable high frequency energy. It will be obvious to those skilled in the art that FIG. 5 describes a single element low pass filter, and that FIG. 10 describes a 2-element or L-section low pass filter. Moreover, any number of inductor and capacitor combinations can be used for low pass filters, including 3-element Pi or T circuits, LL, 5-element or even "n" element filters.

FIG. 11 offers an even greater performance improvement over that previously described in FIG. 10. In FIG. 1, modified frequency selective elements 26" and 28" each incorporate a parallel resonant inductor and capacitor which is also known in the industry as a band stop filter. The L-C components for each of the reactive elements 26" and 28" are carefully chosen such that each of the band stop filters 26" and 28" is resonant, for example, at the pulsed resonant frequency of an MRI scanner. The pulsed resonant frequency of an MR scanner is given by the Lamor equation wherein the RF pulsed frequency in megahertz is equal to 42.56 times the static field strength. For example, for a popular 1.5 Tesla scanner, the RF pulsed frequency is 64 MHz. Common MR scanners that are either in use or in development today along with their RF pulsed frequencies include: 0.5 Tesla-21 MHz; 1.5 Tesla-64 MHz; 3 Tesla-128 MHz; 4 Tesla-170 MHz; 5 Tesla-213 MHz; 7 Tesla-300 MHz; 8 Tesla-340 MHz; and 9.4 Tesla-400 MHz. When the band stop filters 26" and 28" are resonant at any one of these RF pulsed frequencies, then these elements tend to look like an open circuit which impedes the flow of RF current to distal electrodes. When compatibility with different types of MR scanners is required, for example, 1.5, 3 and 5 Tesla, then three separate band stop filter elements in parallel may comprise the reactive element 26 (FIG. 7), and three separate band stop filter elements in parallel may comprise the reactive element 28 (FIG. 7). Each of these would have their L and C components carefully selected so that they would be resonant at different frequencies. For example, in the case of MR scanners operating at 1.5, 3 and 5 Tesla, the three band stop filters comprising the reactive element as well as the three band stop filters comprising the reactive element 25 would be resonant respectively at 64 MHz, at 128 MHz, and at 170 MHz. The resonant frequencies of the band stop filter elements could be selected such that they are resonant at the operating frequency of other emitters that the patient may encounter such as diathermy and the like. The use of band stop filters is more thoroughly described in U.S. Pat. No. 7,363,090 and Patent Publication Nos. US 2007-0112398 A1, US 2007-0288058, US 2008-0071313 A1, US 2008-0049376 A1, US 2008-0161886 A1, US 2008-0132987 A1 and US 2008-0116997 A1, the contents of which are incorporated herein.

Referring now to FIG. 12, a prior art active implantable medical device (AIMD) 10 is illustrated. In general, the AIMD 10 could, for example, be a cardiac pacemaker (10C in FIG. 1) which is enclosed by a titanium housing 32 as indicated. The titanium housing 32 is hermetically sealed, however, there is a point where conductors such as the illustrative conductors 34a, 34b, 34c and 34d must ingress and egress relative to the housing 32. This is accomplished by providing a hermetic terminal assembly 36. Hermetic terminal assemblies are well known and generally consist of a ferrule 38 which is laser welded to the titanium housing 32 of the AIMD 10. In FIG. 12, four conductors 34a-34d are shown for connection to a corresponding number of leadwires, such as the illustrative leadwire 12b shown for coupling to the conductor 34b. In this configuration, the four leadwires coupled respectively to the conductors 34a-34d comprise a typical dual chamber bipolar cardiac pacemaker.

Connectors 40 commonly known as IS-1 connectors are designed to plug into mating receptacles 42 on a header block 44 on the pacemaker housing 32. These are low voltage (pacemaker) leadwire connectors covered by an International Standards Organization (ISO) standard IS-1. Higher voltage devices, such as implantable cardioverter defibrillators, are covered by a standard known as the ISO DF-1. A new standard was recently published that will integrate both high voltage and low voltage connectors into a new miniature quadpolar connector series known as the ISO IS-4 standard. Leads plugged into these connectors are typically routed in a pacemaker or ICD application down into the right ventricle and right atrium of the heart 46. There are also new generation devices that have been introduced to the market that couple leads to the outside of the left ventricle. These are known as biventricular devices and are very effective in cardiac resynchronization therapy (CRT) and treating congestive heart failure (CHF).

In FIG. 12, one can see, for example, the conductors 34a and 34b that could be coupled by leads routed, for example, to distal tip and ring electrodes within the right ventricle of the heart 46. The other pair of conductors 34c and 34d could be coupled by leads routed to distal tip and ring electrodes within the right atrium of the heart 46. There is also an RF telemetry pin antenna 48 which is not connected to the IS-1 or DS-1 connector block. This acts as a short stub antenna for picking up telemetry signals that are transmitted from the outside of the device 10.

It should be obvious to those skilled in the art that all of the descriptions herein are equally applicable to other types of AIMDs. These include implantable cardioverter defibrillators (ICDs), neurostimulators, including deep brain stimulators, spinal cord stimulators, cochlear implants, incontinence stimulators and the like, and drug pumps. The present invention is also applicable to a wide variety of minimally invasive AIMDs. For example, in certain hospital cath lab procedures, one can insert an AIMD for temporary use such as a probe, catheter or femoral artery ICD. Ventricular assist devices also can fall into this type of category. This list is not meant to be limiting, but is only example of the applications of the novel technology currently described herein. In the following description, functionally equivalent elements shown in various embodiments will often be referred to utilizing the same reference number.

FIG. 13 is a general diagram of a unipolar active implantable medical device 10 and related system, wherein reference numbers common with those used in FIG. 12 refer to common structural and/or functional components. The housing 32 of the active implantable medical device 10 is typically titanium, ceramic, stainless steel or the like. Inside of the device housing are the AIMD electronic circuits. Usually AIMDs include a battery, but that is not always the case. A leadwire or lead 12 is routed from the AIMD 10 to a point 50 typically including or comprising an electrode embedded in or affixed to body tissue. In the case of a spinal cord stimulator 10H (FIG. 1), the distal tip 50 could be in the spinal cord. In the case of a deep brain stimulator 10B (FIG. 1), the distal electrode 50 would be placed deep into the brain, etc. In the case of a cardiac pacemaker 10C (FIG. 1), the distal electrode 50 would typically be placed in the cardiac right ventricle.

FIG. 14 is very similar to FIG. 13 except that it depicts a bipolar device 10 and related system. In this case, a first leadwire 12 is coupled to a first distal electrode 50, and a second distal electrode 52 and associated leadwire 14 provide an electric circuit return path between the two distal electrodes 50 and 52. In the case of a cardiac pacemaker 10C as shown in FIG. 15, this would be known as a bipolar leadwire system with one of the electrodes known as the distal tip electrode 50 and the other electrode which would float in the blood pool known as the ring electrode 52 (see FIG. 15). In contrast, the electrical return path in FIG. 13 is between the distal electrode 50 through body tissue to the conductive housing 32 of the implantable unipolar medical device 10.

In all of these applications, the patient could be exposed to the fields of an MRI scanner or other powerful emitter used during a medical diagnostic procedure. Currents that are directly induced in the leadwire system, such as the illustrative leadwires 12 and 14, can cause heating by P=I²R (Ohm's law) losses in the leadwire system or by heating caused by current flowing in body tissue. If these currents become excessive, the associated heating can cause damage or even destructive ablation to body tissue.

The distal tip electrode 50 is designed to be implanted against or into or affixed (screwed into) to the actual myocardial tissue of the heart 46. The ring electrode 52 is designed to float in the blood pool. Because the blood is flowing and is thermally conductive, some people feel that the ring structure 52 is substantially cooled. However, this is only in theory. Studies have shown, upon lead removal that the entire area of the tip and the ring can become overgrown and embedded in body tissue and thereby thoroughly encapsulated. Accordingly, in some pacemaker patients, both the distal tip and ring can become thermally insulated by surrounding body tissue and can readily heat up due to the RF pulsed currents of an MRI field.

Figure 16:
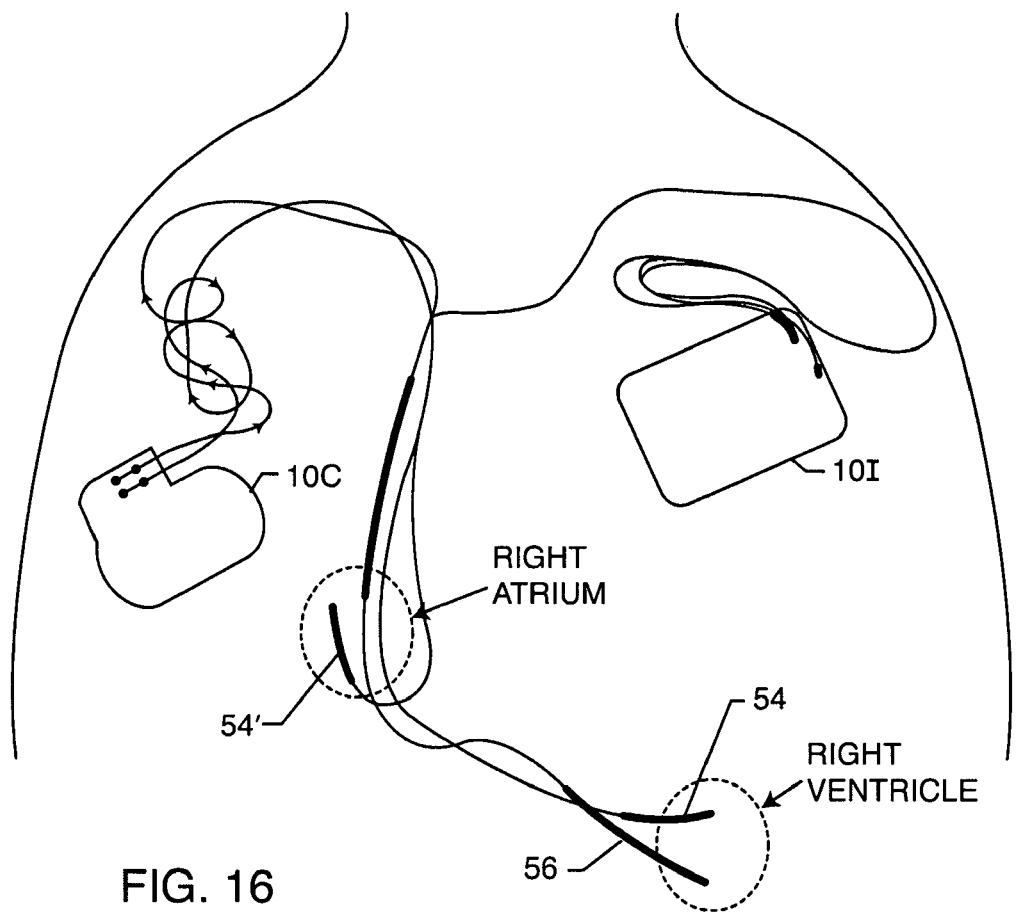
FIG. 16 is a tracing of an exemplary patient X-ray showing an implanted pacemaker and cardioverter defibrillator and corresponding leadwire system.

FIG. 16 is a tracing of an actual patient X-ray. This particular patient required both a cardiac pacemaker 10C and an implantable cardioverter defibrillator (ICD) 101. The corresponding implantable leadwire system, as one can see, makes for a very complicated antenna and loop coupling situation. The reader is referred to the article entitled, "Estimation of Effective Lead Loop Area for Implantable Pulse Generator and Implantable Cardioverter Defibrillators" provided by the AAMI Pacemaker EMC Task Force.

In FIG. 16, one can see that from the pacemaker 10C, there is an electrode 54 and 54' in both the right atrium and in the right ventricle. Both these involve a separate tip and ring electrode (not shown in FIG. 16). In the industry, this is known as a dual chamber bipolar leadwire system. It will be obvious to those skilled in the art that any of the passive frequency selective networks, as previously described in FIGS. 2 through 11, can be incorporated into the leadwires as illustrated in the X-ray tracing of FIG. 16. One can also see that the implantable cardioverter defibrillator (ICD) 101 is associated with an electrode 56 implanted directly into the right ventricle. Its shocking tip and perhaps its superior vena cava (SVC) shock coil would also require the passive, frequency selective diverter and/or impeding filters of FIGS. 2-11 of the present invention so that MRI exposure cannot induce excessive currents into the associated leadwires or electrodes. Modern implantable cardioverter defibrillators (ICDs) incorporate both pacing and cardioverting (shock) features. Accordingly, it is becoming quite rare for a patient to have a leadwire layout as shown in the X-ray of FIG. 16. However, the number of electrodes remains the same. There are also newer combined pacemaker/ICD systems which include biventricular pacemaking (pacing of the left ventricle). These systems can have as many as 9 to even 12 leadwires.

Figure 17:
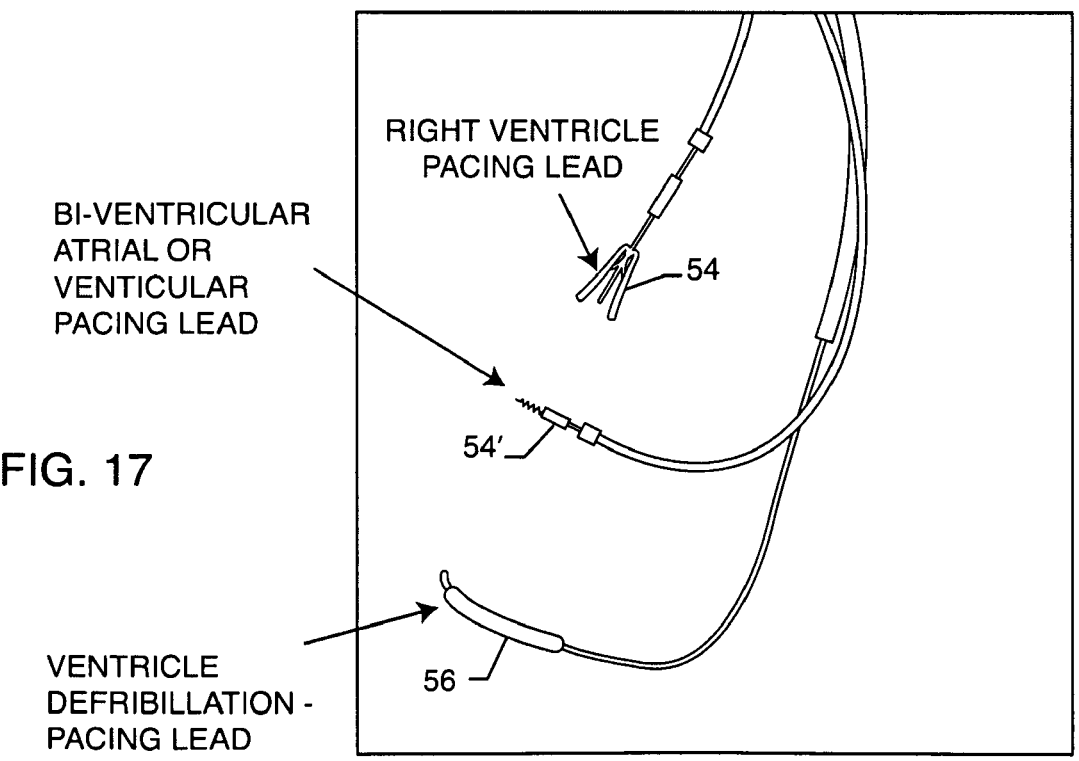
FIG. 17 is a line drawing of an exemplary patient cardiac X-ray of a bi-ventricular leadwire system.

FIG. 17 is a line drawing of an actual patient cardiac X-ray of one of the newer bi-ventricular leadwire systems with various types of electrode tips 54, 54' and 56 shown. The new bi-ventricular systems are being used to treat congestive heart failure, and make it possible to implant leads outside of the left ventricle. This makes for a very efficient pacing system; however, the implantable leadwire system is quite complex. When a leadwire system, such as those described in FIGS. 12, 13, 14, 15, 16 and 17, are exposed to a time varying electromagnetic field, electric currents can be induced into the electrodes of such leadwire systems. For the bi-ventricular system, a passive component frequency selective network of FIGS. 2-11 would need to be placed in conjunction with each of the three distal tips and ring electrodes to corresponding energy dissipating surfaces.

The word passive is very important in this context. Active electronic circuits, which are defined as those that require power, do not operate very well under very high intensity electromagnetic field conditions. Active electronic filters, which generally are made from micro electronic chips, have very low dynamic range. Extremely high fields inside an MRI chamber would tend to saturate such filters and make them become nonlinear and ineffective. Accordingly, frequency selective networks are preferably realized using non-ferromagnetic passive component elements. Passive component elements are capable of handling very high power levels without changing their characteristics or saturating. Moreover, the inductor elements are preferably made from materials that are not ferromagnetic. The reason for this is that MRI machines have a very powerful main static magnetic field ($B_0$). This powerful static magnetic field tends to saturate ferrite elements and would thereby change dramatically the value of the inductance component. Accordingly, virtually all inductor elements are fabricated without the use of ferrites, nickel, iron, cobalt or other similar ferromagnetic materials that are commonly used in general electronic circuit applications.

Figure 18:
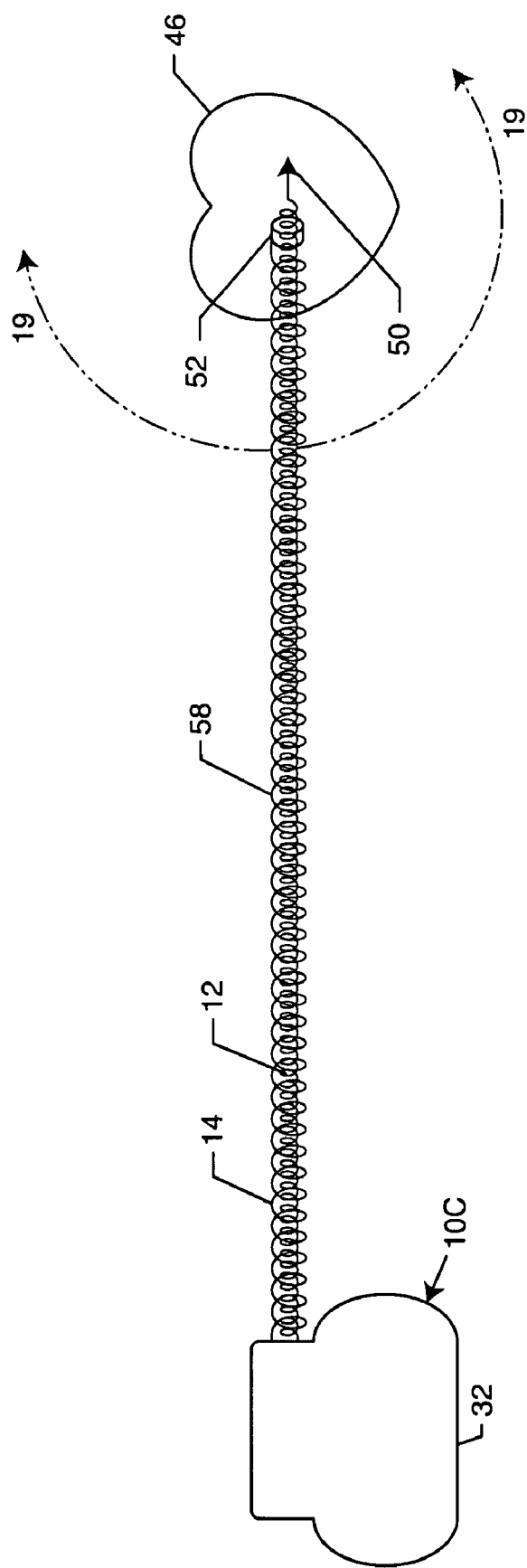
FIG. 18 illustrates a bipolar cardiac pacemaker leadwire showing the distal tip and the distal ring electrodes.

FIG. 18 illustrates a single chamber bipolar cardiac pacemaker 10C having a leadwire system and showing the distal tip 50 and the distal ring 52 electrodes. This is a spiral wound system where a ring coil leadwire 14 is wrapped around a tip coil leadwire 12, wherein these two leadwires 12, 14 extend between a sealed housing 32 and the pair of electrodes 50, 52. There are other types of pacemaker leadwire systems in which these two leads lay parallel to one another (known as a bifilar lead system). In FIG. 18, one can see an outer insulating sheath 58 which is typically of silicone or polyurethane. This protects the leadwires 12, 14 from direct exposure to body fluid and also insulates the leadwires. It also has its own thermal conductive properties as will be further described herein.

Figure 19:
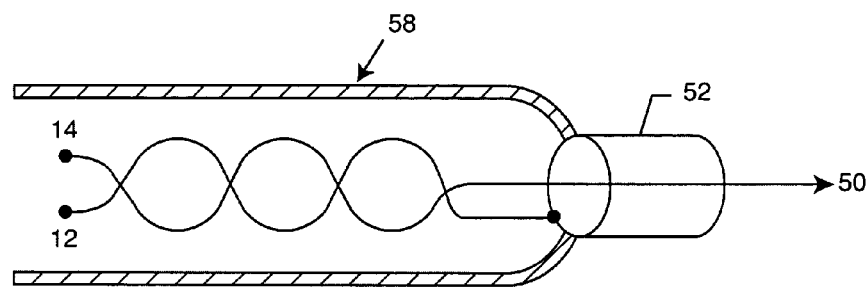
FIG. 19 is an enlarged schematic illustration of the area indicated by Line 19-19 in FIG. 18, showing details of the bipolar pacemaker leadwire system.
Figure 19A:
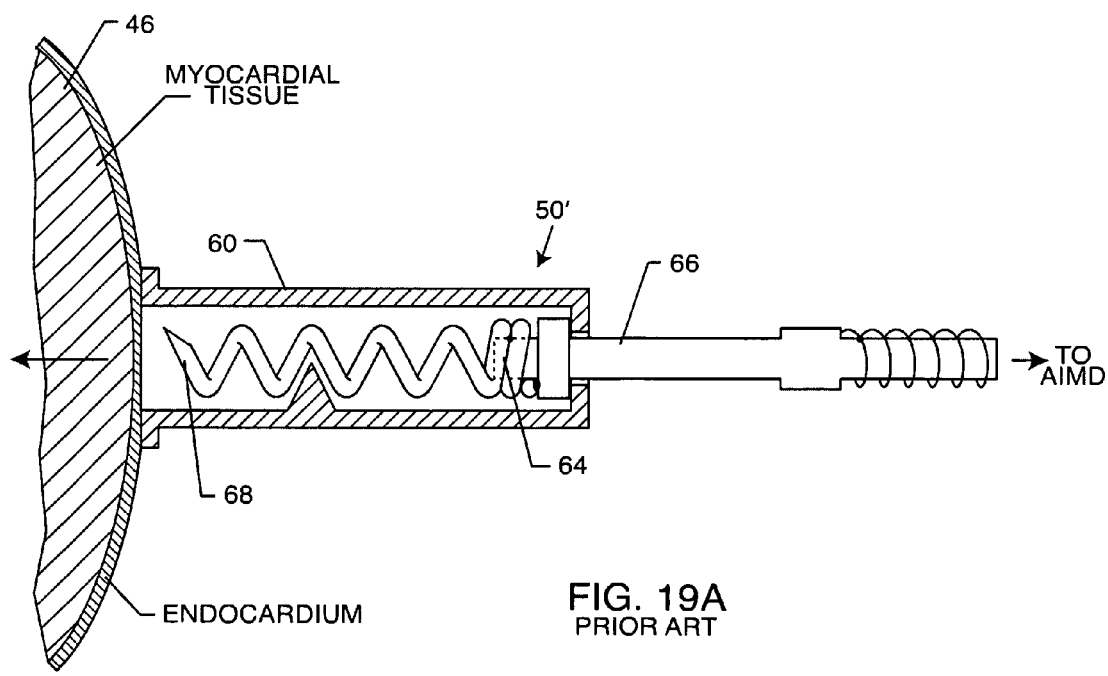
FIG. 19A is similar to FIG. 19, but depicts an active fixation tip for a bipolar pacemaker leadwire system.

FIG. 19 is generally taken from FIG. 18 showing a typical prior art bipolar pacemaker leadwire system. Shown is the distal tip electrode 50 and ring electrode 52. An insulation or insulative lead body 58 is also illustrated. The distal tip electrode can be passive (meaning that it can be bent back in a "J" or shoved against myocardial tissue so that it just rests against the tissue). A more commonly used electrode today is known as the active fixation tip. This is an electrode where by turning the entire center of the lead, the physicians can screw a helix into myocardial tissue thereby firmly affixing it. A prior art active fixation electrode tip 50' is shown in FIG. 19A. This is typically used in conjunction with a cardiac pacemaker, an implantable defibrillator or the like. One can see that an active fixation tip housing 60 is pressed up against the tissue to be stimulated, e.g., the myocardial tissue of the patient's heart. For example, this could be the septal wall between the right ventricle and the left ventricle. A helix electrode assembly 64 is shown in a retracted position relative to the adjacent heart tissue. Up in the pectoral pocket, the physician uses a tool to axially twist an assembly shaft 66, which drives a pointed tip helix screw 68 into the myocardial tissue, firmly affixing it. This type of active fixation tip 50' is becoming more popular. As can be seen, it would be highly undesirable for the active fixation helix screw 68 to heat up during an MRI scan. Because the helix screw 68 is deeply embedded into myocardial tissue, if excessive heating and temperature rise did occur, not only could scarring or ablation of cardiac tissue occur, but an actual cardiac wall perforation or lesion could result in sudden death. It will also be obvious to those skilled in the art that any of the frequency impeding or diverting circuits, as shown in FIG. 4, 5, 6, 7, 10 or 11, would be highly undesirable if they were located within the overall housing 60 of the active fixation tip 50'. This is because the heat would indeed be removed from the helix screw 68, but it would be transferred into the active fixation housing 60 which rests in intimate contact with the endocardium heart tissue. What this means is that redirecting the MRI induced electromagnetic energy from the helix tip 68 to the housing 60 simply moves the heat from one bad location to another bad location. Because the housing 60 is also in intimate contact with heart tissue, one would experience excessive temperature rise and resulting tissue burning, scarring or necrosis at that location as well.

Referring once again to FIG. 19, one can see that there is a ring electrode 52 which is placed back (spaced proximally) a suitable distance from the distal tip electrode 50. In a bipolar pacing system, the cardiac pacing pulse is produced between the tip electrode 50 and the ring electrode 52. This electrical pulse induced into myocardial tissue produces a heartbeat. Sensing is also accomplished between these two electrodes 50, 52 wherein the pacemaker can constantly monitor the electrical activity of the heart. There are similar analogies for neurostimulators, cochlear implants and the like. There is usually a point at which the distal electrodes, for example electrode 50, contact body tissue or fluid for delivery of therapy involving electrical energy. In a neurostimulator application, such as a spinal cord stimulator, small electrical currents or pulses are used to block pain in the spinal nerve roots. In a urinary incontinence stimulator, a distal electrode is used to cause a muscle contraction and thereby prevent undesirable leakage of urine. In all of these examples, it would be highly undesirable for excess heating defined as temperature rise above a few degrees C., to occur particularly at the distal electrode tip(s).

In previous studies, concerns have been raised about the safety of using metallic structures, such as leadwires and MR scanners. Radio frequency energy (MHz) transmitted from the MRI scanner in order to generate the MR signal can be coupled to on the interventional device or its associated leads. This results in high electrical fields around the instrument and local tissue heating. This heating tends to be most concentrated at the ends of the electrical structure or leads.

We can address this safety issue using the methods of the present invention. The concern is that distal electrodes or distal surface ring electrodes, which directly contact body tissue, will cause local tissue burns. We need to cut/remove the electrodes from the circuit in the MHz frequency range. In the current embodiment, this is accomplished with inductor circuit elements. In the MHz frequency range, the surface ring electrodes are not connected to the rest of the electrical leads (FIG. 9). Therefore, the ends of the leads are now buried inside of the catheter. The concentrated, high electric fields will now be located inside of the catheter instead of in the tissue. This results in a significant reduction in unwanted tissue heating.

A more effective way to "cut" or impede RF energy from the surface electrodes from the rest of the circuit would be to use a parallel resonant circuit in place of the inductors in FIG. 10. This resonant circuit could consist of an inductor in parallel with a capacitor (an L-C bandstop filter as shown in FIG. 11). If this parallel L-C circuit is tuned to the MR frequency, it will present a very high impedance at this frequency. This will effectively cut the surface electrodes from the elongated leads at the MRI frequency and prevent unwanted heating. For maximal effectiveness, the L-C circuit should be shielded. For a probe or a catheter application, with these design concepts, the electrical end of the leads (in the MHz range) are buried inside of the catheter body and as a result, the concentrated electric fields are also located inside of the capacitor, instead of in the tissue. This results in a significant reduction in unwanted tissue heating. As previously mentioned, a resonant circuit is an effective way to "cut" the surface electrodes from the rest of the electrical circuit. This resonant circuit could be an inductor in parallel with the capacitor (an L-C "tank" circuit). The L-C circuit may be placed distal to the electrodes and allowing the electrodes to be visualized. Probes and catheters often incorporate metallic sheaths which also assist in dissipating the unwanted energy over large surface areas. This is equivalent to the energy dissipating surface (EDS) structures as described herein.

All of the circuit elements as described in connection with FIGS. 4 through 11 are for purposes of redirecting high frequency RF energy away from distal electrodes into a location that has larger thermal mass and larger area such that the energy is not being dissipated at the concentrated point of electrode to tissue contact. Concentrating the MRI RF energy at an electrode causes excessive temperature rise which can result in damage to adjacent body tissues. Referring back to FIG. 3, one can see that the leadwires 12 and 14 are embedded in the insulating sheath of a probe, a catheter, a cardiac pacemaker lead or the like. Accordingly, if excess heat is dissipated along these leadwires, it is then dissipated into these surrounding structures. As previously mentioned, there is also a parasitic capacitance that's formed along these leadwires and the surrounding structures or insulating sheaths. It is a feature of the present invention that any of the passive component frequency selective circuits can also be directly connected to energy dissipating elements that are distal from the electrodes themselves.

Referring to FIG. 19 (and also FIGS. 20-22), the insulation sheath 58 typically encapsulates the leadwires 12 and 14 in silicone or polyurethane to provide strength and resistance to body fluids. The insulation sheath 58 has thermal conduction properties and also provides important electrical isolation between the leadwires 12 and 14 themselves and also surrounding body fluids and tissues.

Figure 20:
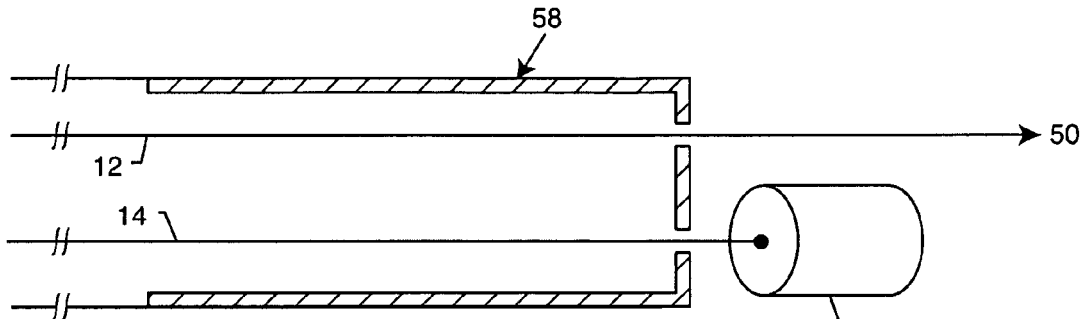
FIG. 20 is similar to FIG. 19, except that the twisted or coaxial electrode wires have been straightened out.

FIG. 20 is generally taken from FIG. 19 except that the twisted or coaxial electrode wires 12 and 14 have been straightened out for better illustration of the examples of the present invention. This is also analogous to FIG. 2 for the wires of probes and catheters previously described herein. The straightened and elongated leadwires 12, 14 of FIG. 20 are also illustrative of certain bifilar leadwire systems, which can also be used for pacemakers, neurostimulators and the like. In other words, the leadwires are not always twisted as shown in FIG. 19 as there are certain applications where it is desirable to have the leadwires 12, 14 running parallel to each other in a straight fashion. For illustrative purposes, we will focus on the straight leadwires 12, 14 of FIG. 20, but realize that all of these same principles to follow are equally applicable to twisted or coaxial leadwires as shown in FIG. 19. In FIG. 20, one can see that the insulation sheath 58 generally runs up to and fixates the ring electrode 52, but does not cover or encapsulate it. This is also true for the distal tip electrode 50. This is important such that the electrodes are not insulated, so that they can deliver therapy and/or sense biologic signals. If they were insulated, they would not be able to function and conduct electrical current into body tissue. In practice, the parasitic capacitance value is quite low. For differential mode induced EMFs, by electrically shorting leadwires 12 and 14 together, the energy induced from an MRI system is contained into a loop whereby it will create relatively high RF currents in leadwires 12 and 14. Importantly, this loop disconnects this current flow from the distal electrodes 50 and 52. Accordingly, this energy will be converted to heat within leadwires 12 and 14 where it will be thermally conducted into the insulation sheath 58 and dissipated over a much larger surface area. In the case where the induced EMFs are common mode, frequency selective networks of the present invention are used to conduct the high frequency energy to a metallic surface of the probe or catheter, such as a shield, or to an equivalent energy dissipating surface (EDS). This has the effect of preventing a large temperature rise at the electrode to tissue interface which could be damaging to body tissue. More importantly, said heat is diverted away from the distal electrodes, which make direct contact with sensitive body tissues. It is in this location where excessive heat dissipation can cause temperature rises that can cause damage to body tissue and therefore, undesirable loss of therapy or even life-threatening tissue damage. In a preferred embodiment, the parasitic capacitances or heat conductive interface would be replaced by passive component capacitances that are connected directly to a conductive energy dissipating surface. This is a more efficient way of diverting the energy to a point distant from the distal electrodes and converting it to heat. By re-directing the RF and/or thermal energy to a point or an area distant from the distal electrodes, one thereby provides a high degree of protection to the sensitive junction between the electrodes and body tissue. For example, that junction may be the point where a distal electrode contacts myocardial tissue and provides critically important pacing pulses. Energy concentration at distal electrode can cause dangerous temperature rises.

Figure 21:
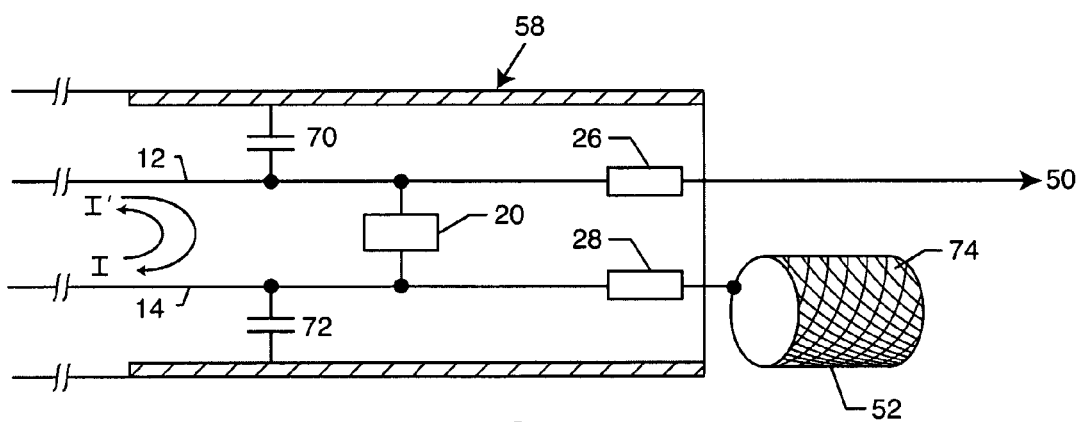
FIG. 21 is similar to FIG. 20 and incorporates electrical features discussed in FIGS. 2-11.

FIG. 21 is generally equivalent and incorporates and embodies the concepts previously described in FIGS. 2 through 11 herein. In FIG. 21, one can see the lead insulation 58. There is a parasitic capacitance 70 and 72 which is formed between leadwires 12 and 14 and the insulation layer 58. At high frequency, this has the desired effect of diverting or shunting high frequency MRI RF energy away from the leadwires 12 and 14 thereby redirecting energy into the insulation sheath 58 where it can be dissipated over a much larger surface area with minimal temperature rise. Series reactive elements 26 and 28, as previously described and shown in connection with FIG. 7, block, cut or impede the flow of MRI induced RF energy to the distal tip electrode 50 and/or the distal ring electrode 52, wherein these electrodes 50, 52 correspond respectively with the ring electrodes 16, 18 shown in FIGS. 2-11. These series frequency selective reactances 26 and 28 are optional, but do increase the efficacy of the present system.

Reactance 20 can be a simple capacitor as shown in FIG. 5, or it can be an L-C series trap filter as shown in FIG. 6. This tends to short leadwires 12 and 14 together at high frequency thereby diverting undesirable high frequency energy and thereby preventing it from reaching distal tip electrode 50 or ring electrode 52. Referring once again to FIG. 21, we can see high frequency RF currents I and I'. These, for example, are the RF pulsed currents induced in an elongated implanted lead from a 1.5 Tesla MRI system, and they would oscillate back and forth at 64 MHz thereby reversing directions, as shown, at that frequency. This is better understood by referring to FIG. 9. The currents are cut off (as indicated at 30 in FIG. 9) and are effectively contained within leadwires 12 and 14. This redirects the energy that is induced by the high frequency MR fields back into the insulation sheath 58 at a point distant from the distal electrodes 50 and 52. This desirably prevents the distal electrodes from overheating at their point of contact with body tissue.

Figure 22:
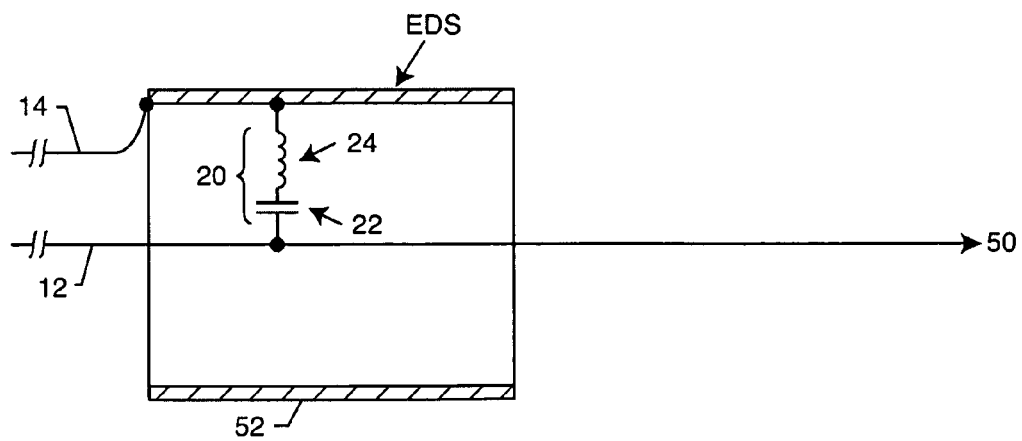
FIG. 22 is similar to a portion of FIGS. 20 and 21, and depicts an L-C trap filter coupled between a distal tip electrode wire and a cylindrical ring electrode.

FIG. 22 is very similar to the structures shown in FIGS. 19 and 20 for active implantable medical devices (AIMDs) such as cardiac pacemakers and the like. Shown is a selective frequency element 20 in accordance with FIG. 6, which in this case consists of an inductor 24 in series with a capacitor 22 (trap filter). The component values of the inductor 24 and the capacitor 22 can be selected such that they are resonant at a particular frequency. In this case, for illustrative purposes, they shall be resonant at 64 MHz thereby providing a low impedance short circuit for 1.5 Tesla MRI signals. This has the effect of diverting or shunting the energy off of leadwire 12 to the relatively large surface area of the ring electrode 52. The ring electrode 52 is typically a metallic structure consisting of a cylindrical ring and very high thermal conductivity. It also has, by necessity, very high electrical conductivity. Accordingly, referring once again to FIG. 22, the ring electrode 52, by its inherent nature, becomes an energy dissipating surface (EDS) wherein the high frequency RF energy is diverted to it, wherein said RF energy will either be converted to heat, which will be directed into the surrounding blood flow, or said RF energy will be harmlessly dissipated into surrounding body tissues. More specifically, for example, in the right ventricle, the distal tip electrode 50 is designed to be screwed into myocardial tissue in accordance with FIGS. 19 and 19A. The ring electrode 52, on the other hand, is designed to be placed back away from distal tip electrode 50 such that it actually floats in the pool of blood that is flowing in the particular cardiac chamber. In an ideal situation, the wash of blood over it tends to provide a constant cooling action through heat transfer over the ring electrode 52 thereby dissipating undesirable heat from high frequency RF energy harmlessly into the flowing blood (or other body fluid such as lymph in other applications). A disadvantage of this approach is that in a certain percentage of patients both the tip and the ring tend to be overgrown by tissue. Accordingly, the use of a separate energy dissipating surface EDS, which is located further back from both the distal tip and ring electrode, is desirable such that it is guaranteed to remain in the blood pool. For the energy dissipating surface EDS, which can either be the ring electrode itself or a separate energy dissipating structure (EDS), it is a desirable feature that it includes some type of biomimetic coating such that tissue overgrowth is inhibited. Referring back to FIG. 21, for example, a biomimetic coating 74 could be deposited all over the ring electrode to thereby inhibit tissue overgrowth.

Figure 23:
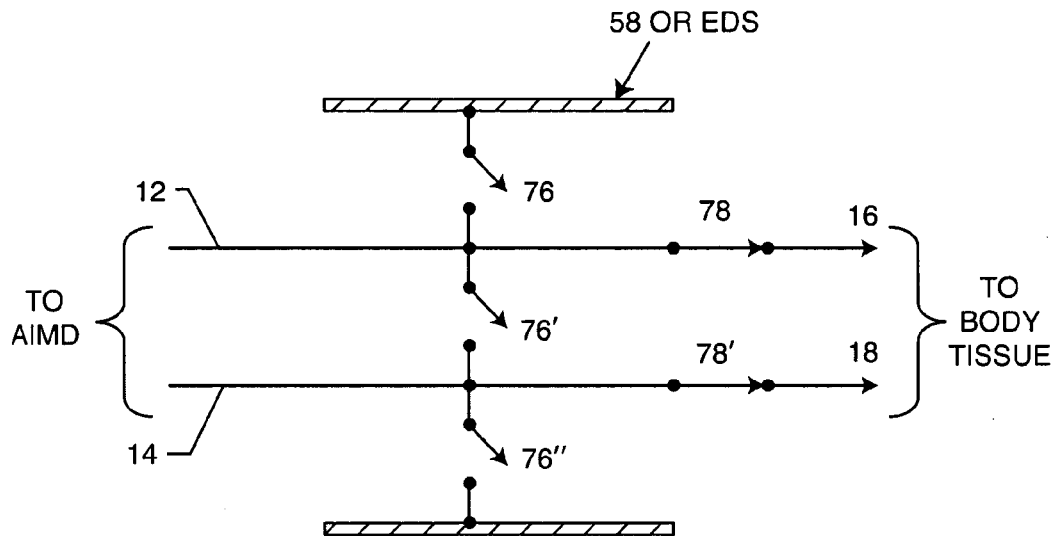
FIG. 23 is a schematic low frequency model illustration operation of the embodiment depicted generally at FIGS. 7-8.

FIG. 23 is a low frequency model illustrating the concepts previously shown and described in connection with FIG. 7. Switches are used to illustrate the properties of the reactances at low frequency. Referring back to FIGS. 21-22, one can see that there is an insulation sheath 58 or energy dissipating surface EDS. The parallel reactance element 20, as illustrated in FIGS. 4, 5 and 6, is represented respectively by switches 76, 76' and 76". At low frequency, these reactances tend to look like very high impedances and are therefore shown as open switches. On the other hand, the series reactances 26 and 28, as previously illustrated and described in FIGS. 7, 10 and 11, tend to look like a very low impedance approximating short circuits at low frequency and are thus shown respectively as closed switches 78 and 78'. Accordingly, the low frequency model, as illustrated in FIG. 23, is completely equivalent to the low frequency model previously shown and described in connection with FIG. 8. In this case, the reactive elements 20, 26 and 28 effectively disappear from the electrical model, whereby the pair of electrodes 12, 14 is coupled directly and respectively to the pair of electrodes 16 and 18.

Figure 24:
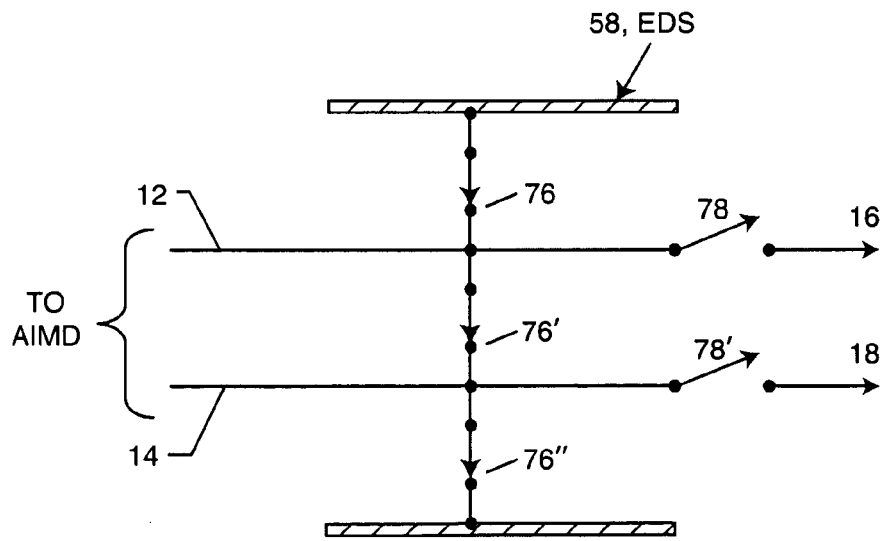
FIG. 24 is a schematic diagram similar to FIG. 23, but shows a high frequency model of the embodiment depicted generally at FIGS. 7 and 9.

FIG. 24 is the high frequency model of FIG. 7. In this case, the reactance element 20, previously illustrated in FIGS. 4, 5 and 7, tends to look like a very low impedance at high frequency and therefore, is represented as a closed switch (or short circuit) as shown by switches 76, 76', and 76". In FIG. 24, one can see that the series reactance components 26, 28 of FIGS. 7, 10 and 11 look like very high impedances (ideally open circuits) at high frequency and are thereby shown as open switches 78 and 78'. Therefore, the high frequency model, as illustrated in FIG. 24, is completely equivalent to the high frequency model previously described and shown in connection with FIG. 9. Of course, these switches do not really physically exist and are simply a way of illustrating the behavior of the passive component frequency selective networks that are described in FIGS. 4 through 11.

Figure 25:
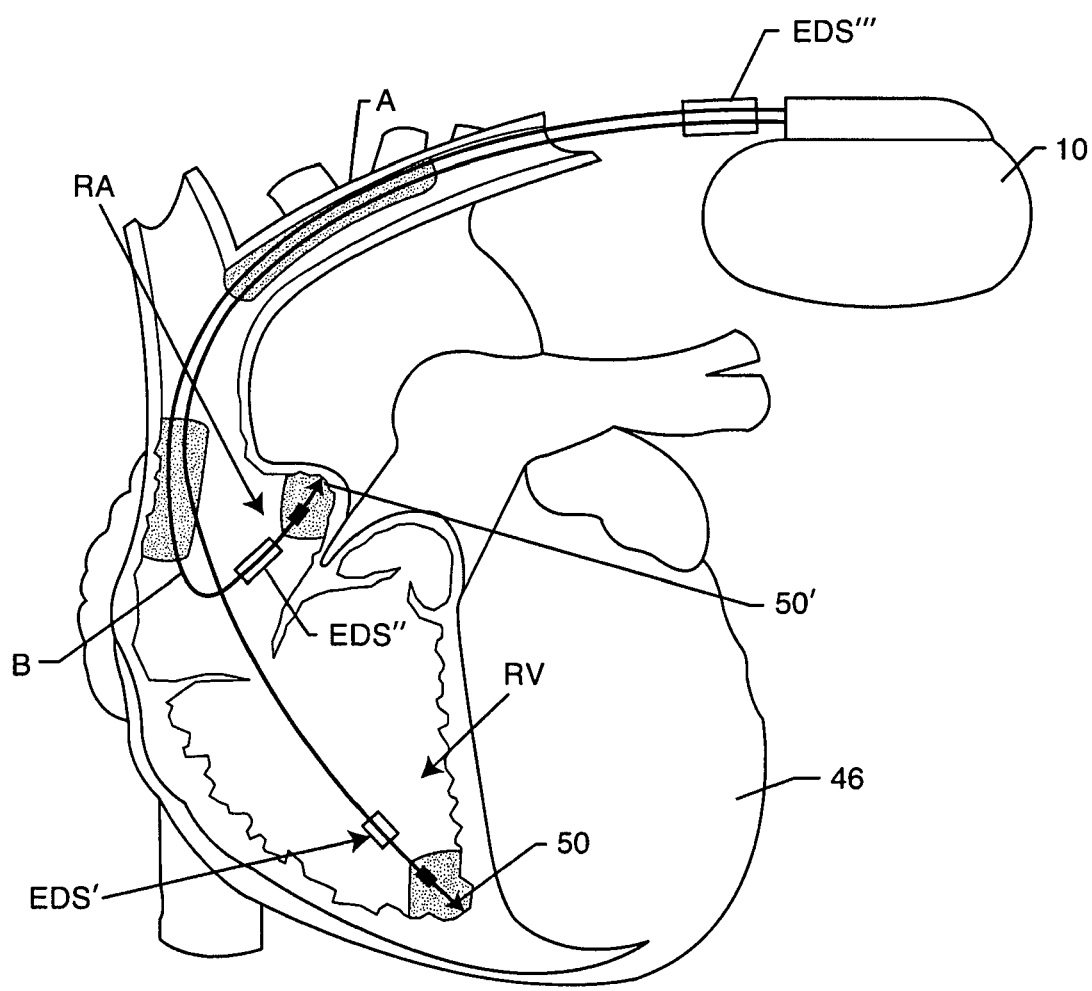
FIG. 25 is a line drawing of a human heart with cardiac pacemaker dual chamber bipolar leads shown in the right ventricle and the right atrium.

FIG. 25 is a line drawing of a human heart with cardiac pacemaker dual chamber bipolar leads shown in the right ventricle RV and the right atrium RA of a human heart 46. FIG. 25 is taken from slide number 3 from a PowerPoint presentation given at The 28th Annual Scientific Sessions of the Heart Rhythm Society by Dr. Bruce L. Wilkoff, M. D. of the Cleveland Clinic Foundation. This article was given in Session 113 on Friday, May 11, 2007 and was entitled, ICD LEAD EXTRACTION OF INFECTED AND/OR REDUNDANT LEADS. These slides are incorporated herein by reference and will be referred to again simply as the Wilkoff reference. In FIG. 25, one can see multiple leadwires extending from an active implantable medical device 10 (such as a pacemaker or the like) coupled to associated electrodes, one of which comprises the distal tip ventricular electrode 50 located in the right ventricular (RV) apex. The dark shaded areas in FIG. 25 show the experience of the Cleveland Clinic and Dr. Wilkoff (who is a specialist in lead extraction), where extreme tissue overgrowth and vegetation tends to occur. There are numerous cases of extracted leads where both the tip and ring electrodes have been overgrown and encapsulated by tissue. Referring once again to FIG. 25, one can see tip electrode 50, which is located in the right ventricular apex. The shaded area encasing this electrode 50 shows that this area tends to become encapsulated by body tissue. An electrode 50' in the right atrium (RA) may similarly be overgrown and encapsulated by tissue, as shown by the encasing shaded area. There are other areas in the aortic arch and venous system where leads tend to be encapsulated by body tissue a great percentage of the time. These are shown as areas A and B. This is particularly important to know for the present invention since these would be highly undesirable areas to place an energy dissipating surface in accordance with the present invention. Ideal locations for energy dissipating surfaces are shown as EDS' and EDS" or EDS'''.

Referring once again to FIG. 25, as previously mentioned, it is very important that this leadwire system does not overheat during MRI procedures particularly at or near the distal tip electrodes and rings. If both the distal tip and ring electrode become overgrown by body tissue, excessive overheating can cause scarring, burning or necrosis of said tissues. This can result in loss of capture (loss pacing pulses) which can be life-threatening for a pacemaker dependent patient. It is also the case where implanted leads are often abandoned (where the lead has been permanently disconnected from the AIMD). Often times when the device such as a pacemaker 10 shown in FIG. 25 is changed out, for example, due to low battery life and a new pacemaker is installed, the physician may decide to install new leadwires at the same time. Leadwires are also abandoned for other reasons, such as a dislodged or a high impedance threshold. Sometimes over the course of a patient life-time, the distal tip electrode to tissue interface increases in impedance. This means that the new pacemaker would have to pulse at a very high voltage output level which would quickly deplete its battery life. This is yet another example of why a physician would choose to insert new leads. Sometimes the old leads are simply extracted. However, this is a very complicated surgical procedure which does involve risks to the patient. Fortunately, there is plenty of room in the venous system and in the tricuspid valve to place additional leads through the same pathway. The physician may also choose to implant the pacemaker on the other side. For example, if the original pacemaker was in the right pectoral region, the physician may remove that pacemaker and choose to install the new pacemaker in the left pectoral region using a different part of the venous system to gain lead access. In either case, the abandoned leads can be very problematic during an MRI procedure. In general, abandoned leads are capped at their proximal connector points so that body fluids will not enter into the lead system, cause infections and the like. However, it has been shown in the literature that the distal electrodes of abandoned leads can still heat up during MRI procedures. Accordingly, a passive frequency selective circuit of the present invention is very useful when placed at or near the proximal electrical contact after a pacemaker is removed and its leads are disconnected (abandoned). For example, for an abandoned (left in the body) lead, an energy dissipating surface EDS''' at or near the proximal lead end is an ideal place to eliminate excess energy induced by MRI in the leadwire system.

Referring back to the article by Dr. Bruce Wilkoff, attention is drawn to slide number 2, which is an example of a lead extraction showing both a distal tip electrode and a distal ring which have been heavily overgrown and encapsulated by body tissue. Special cutting tools were used to free the lead so it could be extracted, so the tissue shown here is only a small remaining portion of the mass that was originally present. Slide 13 is a dramatic illustration of what a larger mass of encapsulated tissue would look like. In this case, the entire tip was completely surrounded, but if one looks carefully to the right, one can see that some of the ring was still exposed. The situation is highly variable in that the ring is not always fully encapsulated. Slide 16 is an example of tissue removal after a pacemaker bipolar lead was extracted. One can see at the end of the lead, the helix screw that was affixed to myocardial tissue. The surgeon in this photo was removing the tissue encapsulation, which completely surrounded the tip and is still surrounding the ring area. A blow-up of this is shown in slide 17. Again, the tissue that is still affixed to the lead has completely encapsulated the ring, which cannot be seen. Accordingly, there is a need for either a way to prevent the overgrowth of body tissue onto the ring or to ensure that an energy dissipating surface (EDS) is located far enough away from myocardial tissue to guarantee that it will remain floating in the blood pool.

Figure 26:
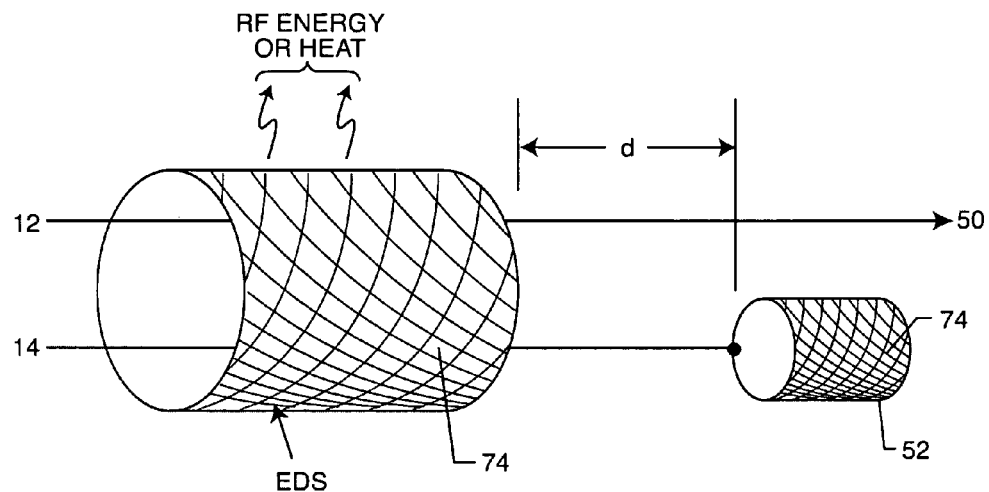
FIG. 26 is a schematic diagram illustration an energy dissipating surface in spaced relation with tip and ring electrodes.

FIG. 26 illustrates an energy dissipating ring EDS which is located at some distance "d" from both a pacemaker tip electrode 50 and a ring electrode 52 mounted respectively at the distal ends of leadwires 12 and 14. The distance "d" should be sufficient so that the energy dissipating surface EDS is far enough away from both the distal tip and ring electrodes 50, 52 such that there is no heating or temperature rise associated with the tissues that contact the tip and ring electrodes. Another advantage of moving the energy dissipating surface EDS away from the distal electrodes, particularly for a cardiac pacemaker application, is that there would be less tendency for the energy dissipating surface EDS to become encapsulated or overgrown with vegetated body tissue. If the energy dissipating surface EDS, when it is disassociated at some distance from the electrodes 50, 52, does become overgrown with body tissue, this is not of great concern. Obviously, it would be superior to have the EDS surface floating in freely flowing blood so that there would be constant cooling. However, for example, if the EDS surface did touch off to the right ventricular septum and became overgrown, the only effect would be a slight heating of tissue in an area that is far away from where the actual electrical stimulation and sensing is being done by the electrodes. The ideal distance for the energy dissipating surface does depend on the particular application and ranges from approximately 0.1 cm to 10 cm distance from the distal electrodes.

Referring once again to FIG. 26, the energy dissipating surface EDS is shown as a cylindrical ring. It can be semicircular, rectangular, octagonal, hexagonal or even involve semi-circles on the lead or any other metallic or similar structure that is also thermally conductive. Literally any shape or geometry can be used as an energy dissipation surface. It is a desirable feature of the present invention that the surface area be relatively large so that it can efficiently dissipate heat into the surrounding blood pool and surrounding tissues that are distanced from the electrodes. In FIG. 26, within the EDS ring, there are electrical connections (not shown) between leadwire 12 and 14 and to the EDS surface that embody the passive frequency selective circuits previously discussed in connection with FIGS. 2 through 11. The purpose of these frequency selective circuits is to remove RF induced energy caused by the RF pulsed field of MRI from leadwires 12 and 14 and redirect it to the EDS surface where it is dissipated as heat. By having a large surface area, the heat can be dissipated without significant temperature rise such that surrounding tissues would be burned.

In cardiac rhythm management applications, the EDS ring is ideally located in areas where there is freely flowing blood, lymph or equivalent body fluids which adds to the cooling. A biomimetic coating 74 can be applied to the energy dissipating surface area (EDS) and/or to the ring electrode 52 if it is used as an energy dissipating surface. This special biomimetic coating 74 provides a non-thrombogenic and anti-adhesion benefits. This coating can be comprised of a surfactant polymer having a flexible polymeric backbone, which is linked to a plurality of hydrophobic side chains and a plurality of hydrophilic side chains. This coating prevents the adhesion of certain plasma proteins and platelets on the surface and hence initiation of the clotting cascade or colonization of bacteria. Biomimetic coatings also tend to prevent overgrowth or adhesion of body tissues as illustrated in the Wilkoff paper. This polymer compound is described in U.S. Pat. Nos. 6,759,388 and 7,276,474, the contents of both patents being incorporated by reference herein. Additional benefits of biomimetic coatings include the prevention of bacterial colonization and resulting infections. It will be obvious to those skilled in the art that other types of coatings could be used on the EDS ring to inhibit or prevent overgrowth of body tissue. As used herein, the term biomimetics includes all such type coatings.

Figure 27:
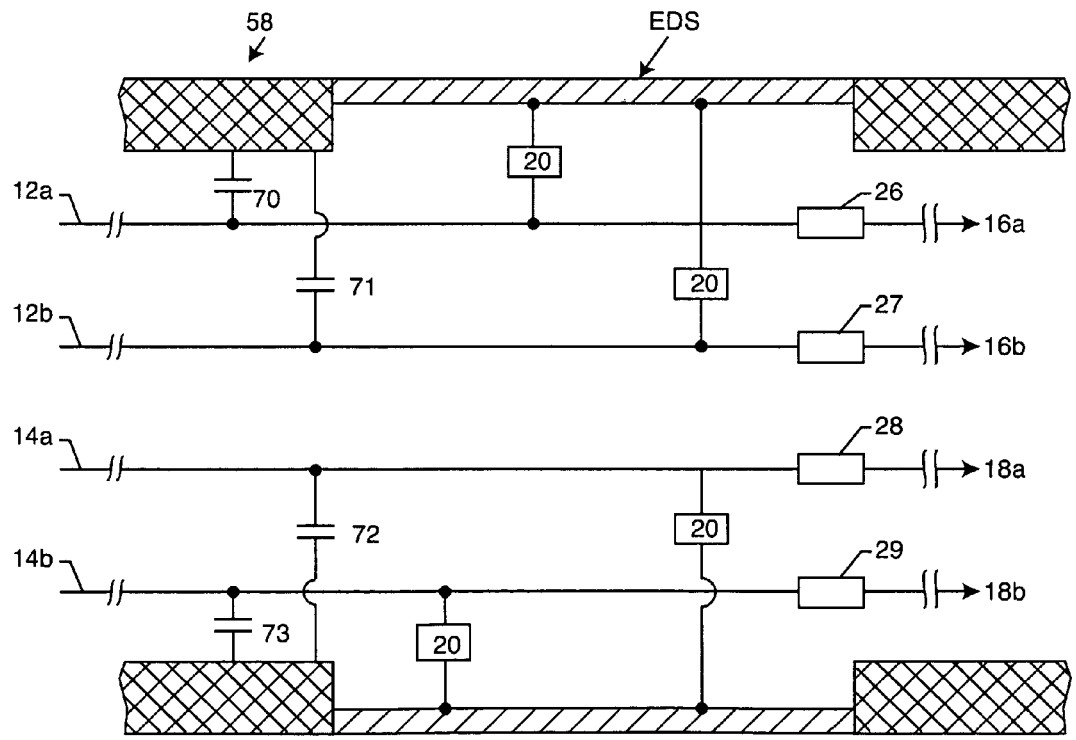
FIG. 27 a schematic diagram depicting a typical quad polar neurostimulation lead system.

FIG. 27 is a typical quad polar neurostimulation lead system. It will be appreciated that the following discussion also applies to bipolar, hex polar, and even 16 or 24 electrode lead systems. In FIG. 27, four leadwires 12, 12b, 14a and 14b are shown which are each directed respectively toward an associated distal electrode 16a, 16b, 18a and 18b. In this case, the electrical stimulation pulses are applied in various combinations between the various electrodes. Unlike a cardiac pacemaker application, there is no particular ring electrode in this case. However, the insulation sheath 58 that surrounds the leadwires, which as mentioned could be of silicone or the like, forms a surrounding surface, which encapsulates the leadwires.

Parasitic capacitances 70, 71, 72 and 73 are formed respectively between each of the leadwires 12a, 12b, 14a and 14c and the insulating sheath 58. As previously mentioned, these parasitic capacitances can divert high frequency pulsed RF energy from an MRI system to the insulation sheath 58 thereby redirecting the energy so that heat will be dissipated over a larger surface area and away from the interface between the distal tip electrodes 16a, 16b, 18a, and 18b and body tissue. There is also heat that is directly dissipated off of the leadwires, which is conductively coupled into the insulation sheath 58. Again, it is desirable that this occur at a location that is spaced from or distant from the therapy delivery electrodes 16a, 16b, 18a, and 18b. This can be greatly improved by providing a passive component frequency selective circuit 20 which provided a very low impedance at a selected high frequency or frequencies between each of the associated leadwires and an energy dissipating surface EDS. The energy dissipating surface EDS would typically either be a metallic ring or a metallic plate or even a separated metallic surface which has both the property of conducting the high frequency energy and also having a relatively large surface area for dissipating said energy into surrounding body tissues. In a preferred embodiment, the energy dissipating surface EDS would be placed sufficiently far back from the distal electrodes 16a, 16b, 18a, and 18b so that in the associated heating of surrounding body tissue would not have any effect on the delicate electrode-to-tissue interface. In addition, by having an energy dissipating surface (EDS) with a sufficiently large surface area, this will prevent a dangerously large temperature rise as it dissipates energy into the surrounding tissues. By controlling the temperature rise to a small amount, damage to tissue or tissue changes are therefore avoided. The frequency selective reactances 20 are designed to present a very low impedance at selected high frequencies thereby redirecting undesirable high frequency RF energy (in the MHz range) away from the electrodes to the insulating sheath and/or energy dissipating surface (EDS). In addition, further protection is offered by the optional series frequency selective components 26, 27, 28 and 29. Typically, these can be series inductors or they can be parallel inductor-capacitor bandstop filters in accordance with the present invention (see FIGS. 10-11). Accordingly, substantial protection is provided such that during MRI procedures, the distal electrodes 16a, 16b, 18a, . . . 18$_n$ do not overheat.

Figure 28:
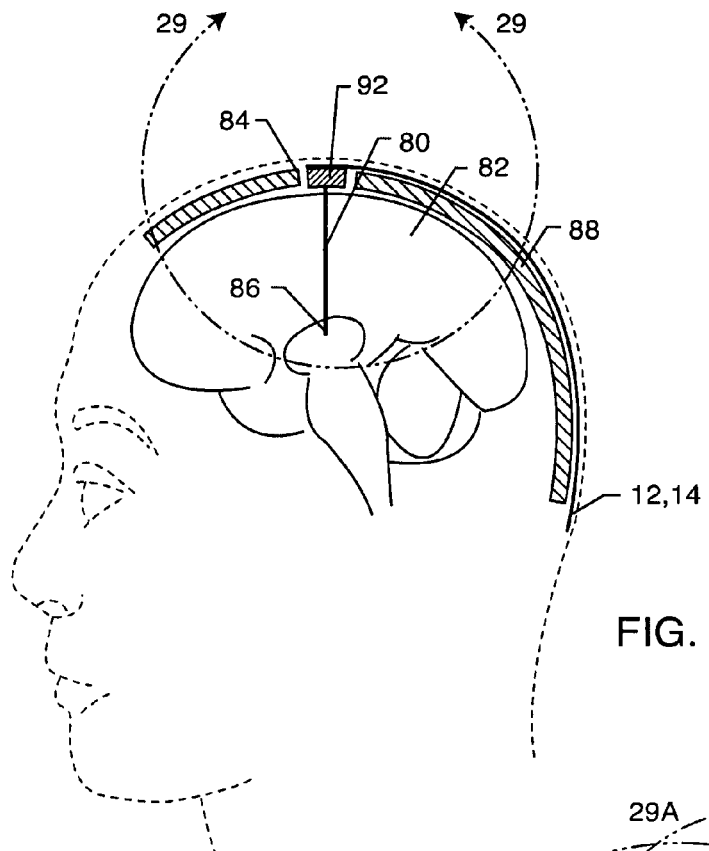
FIG. 28 is a somewhat schematic side view of the human head with a deep brain stimulation electrode shaft assembly implanted therein.

FIG. 28 is taken from FIG. 13 of U.S. 2008/0132987 A1 dated Jun. 5, 2008, the contents of which are incorporated herein by reference. Illustrated is a side view of the human head with a deep brain stimulation electrode shaft assembly 80. At the distal end of the electrode shaft 80 are two distal electrodes 16 and 18 (see FIG. 29) implanted into the patient's brain 82 at a selected implantation site. One or more leadwires 12, 14 (see FIG. 29A) are routed between the skin 87 and the skull 88 down to a pectorally implanted AIMD (pulse generator) which is not shown. Referring back to FIG. 28, one can see that an opening 84 in the skull has been made so that the electrode shaft assembly 80 can be inserted.

Figure 29:
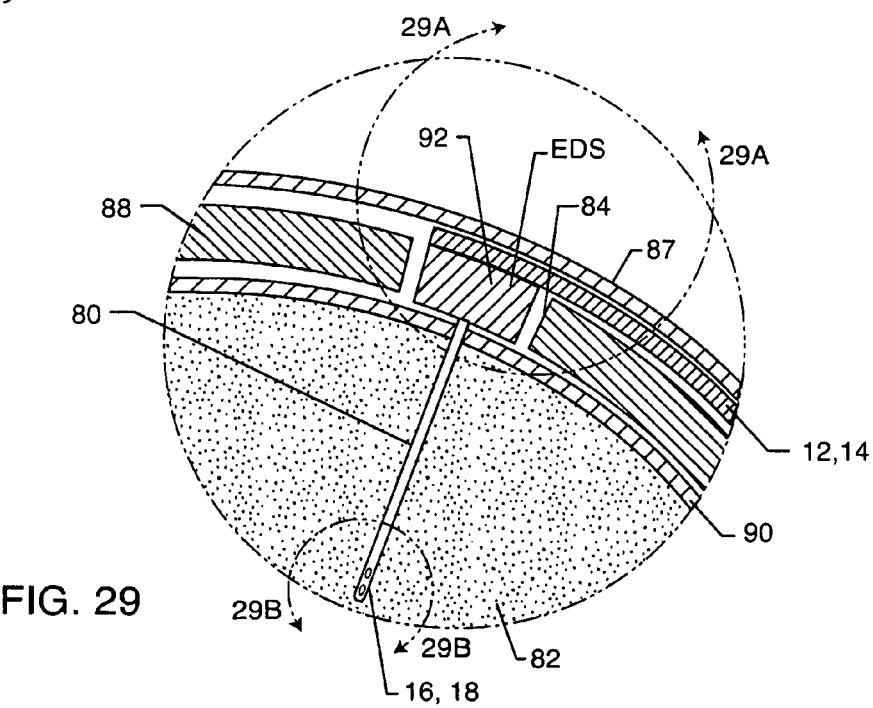
FIG. 29 is an enlarged sectional view corresponding generally with the encircled region 29-29 of FIG. 28.

FIG. 29 is taken generally from section 29-29 in FIG. 28. Shown are bipolar distal electrodes 16 and 18 at the end or tip 86 of the electrode shaft 80. The skull is shown at 88 and the dura is shown as 90. Housing 92 acts as an energy dissipating surface EDS and can be hermetically sealed to protect the passive frequency selective components of the present invention from direct exposure to body fluids.

Figure 29A:
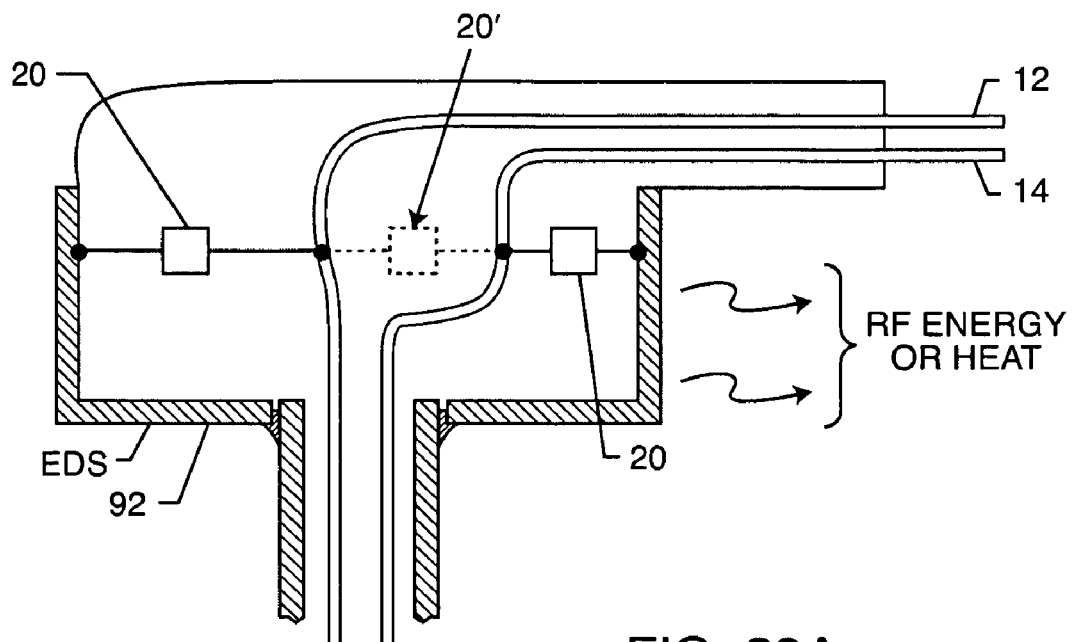
FIG. 29A is a further enlarged and somewhat schematic view corresponding generally with the encircled region 29A-29A of FIG. 29.

FIG. 29A is taken from section 29A-29A of FIG. 29. Shown are frequency selective passive component circuit elements 20 which are generally taken from FIG. 5 or 6. As previously described, these circuit elements 20 could be combined with series reactance elements 26 and 28 as previously illustrated in FIGS. 7, 10 and 11. These have been omitted for clarity, but would generally be placed in series with the leadwires 12 and 14 and placed between frequency selective circuit elements 20 and the distal electrodes 16, 18 (FIG. 20). Referring back to FIG. 29A, circuit elements 20 would divert high frequency RF energy induced from an MR scanner to the energy dissipating surface EDS where it would be dissipated as RF or thermal energy into the area of the skull 88 and/or dura 90. Frequency selective circuit element 20' is also shown connected between the leadwires 12 and 14. This would be effective for any differential mode signals that are present in the leadwires 12 and 14. In accordance with FIG. 4 of the present invention, this would redirect or divert MRI induced RF energy back into leadwires 12 and 14 and away from the distal electrodes 16, 18. This is an example of redirecting RF or thermal energy away from a critical tissue interface point. The skull is considered to be a relatively non-critical or less susceptible type of body tissue to thermal injury. This is in comparison with the very thermally sensitive brain matter into which the distal tip electrodes 16, 18 are implanted. It has been shown that even a temperature rise as small as a few degrees C. can cause damage to sensitive brain matter.

Figure 29B:
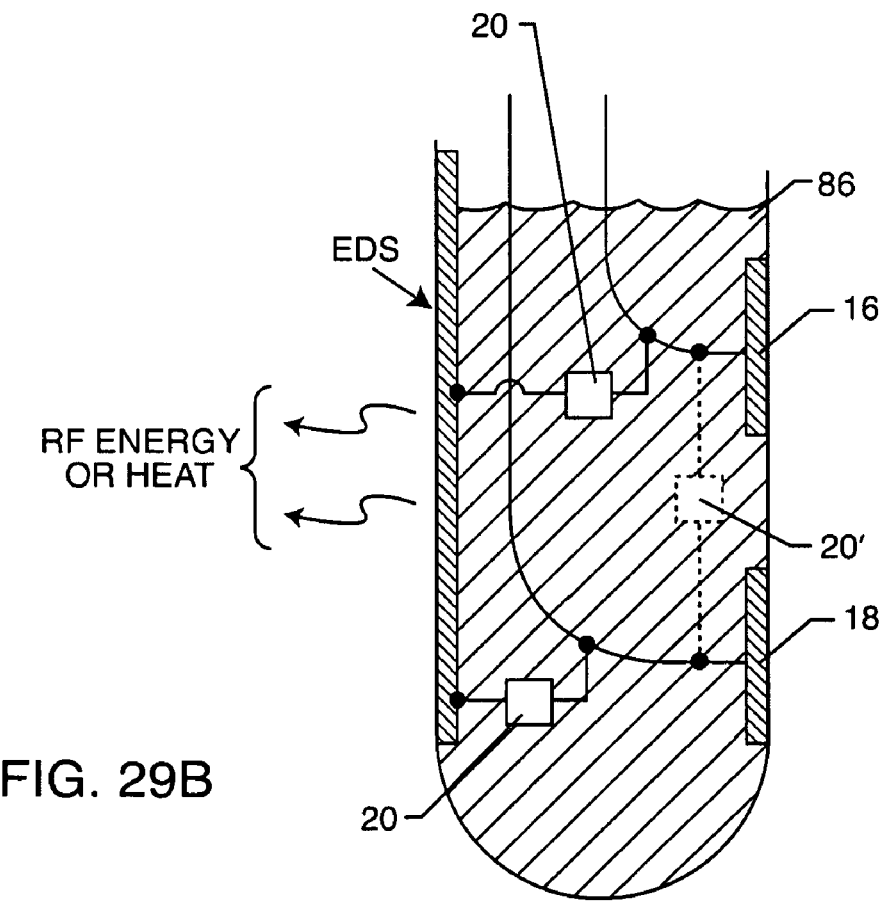
FIG. 29B is an enlarged and somewhat schematic view corresponding generally with the encircled region 29B-29B of FIG. 29.

FIG. 29B is generally taken from area 29B-29B of FIG. 29. Shown are the two bipolar electrodes 16 and 18. The frequency selective elements 20 and 20' have been moved relative to the location shown in FIG. 29A to illustrate one wrong way to approach this particular problem. Specifically, an energy dissipating surface EDS is shown mounted generally at a tip or other distal end portion of the probe shaft 86 in proximity to and/or direct contact with sensitive brain tissue. The frequency selective reactance components 20 and 20' are coupled for redirecting the RF energy from MRI to the energy dissipating surface EDS, whereby heat will be dissipated by the energy dissipating surface EDS. In the case where it was chosen not to use an energy dissipating surface EDS, but simply to rely on the line-to-line frequency selective element 20', heat would still build-up in the entire distal electrode area and thence be conducted into thermally sensitive brain tissue 82. Accordingly, the placement of the circuit elements as shown in FIG. 29B illustrates a disastrous way to place the frequency selective elements of the present invention. Severe overheating of this distal tip would occur with resulting brain damage. Reference is made to a paper given at the 8$^{th}$ World Congress of the National Neuromodulation Society which was held in conjunction with the 11$^{th}$ Annual Meeting of the North American Neuromodulation Society, Dec. 8-13, 2007, Acapulco, Mexico. This paper was given by Dr. Frank Shellock, Ph. D. and was entitled, MRI ISSUES FOR NEUROMODULATION DEVICES.

Shellock slide 31 shows X-ray views of the placement of deep brain stimulator electrodes into the skull and brain of a human patient. There is also an X-ray view showing the placement of the AIMDs and tunneled leadwires that are associated with the deep brain stimulation electrodes. Slide number 35 shows an extensive thermally induced lesion shown in white with a red arrow to it. This was representative of two patients that inadvertently received MRI wherein their deep brain stimulators overheated and caused extensive thermal injury to the brain. Both patients were severely disabled.

In summary, the configuration as illustrated in FIG. 29A is highly desirable as compared to the configuration as illustrated in FIG. 29B.

Referring once again to the Shellock paper, one can see that the deep brain stimulator involved multiple electrodes. In FIG. 29 one can see that there are only two electrodes 16 and 18. This is a way of illustrating that with real time MRI guidance, the physician can much more accurately place the electrodes into the exact area of the brain, which needs to be electrically stimulated (for example, to control Parkinson's tremor, Turret's Syndrome or the like). What is typically done is that precise MR imaging is performed prior to electrode implantation which is referenced to fiducial marks that's placed on the skin in several locations outside of the patient's skull. The patient's head is first shaved, then these marks are placed and then the MRI is performed. Then when the patient enters the operating room, a fixture is literally screwed to the patient's head at these fiducial marks. This fixture contains a bore into which the various drilling and electrode implanting tools are located. Because of the need for all of this mechanical fixturing, tolerances are involved. This means that by the time the electrodes are implanted in the brain, they may be not in the precise locations as desired. Accordingly, extra electrodes are inserted which involves more leadwires than are really necessary. The patient is usually awake during parts of this procedure wherein the physician will use trial and error to stimulate various electrode pairs until the desired result is achieved. In contrast, the present invention minimizes the need for all these extra electrodes and extra wiring. This is because by eliminating the potential for the distal electrodes to overheat and damage brain tissue, this entire procedure can be done under real time MRI imaging. In other words, the physician can be watching the MRI images in real time as he precisely guides the electrodes to the exact anatomy of the brain that he wishes to stimulate.

FIG. 30 is a hermetically sealed package consisting of a passive distal tip electrode 50 which is designed to be in intimate contact with body tissue, such as inside the right atrium of the heart. A hermetic seal is formed at laser weld 94 as shown between the tip electrode 50 and a metallic ring 96. Gold brazes 98 are used to separate the metallic ring 96 from the energy dissipating surface EDS by use of an intervening insulator 100. This insulator 100 could typically be of alumina ceramic, other types of ceramic, glass, sapphire or the like. The energy dissipating surface EDS is typically gold brazed to the other side of the insulator 100 as shown. An inductor 26', such as an inductor chip in accordance with FIG. 10, is shown connected between the distal tip electrode 50 and a conductive lead 102 which is attached as by laser welds 104 to the end of the leadwire 12 extending through the body to the AIMD. As shown, the lead 102 protrudes through a hermetic seal assembly 106 formed by a metallic flange 108 which is typically of titanium or platinum or the like. The flange 108 is hermetically attached to the lead 102 as by gold brazes 110, and is typically laser welded as shown at 112 to a proximal end of the energy dissipating surface EDS.

FIG. 31 is taken generally from the housing of FIG. 30. It is important that the electrical insulating material 100 either be of very low thermal conductivity or have a relatively long length "L" as shown. The reason for this is that the thermal energy that is developed in the energy dissipating surface EDS must not be allowed to reach the distal tip electrode 50 as shown in FIG. 30 where heat could cause damage to the adjacent tissue.

The energy dissipating surface EDS is typically of biocompatible metals, such as titanium, platinum or the like. It is important that the energy dissipating surface be both electrically conductive and thermally conductive so that it can transfer RF and thermal energy into body fluid or tissue. The energy dissipating surface EDS can be roughened or even corrugated or bellowed as shown in FIG. 31A to increase its surface area and therefore its energy dissipating properties into surrounding body fluids or body tissue.

In accordance with FIG. 5, capacitive elements 22 and 22' shown in FIG. 30 are designed to act as a low impedance at higher frequencies. Electrical connections 114 and 116 (FIG. 30) couple the capacitor 22 to the energy dissipating surface EDS, whereas electrical connections 118 and 120 couple the capacitor 22' to the energy dissipating surface EDS. This forms a broad band low pass filter wherein the inductor 26' acts in cooperation with the capacitive elements 22 and 22'. The presence of the inductor element 26' is not required; however, it does enhance the performance of the capacitor elements 22 and 22'. Capacitor elements 22 and 22' are typical off-the-shelf commercial monolithic ceramic capacitors (MLCCs). These are better illustrated in FIG. 33A.

There is an advantage in the present invention in using a capacitor for the selective frequency element 20 as shown in FIG. 5. The capacitor tends to act as a broadband filter which will attenuate a range of MRI frequencies. For example, placement of an effective capacitor 20 could attenuate 64 megahertz, 128 megahertz and higher MRI frequencies. However, if one were to use an L-C series trap filter as shown in FIG. 6 for the variable frequency element 20, then this would only be effective at one MRI frequency, for example, 64 megahertz only. Of course, as already been disclosed herein, one could use multiple L-C trap filters. However, in a preferred embodiment the use of a capacitor as illustrated in FIG. 5 is desirable because with a single component, one can attenuate a broad range of MRI frequencies.

The schematic diagram for the circuitry of FIG. 30 is shown in FIG. 32. Capacitors 22 and 22' are actually in parallel and act as a single capacitive element. The reason for multiple capacitors is to obtain a high enough total capacitance value so that the capacitive reactance is very low at the frequency of interest (for example, 64 MHz for a 1.5 T MR system).

An alternative capacitor 22" for use in the circuit of FIG. 32 is known as a unipolar feedthrough capacitor is shown in FIG. 33B. It has outside diameter and inside diameter termination surfaces 124 and 122 for electrical contact. Feedthrough capacitors can be unipolar or multipolar. These are completely described in the prior art; for example, refer to U.S. Pat. No. 7,363,090, particularly FIGS. 3, 5, 29 through 31, and 39. See also U.S. Pat. Nos. 4,424,551; 5,333,095; and 6,765,779.

Figure 34:
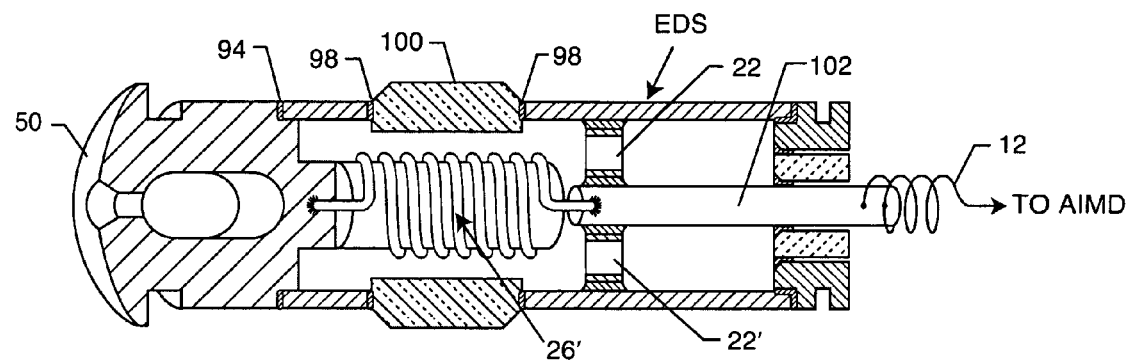
FIG. 34 is a sectional view similar to FIG. 30 and depicts an alternative embodiment wherein an inductor element is wound or printed about a central mandrel.
Figure 42:
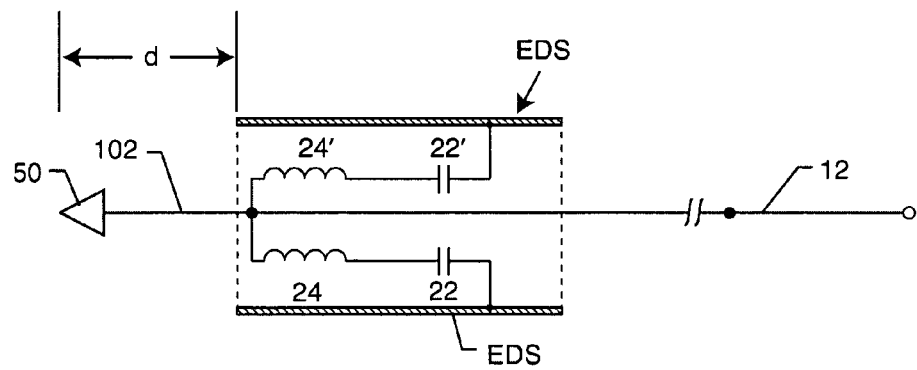
FIG. 42 is a schematic circuit diagram corresponding with the sealed electrode assembly of FIG. 41.
Figure 46:
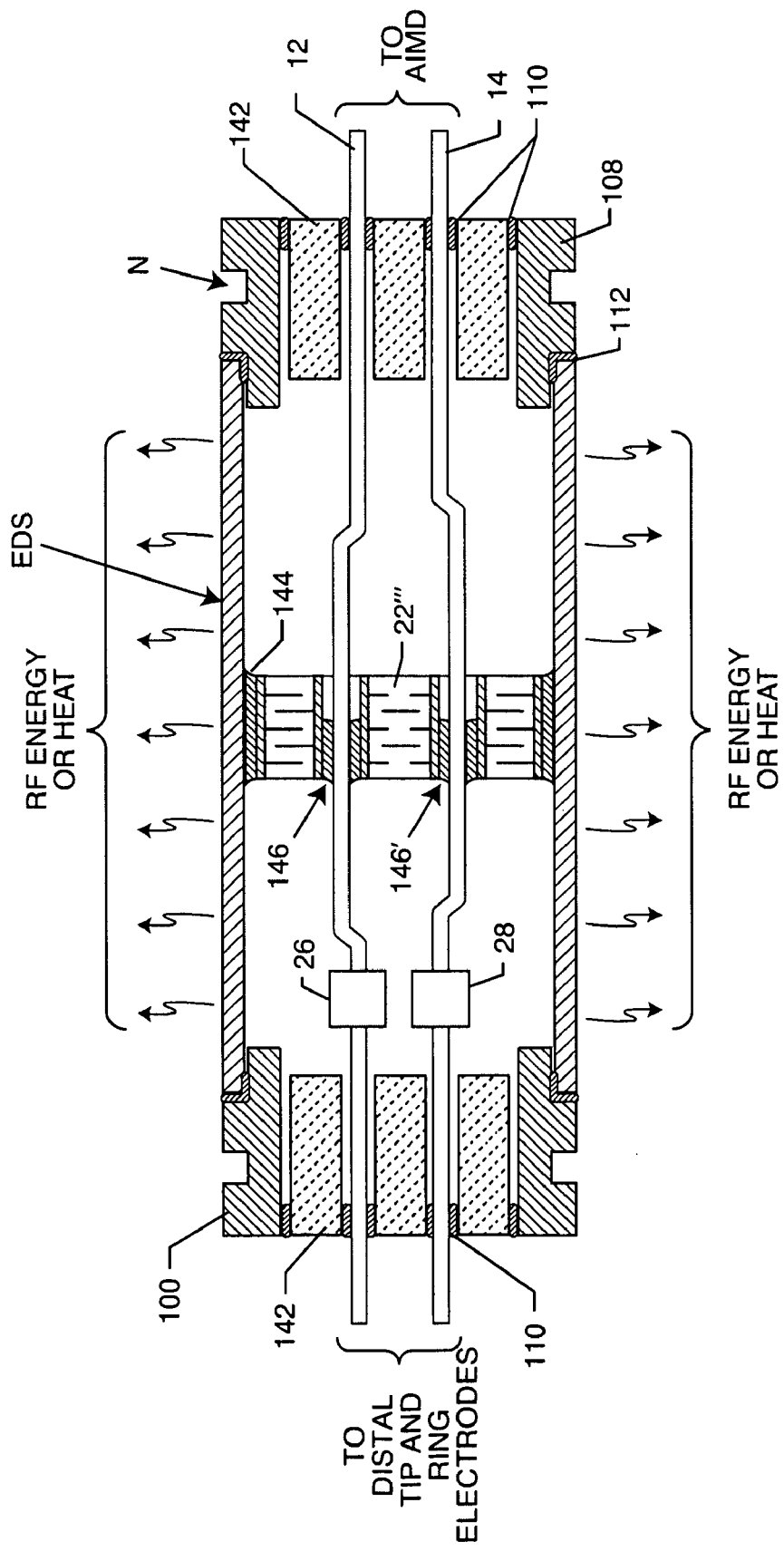
FIG. 46 is an enlarged and somewhat schematic sectional view taken generally on the line 46-46 of FIG. 45.

FIG. 34 is similar to FIG. 30 (using common reference symbols) except that the inductor element 26' is wire wound around a non-ferromagnetic mandrel 126 (formed from a material such as a ceramic or plastic). This type of wound inductor 26' has much higher current handling capability as compared to the inductor chip of FIG. 30. The inductor chip of FIG. 30 can be fabricated from a variety of shapes including Wheeler's spirals and the like. Refer to U.S. Patent Publication No. 2007-0112398 A1, FIG. 83. A Wheeler's spiral is illustrated in FIGS. 42 and 43 of U.S. Patent Application No. 60/767,484. A composite inductor is illustrated in FIG. 46 of U.S. Patent Application No. 60/767,484. Also refer to FIGS. 70 and 71 of U.S. Patent Application No. 61/038,382. These inductors can be manufactured by a number of printing techniques including lithographic or copper clouting and etching. However, this results in relatively thin and high resistivity inductor traces.

It is important that the inductor element 26' of the present invention be able to handle substantially high currents when it is in series with the lead 102. The reason for this has to do with either ICD applications for shock electrodes or automatic external defibrillation (AED) events. AEDs have become very popular in government buildings, hospitals, hotels, and many other public places. When the external defibrillator paddles are placed over the chest of a cardiac pacemaker patient, the high voltage that propagates through body tissue can induce powerful currents in implanted leads. Accordingly, the inductor 26' of the present invention has to be designed to handle fairly high current (as high as the 4 to 8 amp range in short bursts). The wire wound inductor 26' of FIG. 34 has wire of a larger cross-sectional area and is therefore a higher current handling inductor and is therefore a preferred embodiment.

Figure 35:
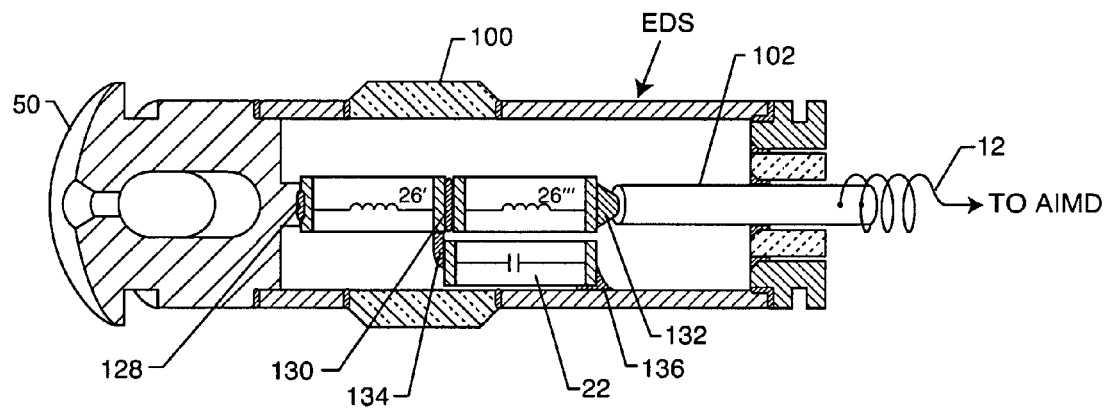
FIG. 35 is a sectional view similar to FIGS. 30 and 34, but illustrates a further alternative embodiment of the invention with alternative means for decoupling signals from a leadwire to an energy dissipating surface.

FIG. 35 illustrates an entirely different approach for the diverting of RF energy away from the electrode tip DT to the energy dissipation surface EDS. Shown are electrical connections 128, 130 between a first inductor 26' and the distal tip electrode assembly 50. The other end of the first inductor 26' is connected to a second inductor 26''' which is in turn electrically connected at 132 to the leadwire 102. The capacitor 22 is connected between the junction of the two inductors 26' and 26''' at electrical connection 134. The other end of the capacitor is electrically connected at 136 to the energy dissipating surface EDS. An insulating sleeve (not shown) can be used to ensure that the capacitor termination and electrical connection 134 does not inadvertently make contact (short out) with the energy dissipating surface EDS. As shown, this connection is made adjacent to the insulator 100 so there is no chance for such shorting out.

Figure 36:
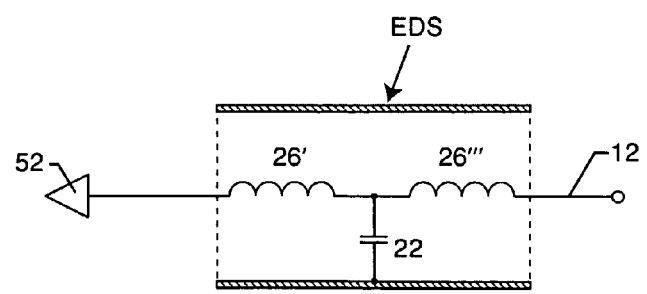
FIG. 36 is a schematic circuit diagram corresponding with the sealed electrode assembly of FIG. 35.

The electrical schematic for FIG. 35 is shown in FIG. 36. In accordance with FIG. 7, this forms what is known in the art as a low pass filter (in this example, a T filter), which tends to enhance the filtering performance by directing more of the RF energy to the energy dissipating surface EDS. As previously mentioned, a single or multi-element low pass filter would attenuate a broad range of MRI frequencies and would be an advantage in the present invention for that reason.

Figure 37:
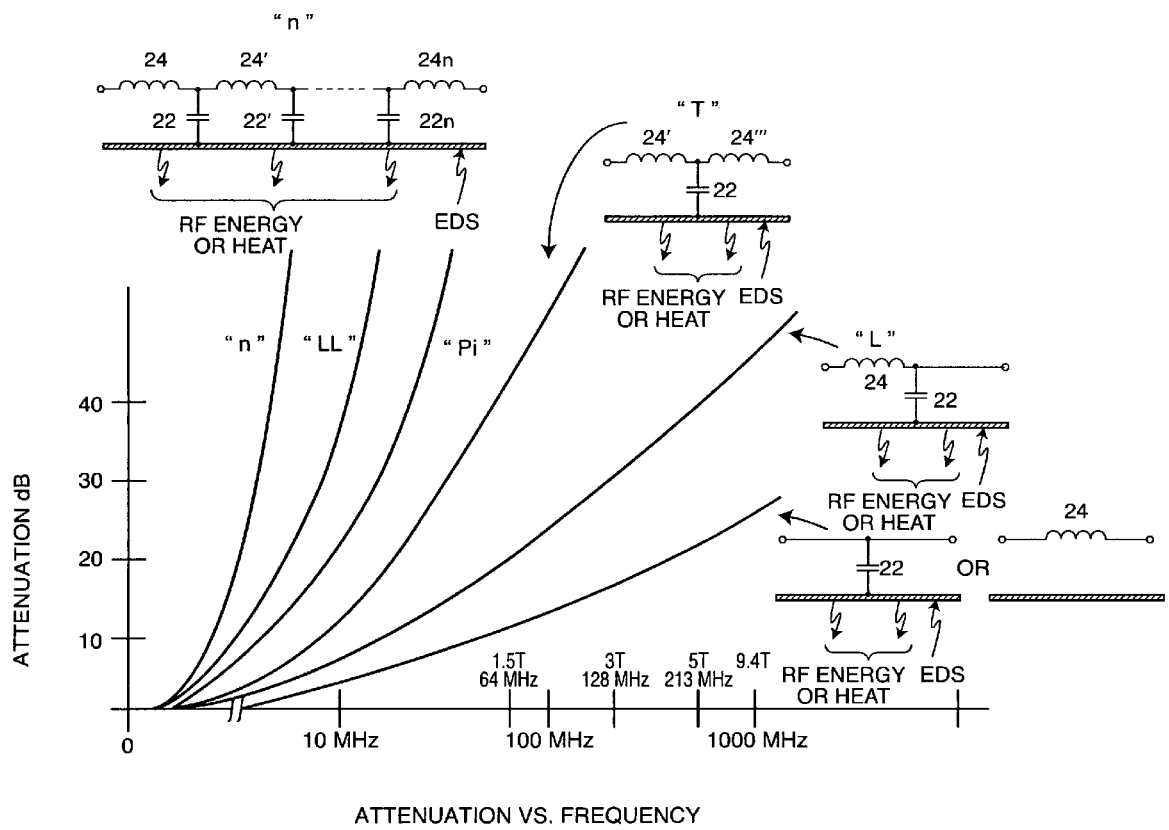
FIG. 37 is an attenuation versus frequency chart for various types of low pass filters.
Figure 38:
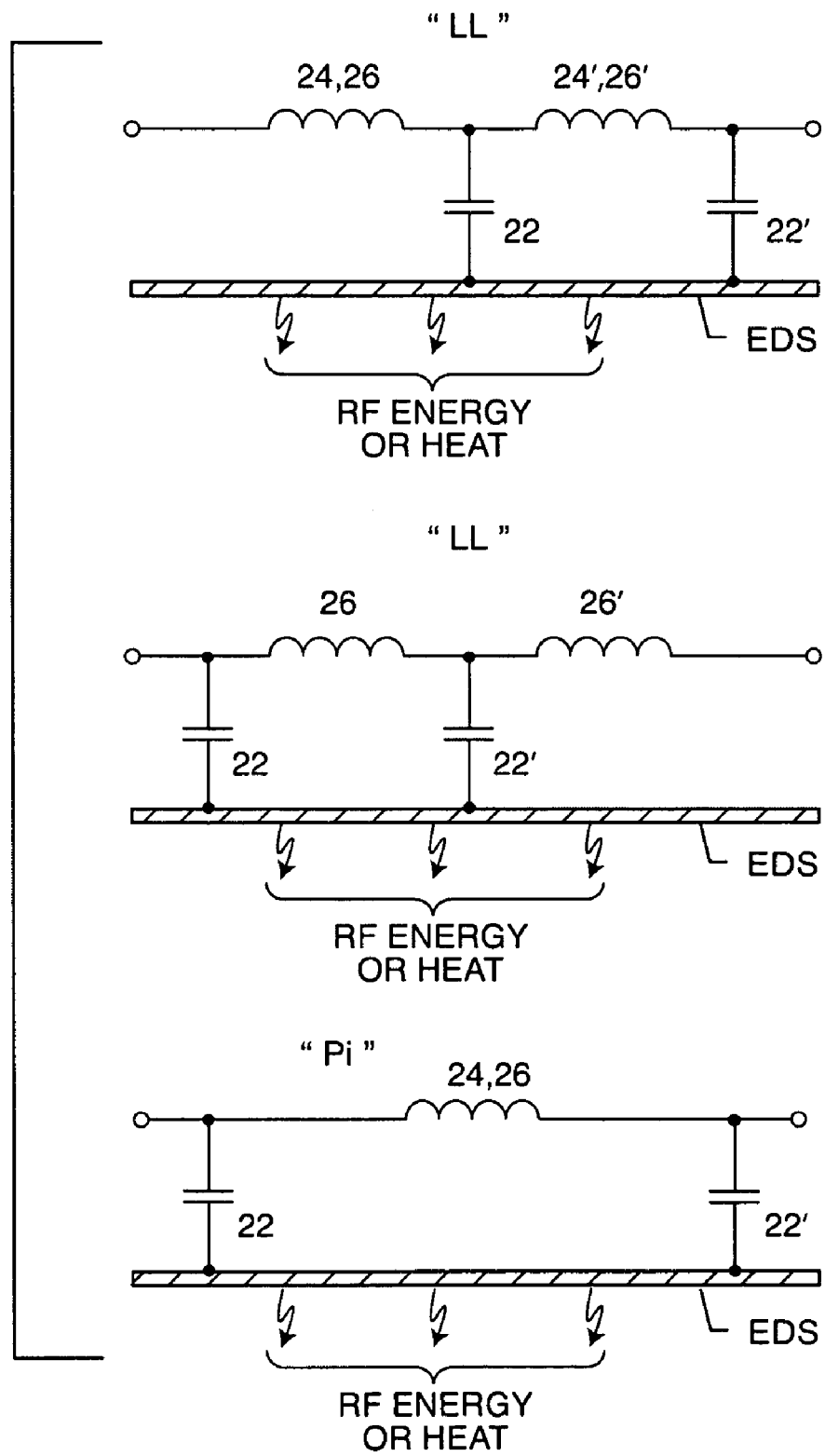
FIG. 38 shows schematic circuit diagrams for different types of low pass filters charted in FIG. 37.

The various types of low pass filters are more thoroughly shown in FIGS. 37 and 38 which compares the filtering efficiency measured as attenuation in dB with increasing numbers of filter elements. Shown are a single element low pass filter consisting of the capacitor 22 or an inductor 26, an L filter which consists of an inductor 26 and a capacitor 22, a T filter as shown in FIGS. 35-37, a Pi filter (FIG. 38), an LL filter (FIG. 38) or an "n" element filter (FIG. 37). FIG. 37 shows the general response curves of these types of filters in attenuation versus frequency. The schematics for these various filters, which are correlated to the curves in FIG. 37, are shown on FIG. 38. As one increases the number of filter elements, the ability to attenuate or block high frequency signals from reaching a distal electrode is improved. Referring once again to FIG. 37, for example, one can see that for a particular value of a single element capacitive filter, the attenuation for a 1.5 Tesla MRI system operating at 64 MHz is only about 12 dB. This means that a certain amount of the RF energy would still reach the distal tip electrode. Now compare this to the T filter of FIGS. 35-37, where one can see that there is in excess of 45 dB of attenuation. In this case, an insignificant amount of RF energy from the RF pulsed frequency of the MRI, would reach the distal electrode. Accordingly, one preferred embodiment of the present invention is that a capacitor combined with one or more inductors would be an optimal configuration. As the number of elements increases, the filtering efficiency improves. When the filtering efficiency improves, this means that less and less RF energy will reach the distal tip.

Figures 39, 39A:
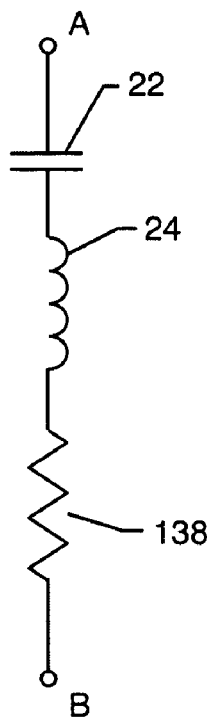
FIG. 39 is a schematic circuit diagram illustrating an L-C trap filter.
FIG. 39A depicts a resonant frequency equation for the L-C trap filter of FIG. 39.

FIG. 39 illustrates a schematic diagram of a series inductor 24-capacitor 22 filter which is commonly known in the industry as a trap filter. The trap filter was previously described in connection with FIG. 6. Referring once again to FIG. 39, there is a particular frequency for a trap filter when the capacitive reactance becomes equal and opposite to the inductive reactance. At this single frequency, the capacitive reactance and the inductive reactance cancel each other out to zero. At this point, all one has left is the residual resistance 138. If one selects high quality factor (Q) components, meaning that they are very low in resistance, then the trap filter of FIG. 39 ideally tends to look like a short circuit at its resonant frequency $F_r$ between points A and B which may comprises connections respectively to a pair of leadwires 12 and 14. FIG. 39A gives the resonant frequency equation where $F_r$, in this case, was measured in hertz. FIG. 9 shows the effect of a short circuit 30 between leadwires 12 and 14. Referring once again to FIG. 39, it is important that the amount of resistance R be controlled. This is better understood by referring to FIG. 40.

Figure 40:
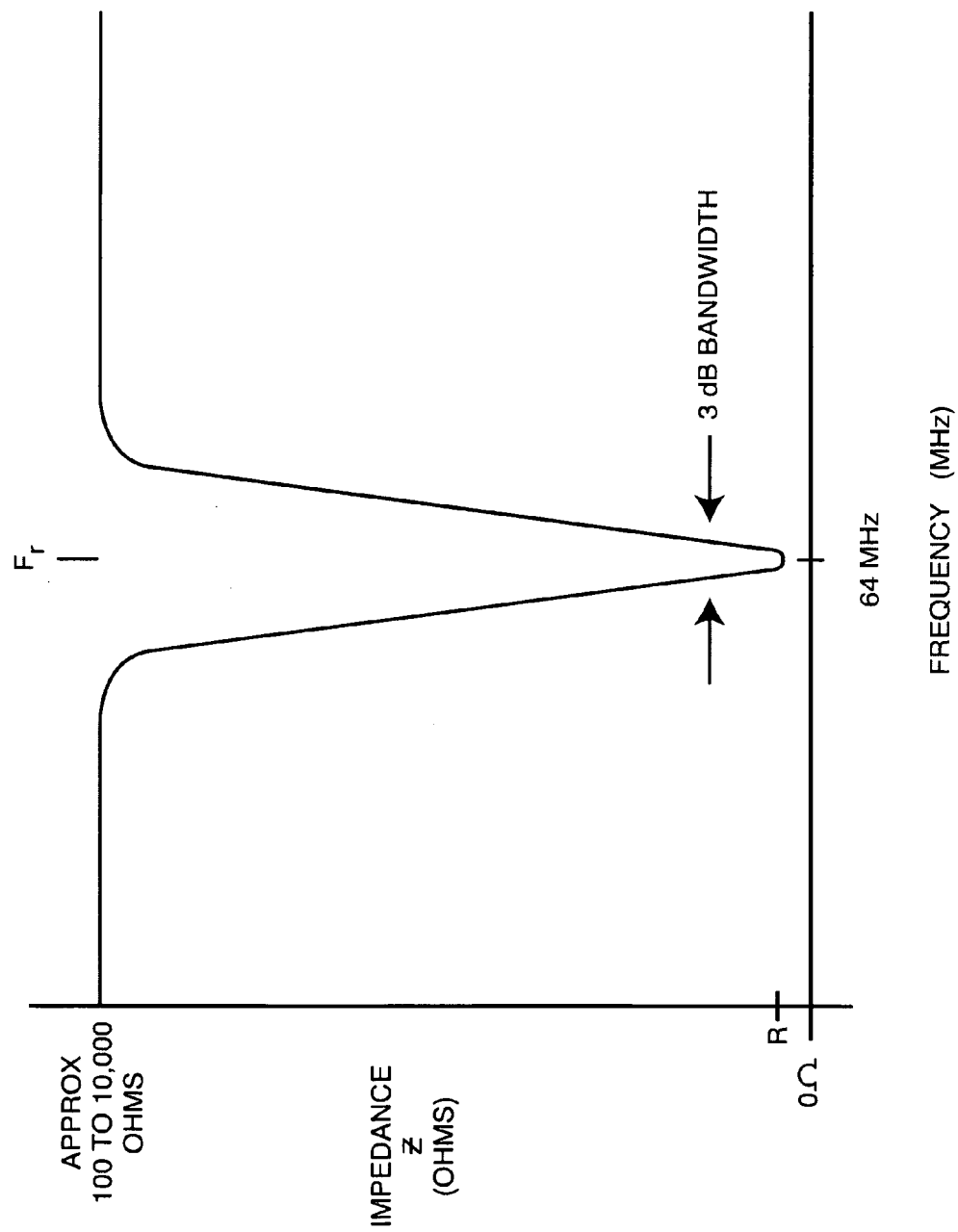
FIG. 40 is an impedance versus frequency chart for the L-C trap filter of FIG. 39.

FIG. 40 illustrates the impedance Z in ohms versus frequency of the series resonant L-C trap filter of FIG. 39. As one can see, the impedance is quite high until one reaches the frequency of resonance $F_r$. At this point, the impedance of the series L-C trap goes very low (nearly zero ohms). For frequencies above or below resonance $F_r$, depending on the selection of component values and their quality factor (Q), the impedance can be as high as 100 to 1000 or even 10,000 ohms or greater. At resonance, the impedance tries to go to zero and is limited only be the amount of parasitic resistance 138 (FIG. 39) that is generally composed of resistance from the inductor 24 and also the equivalent series resistance from the electrode plates of the capacitor 22. There is a trade off in proper selection of the components that controls what is known as the 3 dB bandwidth. If the resistance is extremely small, then the 3 dB bandwidth will be narrower. However, this makes the trap filter more difficult to manufacture. Accordingly, the 3 dB bandwidth and the resistive element R are preferably selected so that it is convenient to manufacture the filter and tune it to, for example, 64 MHz while at the same time providing a very low impedance R at the resonant frequency. For an ideal L-C series resonant trap filter, wherein ideal would mean that the resistance R would be zero, then the impedance at resonance would be zero ohms. However, in this case, the 3 dB bandwidth would be so narrow that it would be nearly impossible to manufacture. Accordingly, some amount of resistance R is in fact desirable.

As previously mentioned, there is a disadvantage to use of the L-C trap filter as shown in FIG. 6. That is, it is really only effective for attenuating the one MRI frequency (for example, 64 megahertz for a 1.5 megahertz scanner). Accordingly, when the AIMD manufacturer would apply for their FDA conditional labeling, they could only claim compliance with 1.5 Tesla MRI scanners. However, the L-C trap filter of FIG. 6 also offers a very important advantage in that it offers a very high degree of attenuation at this one selected frequency and is also highly volumetrically efficient. Accordingly, there is a trade-off here. When one uses a broadband low pass filter, a broad range of frequencies is attenuated at the cost of increased size and complexity (an additional number of components). An L-C trap filter such as shown in FIG. 6 is more of a "rifle-shot" approach wherein only one selected frequency is attenuated. In physics, this is more efficient and tends to make the components smaller.

Figure 41:
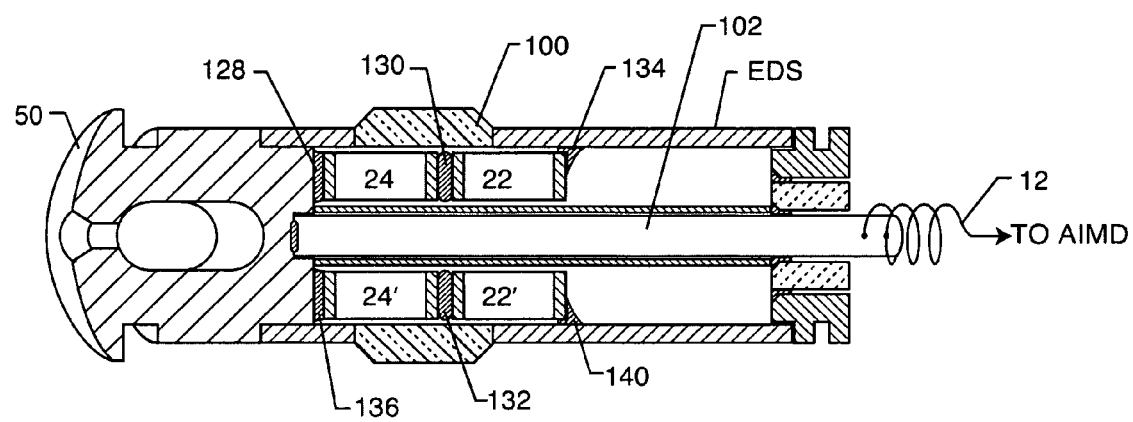
FIG. 41 is a sectional view similar to FIGS. 30, 34 and 35, but shows still another alternative embodiment of the invention for decoupling RF signals from an electrode leadwire.

FIG. 41 illustrates yet another method of decoupling RF signals from leadwire 12. Referring back to FIGS. 30 through 38, all of the aforementioned decoupling techniques involve broad band low pass filtering. The advantage with these is that they would be applicable to a wide range of MRI machines including 0.5, 1.5, 3.0, 5.4 Tesla and so on. In other words, these broad band EMI filters would attenuate a broad range of RF frequencies. In FIG. 41, one can see that there are two discrete L-C trap filters. The first trap filter consists of inductor 24 and capacitor 22 acting in series, and the second trap filter consists of inductor 24' and capacitor 22' operating in series. This is best understood by referring to the schematic of FIG. 42 which shows the series connection of 24, 22 from the lead 102 to the energy dissipating surface EDS. Inductor 24' and capacitor 22' are also connected in series from the lead 102 to the energy dissipating surface EDS.

In FIG. 41, one can see that an electrical connection 128 is made between the distal tip electrode 50 and inductor chip 24. Inductor chip 24 is then electrically connected via electrical connection material 130 to monolithic chip capacitor (MLCC) capacitor 22. The other end of the chip capacitor 22 is electrically connected at 134 to the energy dissipating surface EDS. Inductor 24' is also connected to the distal tip electrode 50 by material 136. The other end of inductor 24' is connected in series at 132 with capacitor 22'. The other end of capacitor 22' is electrically connected at 140 to the energy dissipating surface EDS. In this way, the two trap filters are connected in parallel between the lead 102 and the energy dissipating surface EDS as shown in the schematic diagram of FIG. 42.

Figure 43A:
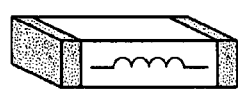
FIG. 43A illustrates a typical chip inductor for use in the sealed electrode assembly of FIG. 41.

FIG. 43A illustrates a typical chip inductor 24, 24' which can be used in FIG. 41.

Figure 43B:
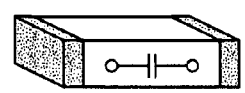
FIG. 43B illustrates a typical chip capacitor for use in the sealed electrode assembly of FIG. 41.

FIG. 43B is a typical prior art MLCC chip capacitor 22, 22' which can also be used in conjunction with the package shown in FIG. 41.

Figure 44:
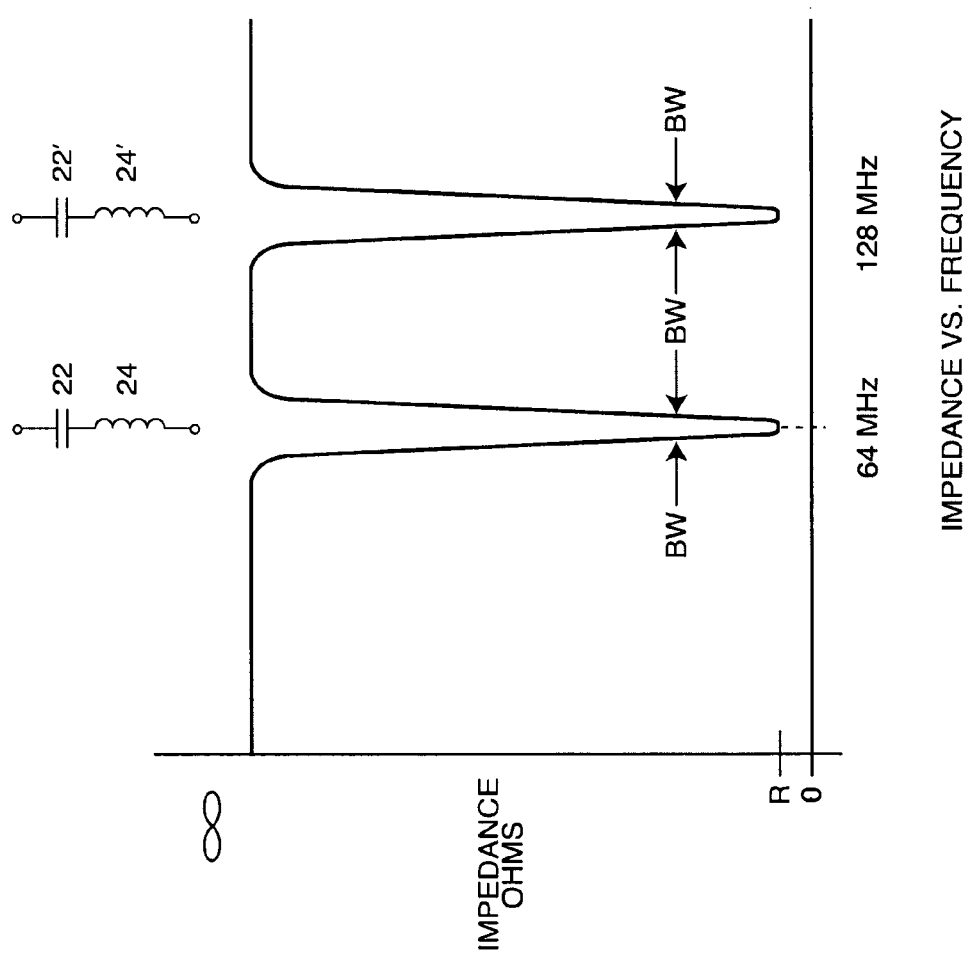
FIG. 44 is an impedance versus frequency chart for the dual L-C trap filter embodiment of FIG. 41.

FIG. 44 is a graph of impedance versus frequency showing the impedance in ohms for the L-C trap filter elements that were previously described in FIGS. 41 and 42. By carefully selecting the component values 22 and 24 and also 22' and 24', one can select the frequencies at which the two (or more) L-C trap filters will self-resonate. In the present example, the first trap filter including components 22 and 24 has been selected to resonate at 64 MHz, and the second trap filter including element 22' and 24' has been selected to resonate at 128 MHz.

Referring once again to FIG. 44, one can see that we now effectively have dual trap filters which tend to short out leadwire 102, 12 at two different frequencies. In this case, by example, the first trap filter resonates at 64 MHz, which is the RF pulsed frequency of a 1.5 Tesla MRI system. The second trap filter, which has resonant frequency $F_{r2}$ at 128 MHz, is designed to attenuate the RF pulsed signals from a 3 Tesla MRI frequency. It will be appreciated that a multiplicity of trap filters can be used depending on how many different types of MRI systems that one wants to have compatibility with for an implanted lead and electrode. The method of selecting the resonant frequency was already described in FIG. 39A and is applicable to FIG. 44. Referring once again to FIG. 44, one will note that except at the resonant frequency $F_{r1}$ and $F_{r2}$, the impedance of the trap filter is very high. This is very important so that low frequencies are not attenuated. Accordingly, using a cardiac pacemaker application as an example, pacing pulses would be free to pass and also low frequency biologic signals, such as those that are produced by the heart. It is very important that pacemaker sensing and pacemaker pacing can occur while at the same time, high frequency energy, for example, that from the RF pulsed frequency of an MR system can be diverted to an appropriate energy dissipating surface EDS.

Figure 45:
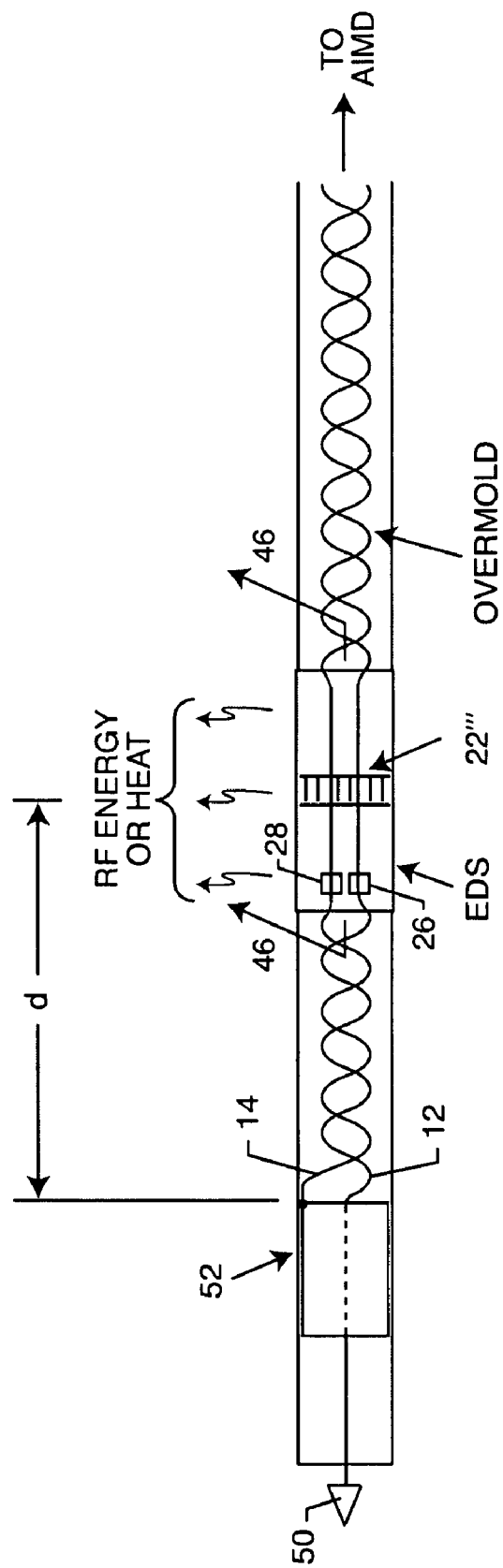
FIG. 45 is a schematic representation of an implantable medical device bipolar leadwire system.

FIG. 45 illustrates a typical active implantable medical device bipolar leadwire system. On the left is shown a distal tip electrode 50 and a distal ring electrode 52. The energy dissipating surface EDS of the present invention is shown along with coaxial leadwires 12 and 14 which would be connected to the AIMD. These could be endocardial or epicardial in accordance with the prior art.

FIG. 46 is a blown up sectional view generally taken from section 46-46 from FIG. 45. In FIG. 46, one can see that there is an energy dissipating surface EDS which is enclosed at both ends by two hermetic seal flanges or flange assemblies each consisting of a flange 108, an insulator 142 and gold brazes 110. This is designed to be laser welded as at 112 into the metallic energy dissipating surface EDS as shown. A bipolar feedthrough capacitor 22''' is shown in cross-section in FIG. 46 where the two leadwires 12 and 14 pass through it. The feedthrough capacitor 22''' is a very efficient broad band filter which would tend to decouple high frequency signals such as 64 MHz (1.5 Tesla) and 128 MHz (3 Tesla) from the leadwires 12, 14 to the energy dissipating surface EDS in accordance with the present invention. Each leadwire 12 and 14 may additionally include the frequency selective reactances 26 and 28 (as previously shown and described in FIGS. 7, 10 and 11).

Figure 47:
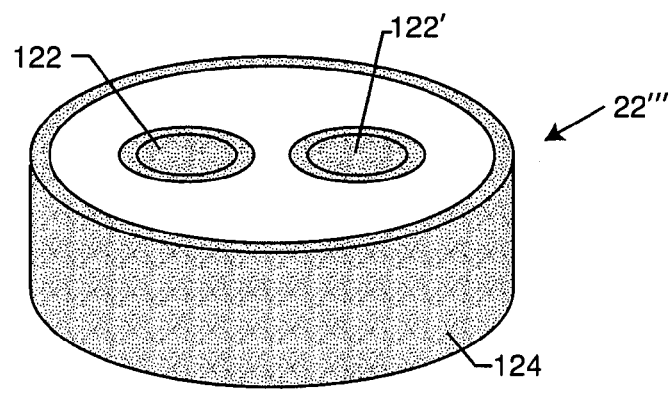
FIG. 47 is an isometric view of a bipolar feedthrough capacitor for use in the device of FIGS. 45-56.

The bipolar feedthrough capacitor 22''' is illustrated in isometric view in FIG. 47. Shown is an outside diameter termination surface 124 which is electrically and thermally connected to the inside diameter of the energy dissipating surface EDS of FIG. 42, as by electrical connection 144 (FIG. 46). Also shown, are inside termination surfaces 122 and 122' located on the inside diameter of two feedthrough capacitor ID holes for electrical connection at 146 and 146' (FIG. 46) between leadwires 12 and 14, respectively to the feedthrough capacitor termination surfaces 122 and 122', respectively. The use of a feedthrough capacitor in this case makes for a truly broadband performance. As MR systems continue to evolve in their static magnetic field strength, the RF pulse frequencies go higher and higher. For example, for a 10 Tesla scanner, the RF pulse frequency is 426.5 megahertz. Prior art MLCC chip capacitors have internal inductance and tend to self-resonate at frequencies around 400 megahertz or above. Accordingly, the use of a feedthrough capacitor accommodates much higher frequency MRI systems.

Figure 64:
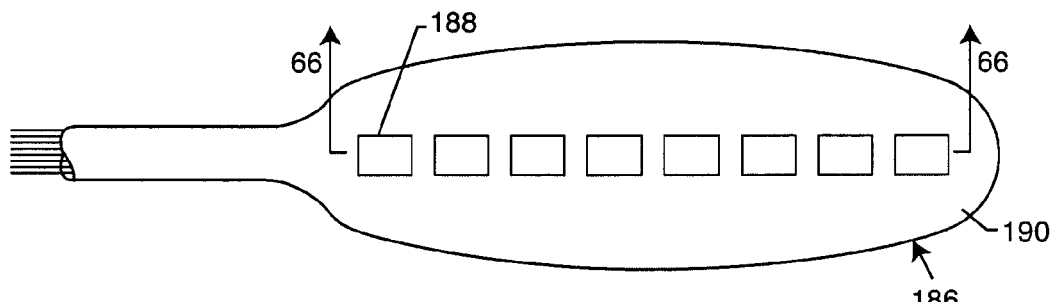
FIG. 64 is a fragmented top plan view of an exemplary paddle electrode embodying the present invention.
Figure 65:
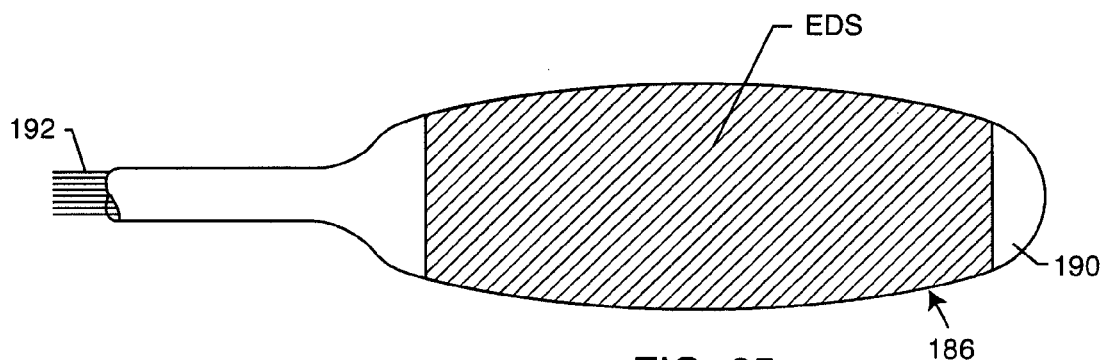
FIG. 65 is a bottom plan view of the paddle electrode shown in FIG. 64.
Figure 66:
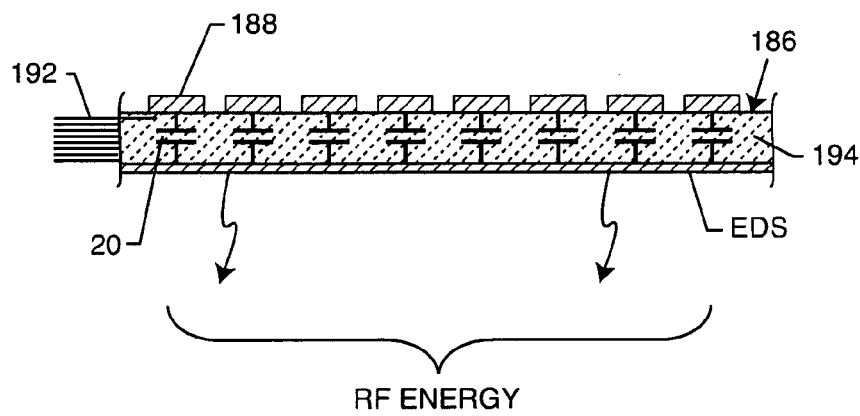
FIG. 66 is an enlarged sectional view taken generally along the line 66-66 in FIG. 64.

Referring once again to FIG. 26 and FIG. 29, one can understand why the energy dissipating surface EDS of FIG. 45 has been moved back a suitable distance "d" from the distal tip electrode 50 and the distal ring electrode 52. This is because of the tendency for distal tip 50 and ring electrodes 52 to become completely embedded or encapsulated with body tissue. In other words, one cannot guarantee that the distal ring electrode 52 will always be freely floating in the blood pool, for example, of the right ventricle or the right atrium. Referring once again to FIG. 25, one can see shaded areas where tissue encapsulation tends to be the greatest. An ideal location for the energy dissipating surface EDS, as described in FIG. 45, is shown as EDS' in FIG. 25. This guarantees that the energy dissipating surface is placed generally into the area of the right ventricle that is free of traebuclar tissue and where there is always freely flowing blood. Of course, this is particularly important for cardiac rhythm management applications wherein pacemakers and implantable defibrillators are commonly used. For implantable neurostimulators, generally, these are not placed in areas where there is freely flowing blood. However, it is still important in these cases that the energy dissipating surface be a sufficiently large enough distance from the associated electrode(s) so that if there is adjacent tissue heating, it does not affect the delicate interface between the electrodes and surrounding body tissue. This would be particularly important, for example, in a deep brain stimulator. As shown in FIG. 29, for example, an ideal location for the energy dissipating surface would be either at the skull or subdural (slightly below the skull). In this case, the deep brain stimulation electrode would protrude down into the brain tissue below the energy dissipating surface EDS. In this case, the RF energy and/or heat would be dissipated over a relatively large surface area well away from the very heat sensitive and delicate brain tissues 82. For a spinal cord stimulator, there is generally freely flowing spinal fluid which can act as a cooling agent as well. In this case, it is desirable to have the EDS surface, again, spaced at some distance from the therapy delivery electrode such that cooling effectively takes place within the cerebral spinal fluid. See U.S. Publication Nos. US 2008-0132987 A1 and US 2007-0112398 A1, which are incorporated by reference herein. In some cases, the separation distance can be quite small, for example on the opposite surface of a paddle electrode as shown in FIGS. 64, 65 and 66.

Figure 48:
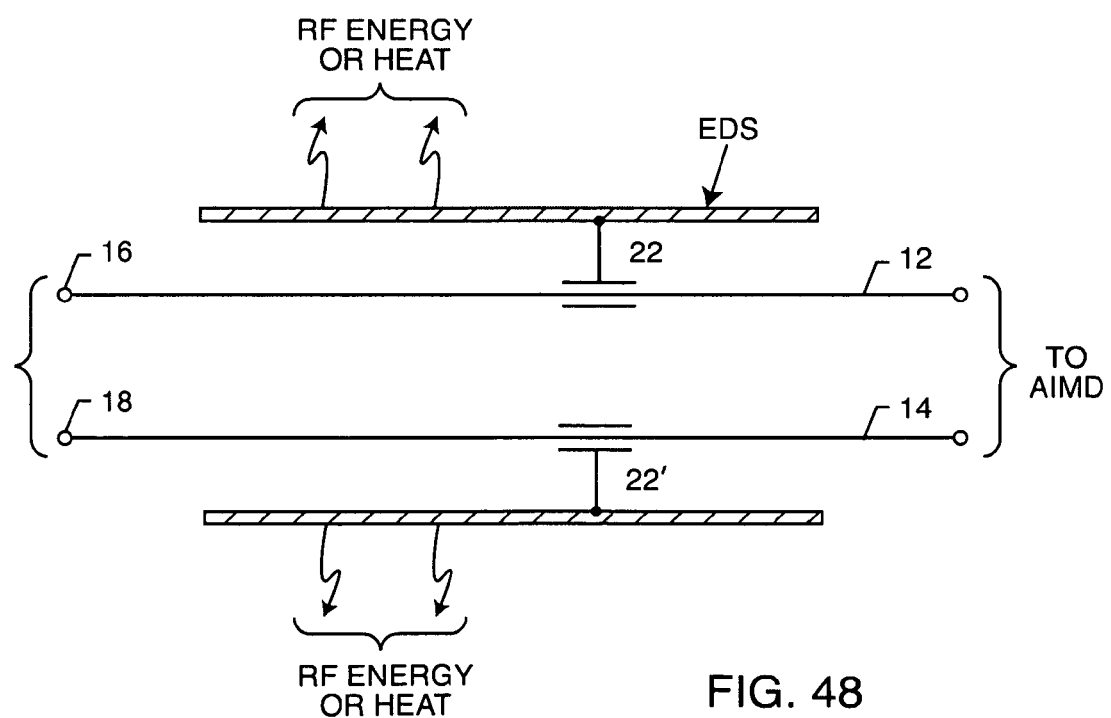
FIG. 48 is a schematic circuit diagram corresponding with the embodiment shown in FIGS. 45-46.

FIG. 48 is a schematic diagram of the energy dissipating surface assembly previously described in FIGS. 45 and 46. From FIG. 48, one can see that the passive frequency selective elements 22 and 22' could be replaced by any of the circuits previously described in FIGS. 4 through 11 as element 20.

Figure 49:
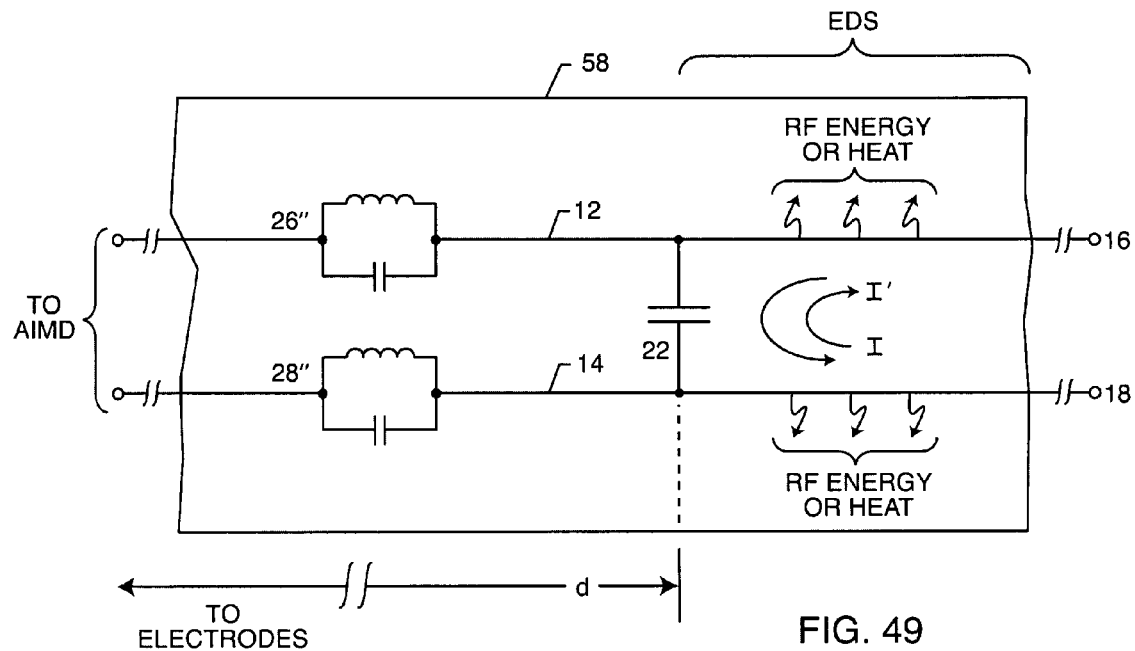
FIG. 49 is a schematic circuit diagram illustrating a bipolar lead assembly with distal tip and ring electrodes shown at a suitable distance from an energy dissipation surface (EDS)

FIG. 49 illustrates a bipolar lead of the present invention with distal tip and ring electrodes 16, 18 shown distally at a suitable distance d from a energy dissipation surface (EDS) such that energy dissipation in the EDS would not cause a temperature rise at the distal electrodes. Shown is a capacitor 22 connected between the leadwires 12 and 14. Also shown are a pair of bandstop filters 26" and 28" as previously illustrated in FIG. 11. In fact, the passive component network configuration of FIG. 49 is identical to that previously illustrated in FIG. 11, wherein the frequency selective element 20 is a capacitor 22. Referring once again to FIG. 49, one can see that the capacitor element 22 acts as a high frequency energy diverter. This works in cooperation with the two bandstop filter elements 26" and 28" which act as energy impeders at a selected MRI frequency. Accordingly, high frequency energy that is induced on the leadwires 12 and 14 is converted to RF circulation currents $I_1$ and $I_2$. $I_1$ and $I_2$ are shown in opposite directions to illustrate, for example, for a 1.5 Tesla MRI system, that these oscillate back at 64 million times per second. This creates a great deal of current in the associated leadwires to the right (as viewed in FIG. 49) of the diverting element 22. This causes heat to be dissipated in the leadwires 12 and 14 into the energy dissipating surface EDS such as the overall insulation sheath or shield of the probe, catheter or implanted device as shown.

Figure 50:
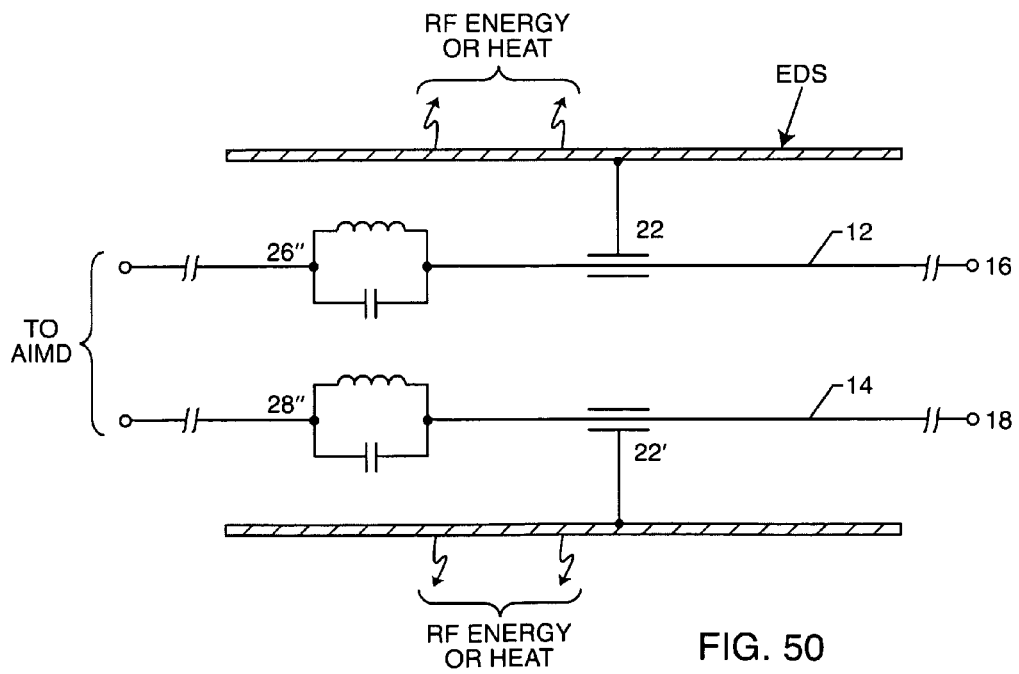
FIG. 50 is a schematic circuit diagram similar to FIG. 49, except that a pair of capacitors are used.

FIG. 50 is very similar to FIG. 49 except that diverting element 20 had been replaced by a pair of capacitor elements 22 and 22' which connect from leadwires 104 and 104' respectively to an electromagnetic shield or an energy dissipating surface EDS. It is a desirable property of the present invention that the EDS surface be highly thermally conductive, have relatively high surface area for efficient transfer of RF or heat energy into surrounding fluids and body tissue and also be electrically conductive at RF frequencies.

The bandstop filters 26" and 28" of FIG. 50 look like a very high impedance (ideally an infinite impedance) at the resonant frequency. This has the effect of disconnecting the distal electrodes at these high frequencies from the leadwires 12 and 14. These work in conjunction with the low pass filter elements 22 and 22' which act as a way to divert the high frequency energy to the energy dissipating surface EDS. As previously mentioned, the low pass filter elements 22 and 22' can consist of any of the low pass filters as previously described in FIGS. 37 and 38 or the L-C trap filter as previously described in FIGS. 39, 39A, 40, 41 and 44. A high frequency model of FIG. 50 is illustrated in FIG. 9 wherein the leadwires are effectively shorted together to an energy dissipating surface EDS and the distal electrodes 16 and 18 have been effectively disconnected (in this case, by the bandstop filter elements) from the electrodes. For a more complete description of bandstop filter elements and their design and operation, refer to U.S. Pat. No. 7,363,090.

Figure 51:
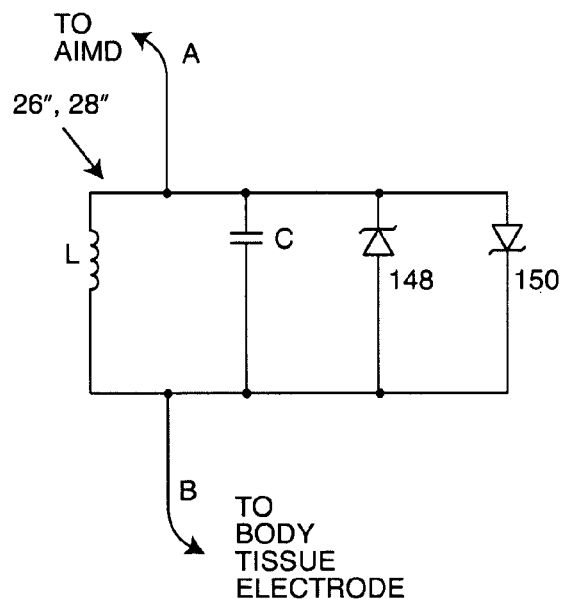
FIG. 51 is a schematic circuit diagram illustrating a band stop filter modified to include a pair of diodes in a parallel or back-to-back configuration.

FIG. 51 illustrates an exemplary bandstop filter 26" or 28" consisting of a parallel inductor L and capacitor C (as previously shown and described herein) with nonlinear circuit elements such as diodes 148 and 150 placed in parallel therewith. These diodes 148, 150 are oriented in what is known in the prior art as a back-to-back configuration. Nonlinear circuit elements (such as diodes) can allow the device to be "switched" between different modes of operation. The diode elements 148, 150, as illustrated in FIG. 51, can be placed in parallel with each other, and with any of the frequency selective circuit elements as previously described in FIGS. 4 through 11. For example, referring to FIG. 5, the diode elements 148 and 150 could be placed in parallel with the capacitive element 22. Referring to FIG. 10, two diode elements 148, 150 could also be placed in parallel with each of the inductor elements 26' and 28'. As previously discussed, automatic external defibrillators (AEDs) have become very popular in the patient environment. Accordingly, implanted leads must be able to withstand very high pulsed currents. These pulse currents can range anywhere from 1 to 8 amps. It is also a feature of the present invention that the passive frequency selective components be very small in size. In order for an inductor element L to be able to handle 1 to 8 amps, it would have to be exceedingly large. However, by using very small diode elements 148 and 150, one can have the circuits switched to a different state. That is, when a high voltage, such as that from an AED appears, the diodes would forward bias thereby temporarily shorting out the bandstop filter 26" or 28" consisting of the parallel combination of inductor L and capacitor C (FIG. 51.). Thereby the correspondingly high AED induced currents would be diverted away from the relatively sensitive (small) passive elements L and C in such a way that they not be harmed.

Figure 52:
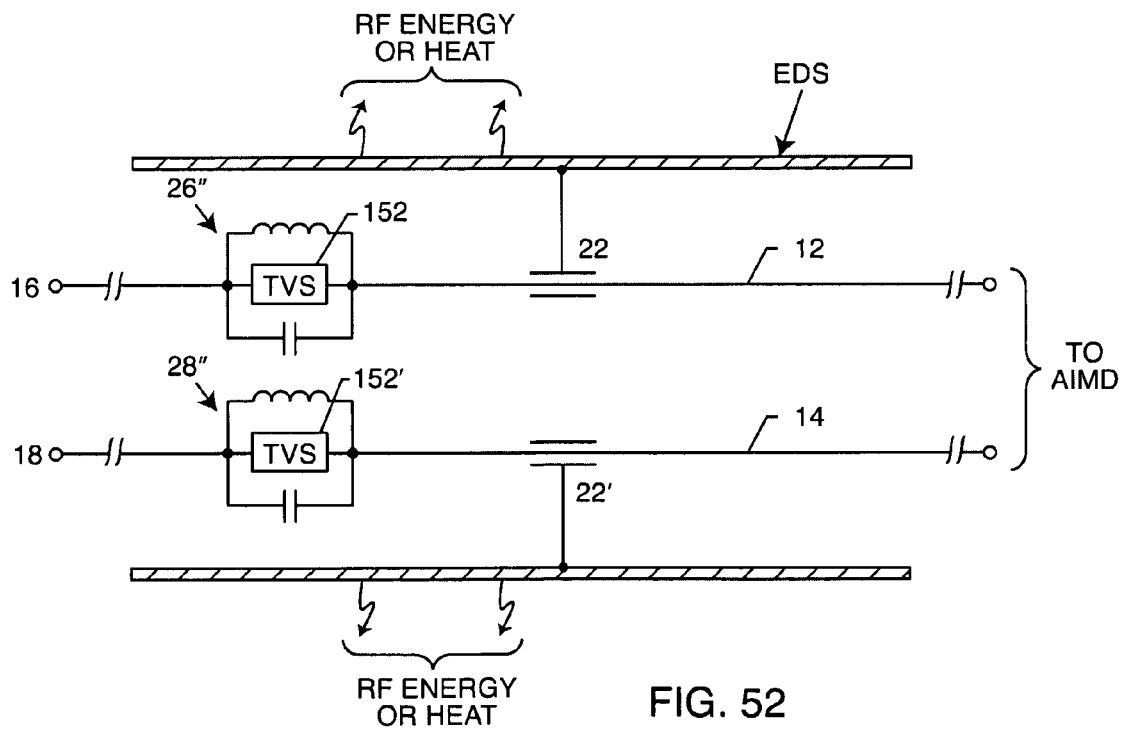
FIG. 52 is a schematic circuit diagram similar to FIG. 50, except that transient voltage suppressors are installed in parallel relation with each of the bandstop filter elements.

FIG. 52 is nearly identical to FIG. 50 except that transient voltage suppressors 152 and 152' have been added respectively in parallel with the bandstop filter elements 26" and 28". Transient voltage suppressors are nonlinear circuit elements which operate in much the same fashion as previously described for the back-to-back diodes 148 and 150 of FIG. 51. This family includes diodes, zener diodes, Transorbs™, Transguard®, metal oxide varistors, $Z_n0$ varisters, and other similar nonlinear circuit elements. The purpose of the transient voltage suppressors 152 and 152' in FIG. 52 is to bypass any high voltage induced currents such that these currents not flow through the relatively sensitive bandstop passive component inductor and capacitor elements.

Figure 53:
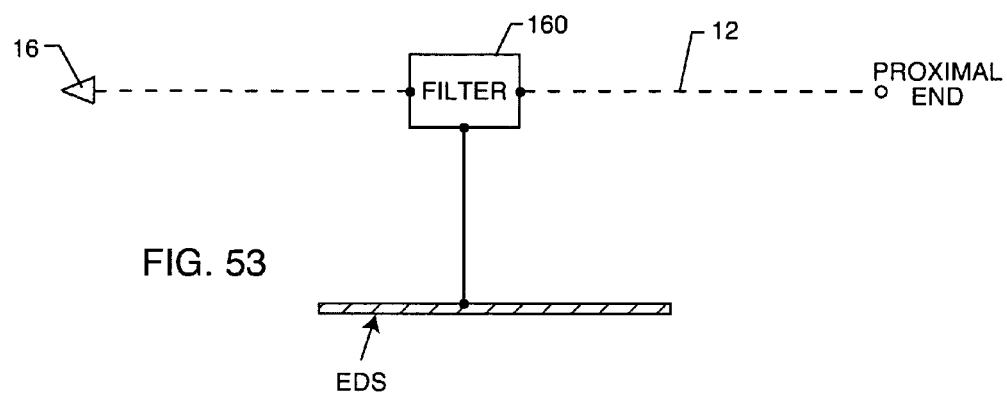
FIG. 53 is a schematic circuit diagram depicting a general filter element constructed in accordance with any one of the embodiments shown and described herein, wherein the filter element is coupled between the distal and proximal ends of a leadwire or the like, for dissipating RF energy or heat to an adjacent energy dissipating surface.

FIG. 53 illustrates a general filter element 160 which can be representative of any of the filters previously described. The filter element 160 of FIG. 53 is shown disposed between an electrical connection to an energy dissipating surface EDS as illustrated. The filter is shown connected to a proximal end of a leadwire 12 or the like with dashed lines, and connected to a distal end electrode 16 shown coupled to the leadwire 12 or the like with dashed lines. The reason for the dashed lines is an indication that the filter 160 can be placed anywhere between the distal end and the proximal end of the leadwire 12. The filter 160 and energy dissipating surface EDS could be located near the distal end, at the distal end, at a distal ring electrode 52 or near a distal ring electrode 52 such that it would float in the blood pool. The filter 160 can also be placed at or near the proximal end, or at any point between the distal and proximal ends.

In particular, the filter and associated energy dissipating surface EDS could be all the way at the proximal end of an abandoned lead. Leads are often abandoned in application for various reasons. Sometimes the lead becomes slightly dislodged, for example, from cardiac tissue such that the pacing threshold increases or is lost. Sometimes lead insulation becomes abraded and/or the leadwire itself is broken. Removing leads once they've been in the body for a long time can be very difficult as portions of the lead tend to become overgrown by body tissue. One is again referred to the article entitled, ICD EXTRACTION INFECTED/REDUNDANT LEADS EVERYDAY CLINICAL PRACTICE by Dr. Bruce Wilkoff. When one looks at the photographs of the extracted leads, one can see that they are very often substantially overgrown with tissue. Therefore, it is common practice to simply abandon leads.

In the prior art, the abandoned lead is simply capped such that body fluid will not enter it. This cap is nothing more than an insulative cap. However, it is also well known in the literature that abandoned leads can be quite dangerous in an MR scanning situation. High energy electromagnetic fields from the RF pulsed energy of a scanner intensifies at the ends of implanted leads. Because they are abandoned or capped at one end, this creates a reflection situation whereby all of the intense energy has no way to escape the lead except at the distal electrode end. This is the worst case situation because the distal electrode makes intimate contact with body tissue. For example, if the tissue was myocardial tissue, one runs a severe risk of creating burning or lesions in the heart. In the case of a deep brain stimulator, one runs the risk of causing deep lesions within the brain. In an abandoned lead, therefore, it is much more desirable that energy be dissipated at or near the proximal end as opposed to the distal end where there are sensitive body tissues involved. In general, active implantable medical devices are implanted in muscle or in fat tissues, for example, in the pectoral areas which are not so heat sensitive, but more importantly, are not implanted in an organ, whose function could be compromised. Accordingly, it is a feature of the present invention that any of the filter networks, as previously described herein, including those as shown in FIGS. 4 through 11, could be incorporated in a cap structure to be attached to the proximal end of the leadwire wherein such said cap structure includes an energy dissipating surface. For a further description of the problem and the need to provide a cap for abandoned leads, one is referred to U.S. Pat. No. 6,985,775.

Figure 54:
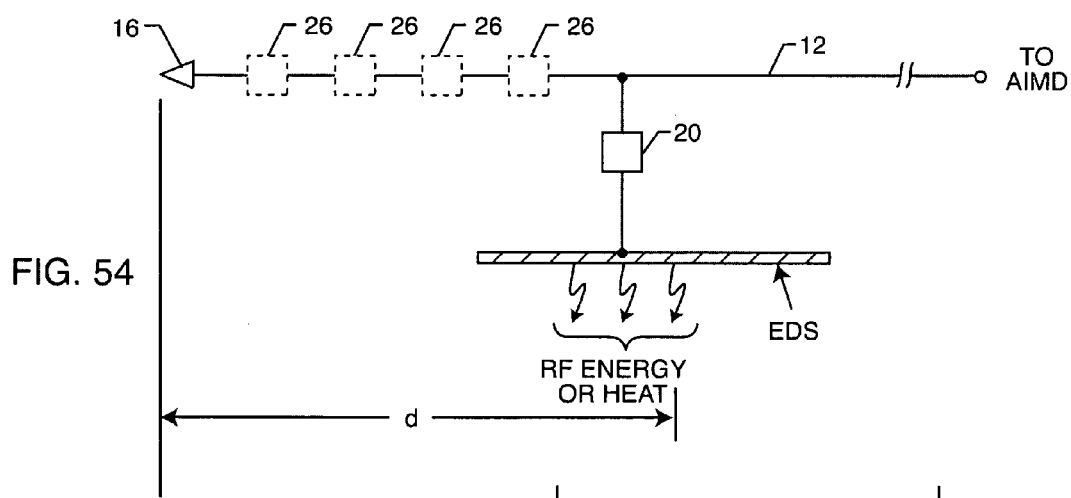
FIG. 54 is a schematic circuit diagram similar to FIG. 53, but showing alternative design considerations.

FIG. 54 shows an energy dissipating surface EDS in a relatively fixed location along the length of a leadwire 12. In accordance with the present invention, the energy dissipating surface EDS is placed a suitable distance d from a distal electrode 16 such that energy dissipation in the area of the EDS surface will not cause tissue overheating at or near the distal electrode 16. Also shown is a frequency impeding element 26 which can be moved to various locations along the length of the leadwire 12 as indicated by the multiple dashed-line boxes 26. For example, impeding element 26 could be placed near the energy dissipating surface EDS, or it could be moved toward the distal electrode 16 at any one of several successive locations. The impeding element 26 such as a bandstop filter 26" or a series inductor will still work in conjunction with the diverting element 20 at any of these various locations. In fact, this can be an advantage in the present invention in order to make the distal tip electrode 16 and its associated leadwire 12 within the distance "d" smaller in diameter. In general, most leads for cardiovascular applications are restricted to the six French (0.079 inches in diameter) region. This can be problematic for a biventricular implant where the endocardial electrode must be threaded through the venous system and then into the coronary sinus and through the great cardiac vein to one of many branch vessels which are outside of the left ventricle. These branch vessels tend to be very small in diameter and very difficult to navigate, particularly for a large lead (size four French or smaller would be ideal). There is also a similar need for certain spinal cord and deep brain stimulators which must embody electrodes that are very small in diameter. Referring back to FIG. 54, one can see that by having a relatively large diverter element 20 associated with a energy dissipating surface EDS that is located at a distance d from the distal electrode, one can then downsize the diameter of the wiring along the length of distance d. By putting the frequency impeding element such as any one of the elements 26, 26' and/or 26", one can make this single component smaller than multiple components. Accordingly, frequency impeding elements do not have to be in direct physical proximity to diverting frequency selective elements 20. As taught in FIGS. 4, 5, 6, 37 and 38, the diverting element 20 can consist not only in a capacitor or an L-C resonant trap filter, but also could include a variety of low pass filters. Referring to FIG. 37, for example, one could see that an L section low pass filter is identical to the filter described in FIG. 54, wherein element 26 represents the inductor element and element 20 represents the capacitor element. Referring once again to FIG. 54, one can incorporate a T-type filter which embodies two inductor elements. In this embodiment, the left hand inductor element 26 would be to the left of the frequency diverting element 20 and a second inductor (not shown) would be located to the right of the diverter element 20 (see FIG. 37). This right hand inductor could be located in close physical proximity to the diverter element 20, or it could also be moved away as was described for the left hand inductor element at various locations as shown in FIG. 54.

Referring back to FIG. 54, it should be noted that the variable impedance element 20 can be monolithic ceramic (MLCC) capacitors, ceramic feedthrough capacitors, or other types of capacitive circuit components. In addition, the frequency selective element 20 can be a parasitic or distributive capacitor wherein the capacitance is formed through relatively high-dielectric materials between leadwires or electrodes in an energy dissipating surface.

Figure 55:
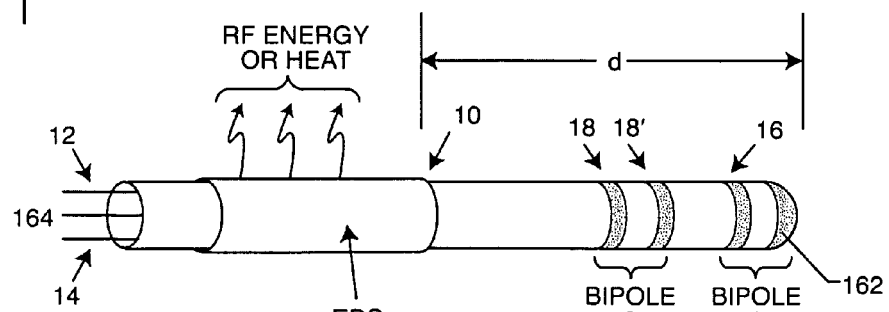
FIG. 55 depicts in somewhat schematic form a probe or catheter constructed in accordance with the present invention.

FIG. 55 illustrates a type of probe or catheter 10 which is typically used to both map and ablate the inside of cardiac chambers to eliminate or control certain types of arrhythmias. For example, in a patient with uncontrollable atrial fibrillation, this type of probe or catheter 10 would be inserted so that electrical mapping, between bipolar distal electrodes 16 and 162 or between electrodes 18 and 18', could be performed to isolate and locate those areas from which the sporadic electrical activity is occurring. For example, this might be around a pulmonary vein. Reference is made to U.S. Pat. No. 7,155,271 for a more complete description of this type of need and procedure. After the areas that need to be ablated are located, the surgeon can apply RF ablation energy at a distal ablation electrode 162. This has the effect of burning the inside of cardiac tissue creating a scar which will isolate this area of erratic electrical activity. The goal here is to complete a scar structure such that the atrial fibrillation is terminated. Unfortunately, in the prior art, this procedure is done using real-time X-ray, fluoroscopy or other types of guidance, which does not adequately visualize soft tissue. Accordingly, the surgeon is working pretty much blind as the scars forming cannot be seen in real time. As explained in U.S. Pat. No. 7,155,271, it would be a great advantage if such procedures could be performed during real time MRI guidance. The problem is the MRI RF energy induced into the ablation catheter could cause overheating and sporadic formation of scar tissue at the wrong time and/or in the wrong location. In FIG. 55, one can see that there is a novel energy dissipating surface EDS of the present invention. This EDS surface is located at a distance "d" back from the distal tip such that the energy dissipating surface will redirect energy away from both the electrical sensing electrodes 16, 18 and the RF ablation electrode 162 where they cannot overheat at inappropriate times. Frequency selective passive components (not shown), in accordance with the present invention, are connected in series with the leadwires, or from the inside of the energy dissipating surface EDS to the various leadwires 12, 14 and 164. These are the circuits that have generally been described in FIGS. 4 through 11 herein. For simplicity, they have not been shown in FIG. 54, but should be obvious to one skilled in the art from the previous drawings. In other words, the RF ablation electrode tip 162 will only overheat when the surgeon decides to activate the RF circuitry to deliberately form the scar tissue.

The energy dissipating surface EDS may include some materials or antenna structures that are readily visualized during active MRI guidance. This may be important so that a physician can ensure that if the probe or catheter is manipulated that the EDS surface not rest against the inside of, for example, the atrial septum. This is the area that is dissipating RF energy and heat during the active MRI. If the surface area of this EDS surface is sufficiently large so that very little temperature rise would occur, it would not matter if the EDS surface touched off against, for example, the inside wall of the cardiac septal wall. However, if the EDS surface was relatively small, then substantial temperature rise could occur if it was not kept within the freely flowing blood stream. In this case, it would be important that the physician be able to visualize the EDS surface and the MRI images so that it not be allowed to rest inappropriately against sensitive tissues on the inside of the atrium and cause inadvertent scar tissue or ablation to occur. Referring once again to FIG. 55, one can see that the ablation electrode 162 is connected to an RF ablation leadwire 164 which comes from RF ablation equipment (not shown) which is external to the patient. The sensing ring electrodes 16 and 18 are coupled to leadwires 12 and 14 which run through the center of the probe or catheter and also are connected to external equipment which is used to monitor electrical cardiac activity. These would typically be connected to an ECG or EKG recorder.

Figure 56:
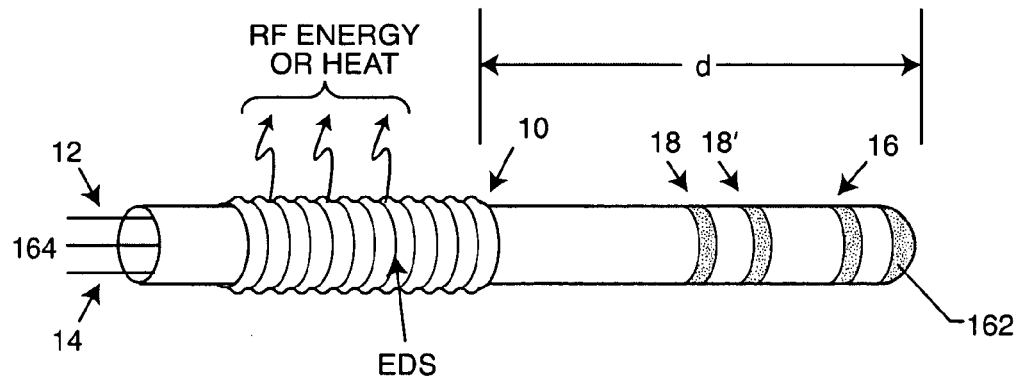
FIG. 56 is an illustration similar to FIG. 55, illustrating an alternative embodiment wherein the energy dissipating surface has been convoluted so that its surface area has been increased.

FIG. 56 shows a probe or catheter 10 similar to that illustrated in FIG. 55 except that the energy dissipating surface EDS has been convoluted so that its surface area has been increased. Such increasing of the EDS surface area, which is in contact with fluids, such as body fluids, will increase the amount of energy that is dissipated.

Figure 57:
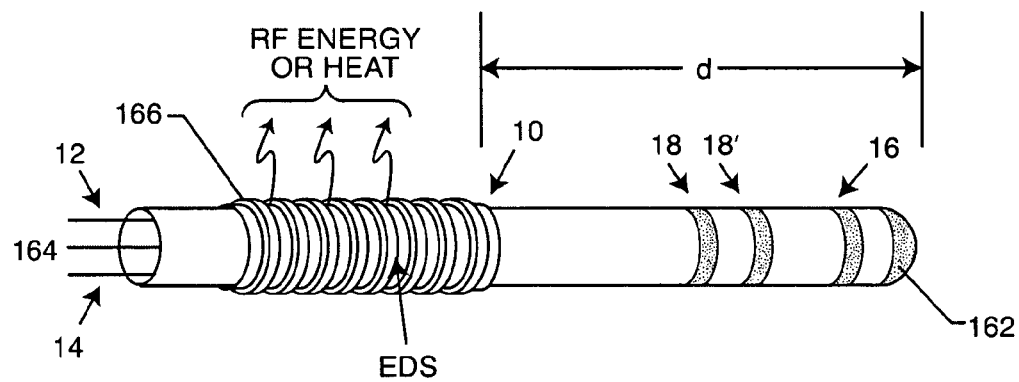
FIG. 57 is similar to FIG. 56, except that instead of convolutions, fins have been added to the energy dissipating surface.

FIG. 57 is very similar to FIG. 56 except that instead of convolutions, fins 166 have been added. These fins 166 also increase the surface area and increase the amount of energy or heat which is dissipated into surrounding fluids and tissues.

Figure 58:
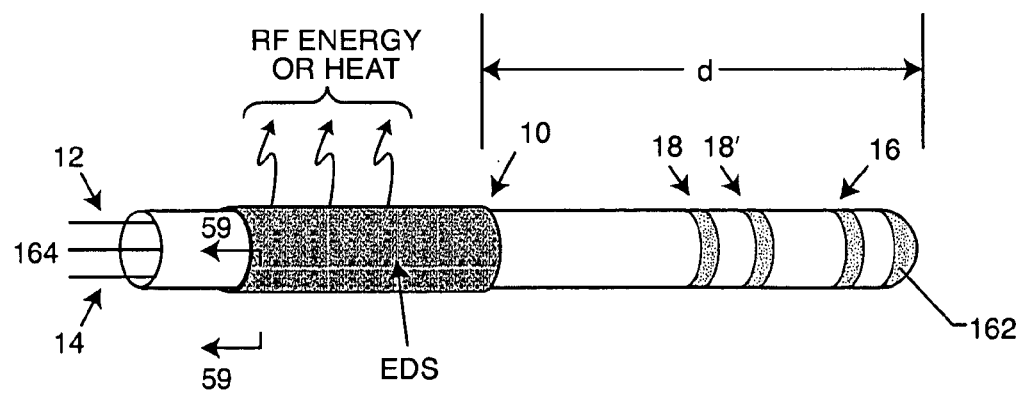
FIG. 58 is similar to FIGS. 56 and 57, except that the energy dissipating surface has its surface area increased through various surface roughening processes.
Figure 59:
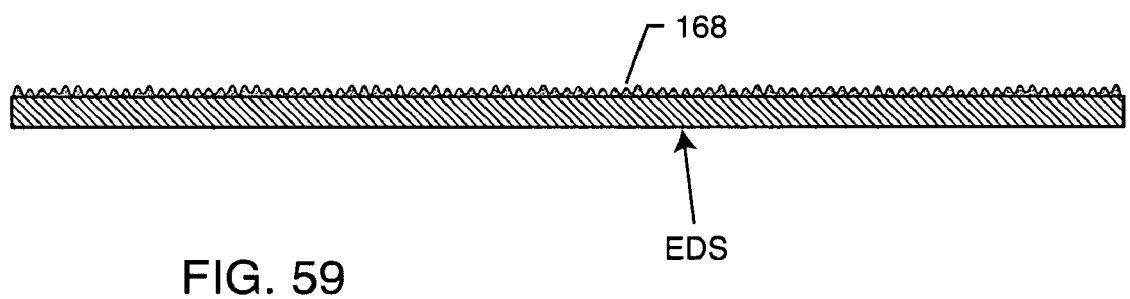
Figure 60:
FIG. 60 is a view similar to FIG. 59, and illustrates the use of carbon nanotubes or fractal coatings to increase the surface area of the energy dissipating surface.

FIG. 58 is similar to FIGS. 56 and 57 except that the energy dissipating surface (EDS) has its surface area increased through various processes which are more thoroughly described in connection with FIGS. 59 and 60. FIG. 59 is an enlarged, fragmented sectional view of the EDS surface taken from FIG. 58. The energy dissipating surface EDS area has been roughened to create a high surface area, through, for example, plasma etching 168, chemical etching, or the like. A high surface area can also be accomplished by porous coating deposits utilizing physical vapor deposition, chemical vapor deposition or electron beam deposition processes. Such porous coating deposits can include fractal coatings, metal nitrides, titanium nitrides, metal oxides, metal carbides, or virtually anything that would provide a high surface or porous substrate. In addition, electrochemical deposition of porous coating, such as iridium-oxide, can also be utilized, as well as nucleate high surface area morphologically structured coatings, such as whiskers, sub-micron filaments, tubes, nanotubes, or other morphological structures such as columnar, titanium-nitride or iridium-oxide. Any of these types of surface conditionings can greatly increase the energy dissipating surface area. FIG. 60, which is similar to FIG. 59, illustrates the use of carbon nanotubes or fractal coatings 170 to increase the surface area and therefore the energy dissipation.

Figure 61:
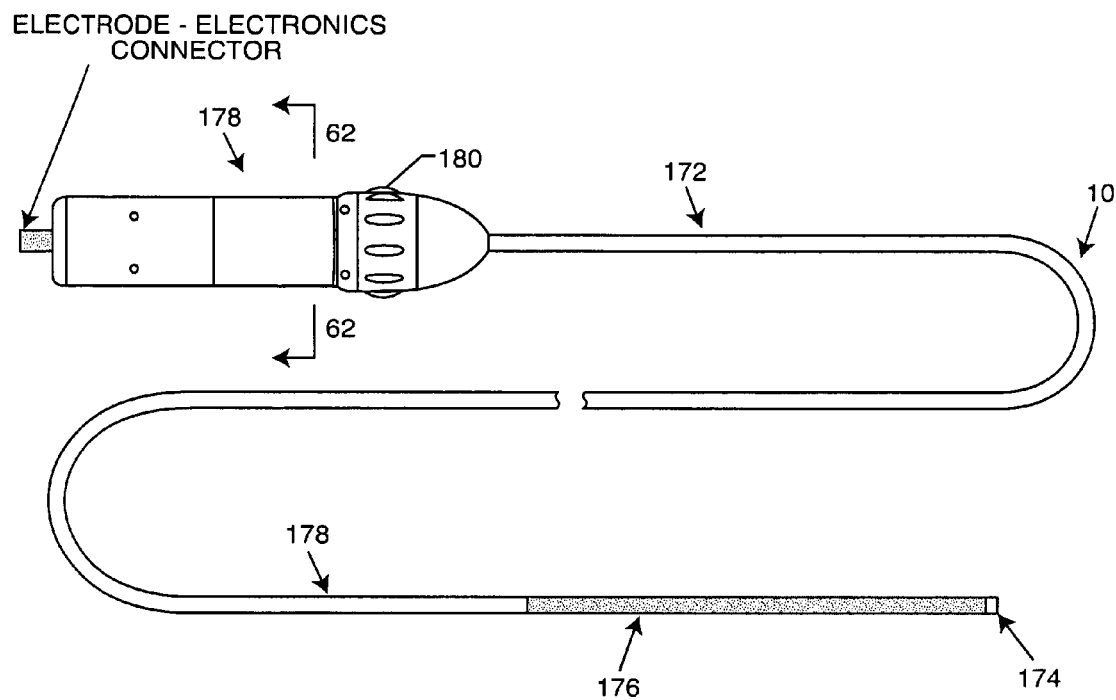
FIG. 61 is an illustration of a steerable catheter.

FIG. 61 shows a steerable catheter 172, which is typically used for a variety of applications including RF or cryo-ablation, cardiac mapping and many other purposes. Examples of RF ablation include treatment for nephrotic conditions, liver, brain, cancers and the like. For example, this would enable stereotactic ablation of certain lesions within the lung. An emerging field is the entire field of using ablation to treat various ventricular arrhythmias, including ventricular tachycardia. The illustrated catheter 172 in FIG. 61 is meant to be representative of all types of catheters or probes which can be inserted into the venous system or other areas of the human body. The catheter 172 has a tip 174 and an adjacent electrode surface 176, and a main catheter body 178, which can be steered around torturous paths. The steerable catheter 172 has a handle 178 which can have various shapes, sizes and configurations in the prior art. By twisting the illustrated cap 180 of the handle 178, one is able to steer the catheter 172 causing its tip 174 or other segments to bend as one guides it.

Figure 62:
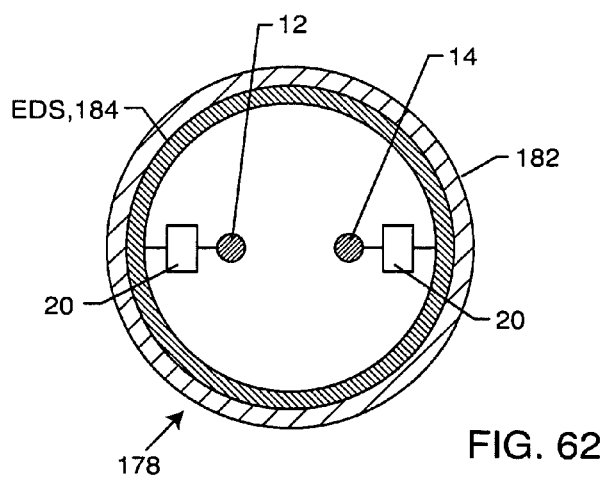
FIG. 62 is an enlarged section view taken generally along the line 62-62 from FIG. 61.

FIG. 62 is an enlarged section taken along line 62-62 in FIG. 61. FIG. 62 illustrates that the handle 178 includes an optional but preferred outer insulation sheath 182 which would typically be of plastic or similar material that would preferably not be highly thermally conductive. Inside of the handle 178 are shown in cross-section leadwires 12 and 14. The illustration of two leadwires is not meant to be limiting since any number of wires could be inside the handle 178 and catheter 172 to sense electrical activity or deliver ablation energy. In accordance with the present invention, there are frequency selective impedance elements 20 shown between the leadwires 12, 14 and an energy dissipating surface EDS, such as a metallic sheath 184. The energy dissipating surface EDS does not necessarily have to be metallic, but it has to be capable of collecting RF energy and conducting thermal energy. This heat energy is therefore dissipated over the large surface area and thermal mass of the handle 178 itself. This results in very little temperature rise, but at the same time, accomplishes the goal of the present invention in redirecting RF energy out of the leadwires 12 and 14 that may be picked up by MRI RF pulsed fields and directing said energy into the relatively large surface area 184 inside the handle 178. Of course, one could eliminate the outer insulation sheath 182. However, in a preferred embodiment, the insulation sheath 182 would be relatively poor in thermal conductivity so that one did really not feel any temperature increase in his or her hand.

Figure 63:
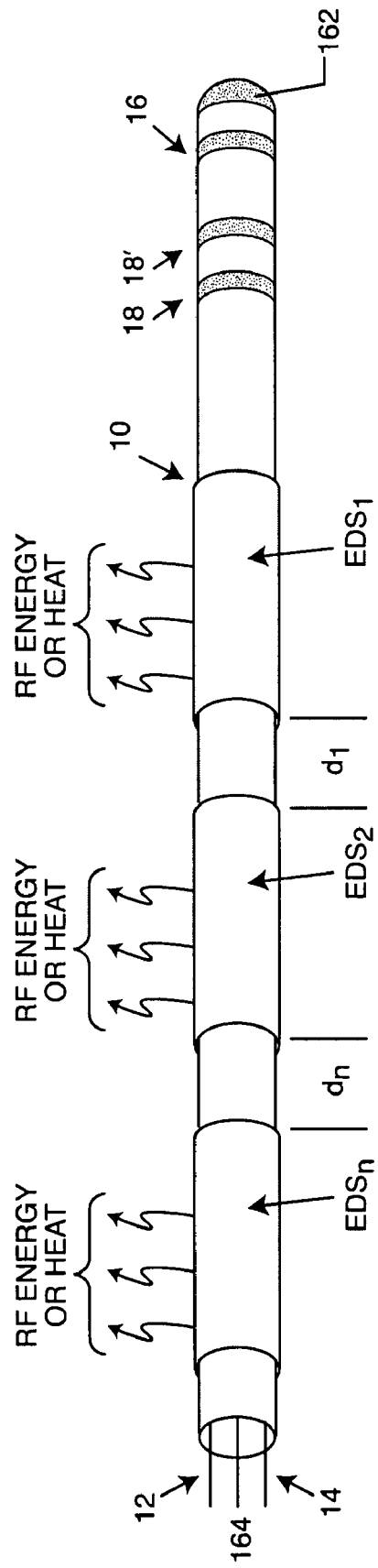
FIG. 63 is a schematic view of a probe or catheter similar to FIG. 55, except that the number of individual energy dissipating surfaces have been provided in distinct and spaced-apart segments.

FIG. 63 is very similar to FIG. 55 except that a number of individual RF energy or heat dissipating segments $EDS_1$, $EDS_2$ and $EDS_n$ are shown. These are shown spaced apart by separation gaps $d_1$ and $d_n$, which in reality can be quite small. The reason that these energy dissipating surfaces are segmented is so that they do not become physically and electrically long enough to become a significant fraction or multiple of a wavelength of the MRI pulsed frequency. Such short conductive sections do not pick up significant energy from MRI whereas elongated leadwires or conductors can, for example, resonate and pick up very significant amounts of MRI RF energy. It would be highly undesirable if the energy dissipating surfaces, as illustrated in FIG. 63, were formed to be continuous along the entire length of the catheter 10 as previously described in connection with FIG. 61. In this case, the energy dissipating surface would actually become an energy collecting surface because it would become a very effective antenna for the MRI pulsed RF signals. Accordingly, breaking this up into discrete segments prevents the EDS surfaces from actually becoming a receiver or antenna for the MRI induced energy.

FIG. 64 illustrates a paddle electrode 186 which could be used, for example, in spinal cord simulator applications. It has eight electrodes 188 housed in a biocompatible insulative and flexible body 190. Eight leadwires 192 are connected respectively to each of the eight electrodes 188. As previously discussed, the elongated leadwires 192 can pick up significant amounts of RF energy during MRI scanning. It is very important that the electrodes 188 do not overheat since they are in direct contact with the body, for example, with the spinal cord.

FIG. 65 illustrates the reverse side of the paddle electrode 186, where an energy dissipating surface EDS is located. As shown in FIG. 66, one can see that the electrodes 188 are conductive pads that contact the spinal nerve route or at least are closely associated with it. The leadwires 192 are each electrically connected to respective electrodes 188. There is a frequency variable impedance (or diverter) element 20 in accordance with the present invention shown between each electrode 188 and the energy dissipating surface EDS. These can individual discreet capacitors or individual discreet L-C traps as shown in FIGS. 5 and 6. These can also be one continuous parasitic capacitance element that formed between the overlap of each of the electrodes and the area of the EDS surface itself. In this case, the insulative dielectric material 194 shown in FIG. 66 would be of relatively high dielectric constant. A high dielectric constant material is desirable so that the amount of parasitic capacitance would be relatively large. By using parasitic capacitance and appropriate dielectric materials, one eliminates the need to use individually installed passive circuit elements. Referring to FIGS. 64-66, one can see that the undesirable RF energy is dissipated on the opposite face of the paddle electrode 186 relative to the electrodes that are in contact with the spinal nerve route. In other words, the RF or thermal energy is dissipated over a relatively large surface area and is directed away from the sensitive juncture between the electrode body tissue contact area. This is important for two reasons, if the RF energy was allowed to concentrate on any one of the electrodes due to resonance phenomenon, then a very high temperature rise could occur which could cause thermal injury to the spinal nerve itself. By redirecting the energy in the opposite direction towards the muscle tissue and over a much larger surface area, much less temperature rise occurs, and even if it does, it is directed into less sensitive tissue.

Figure 67:
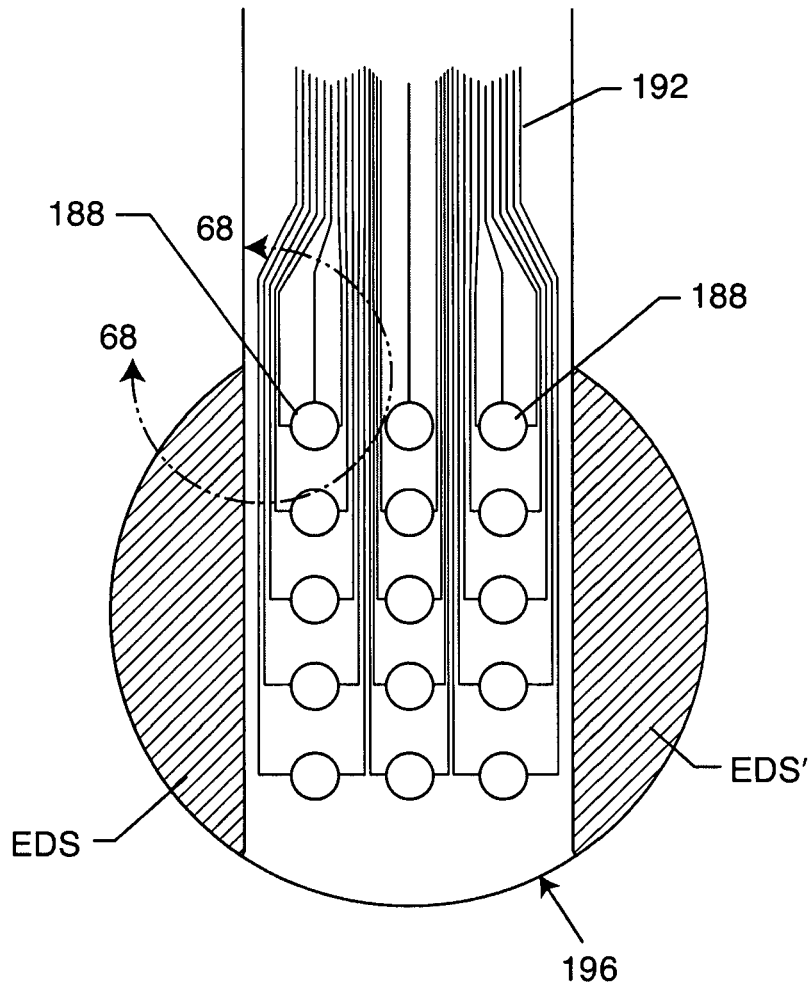
FIG. 67 is a top plan view of a different type of paddle lead structure in comparison with that shown in FIGS. 64-66.
Figure 68:
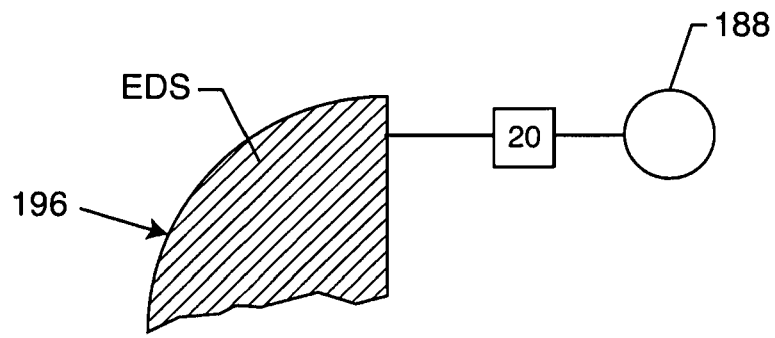
FIG. 68 is an enlarged electrical schematic view taken generally of the area indicated by the line 68-68 in FIG. 67.

FIG. 67 illustrates a different type of paddle lead structure 196 showing a total of fifteen electrodes 188. In this case there are two energy dissipating surfaces EDS and EDS'. For maximum surface area, the energy dissipating surfaces could be on the top surface of the paddle lead structure 196, as well as on the backside or back surface (not shown). In accordance with the present invention, FIG. 68 illustrates a frequency selective variable impedance element 20 which is used to divert RF energy from the electrodes 188 to the EDS surfaces.

Figure 69:
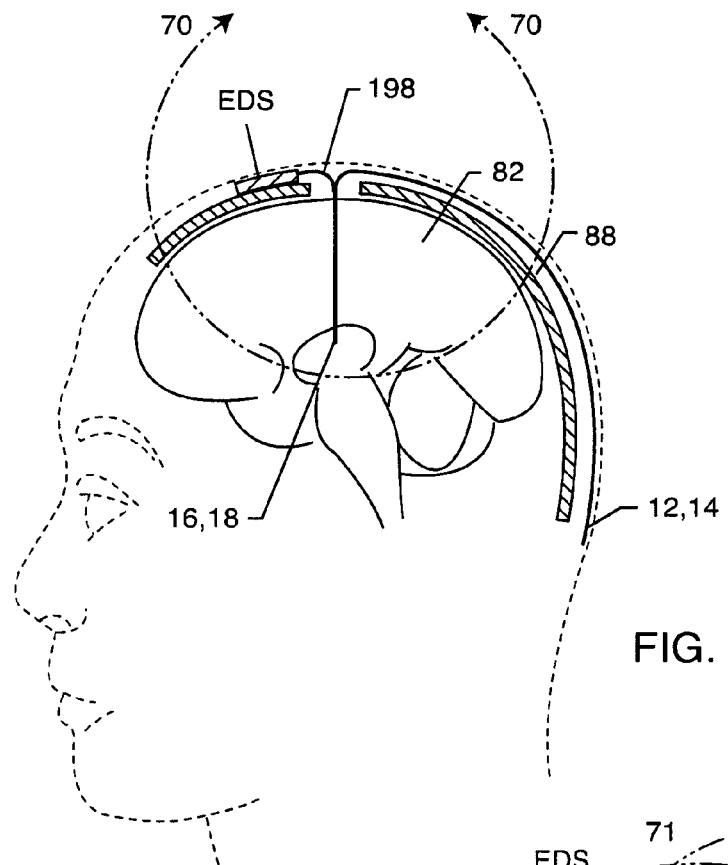
FIG. 69 is a schematic illustration similar to FIG. 28, showing use of a tethered energy dissipating surface in accordance with the present invention.
Figure 70:
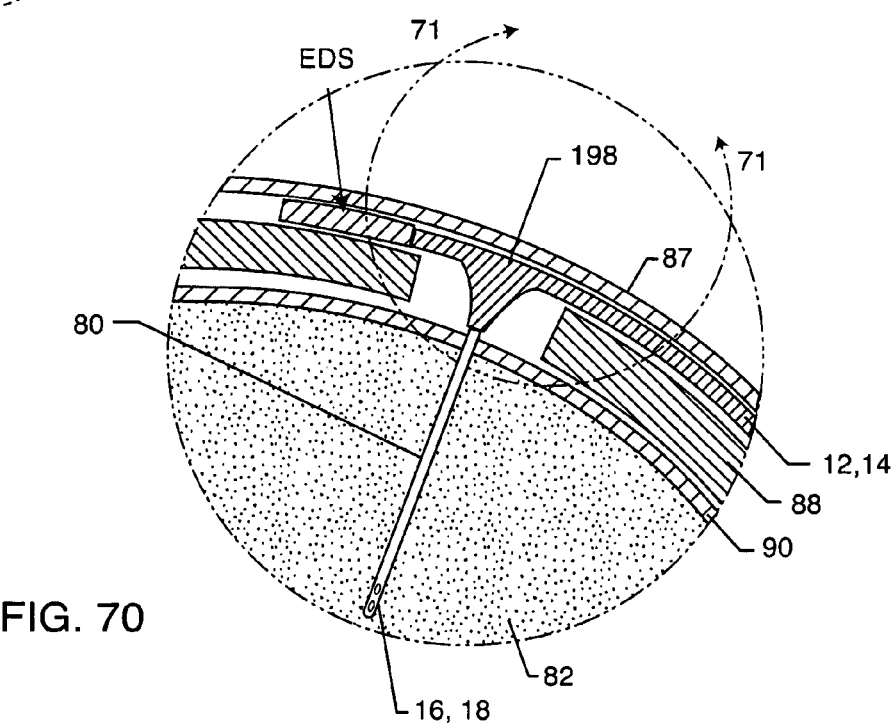
FIG. 70 is an enlarged sectional view of the area indicated by the line 70-70 in FIG. 69.
Figure 71:
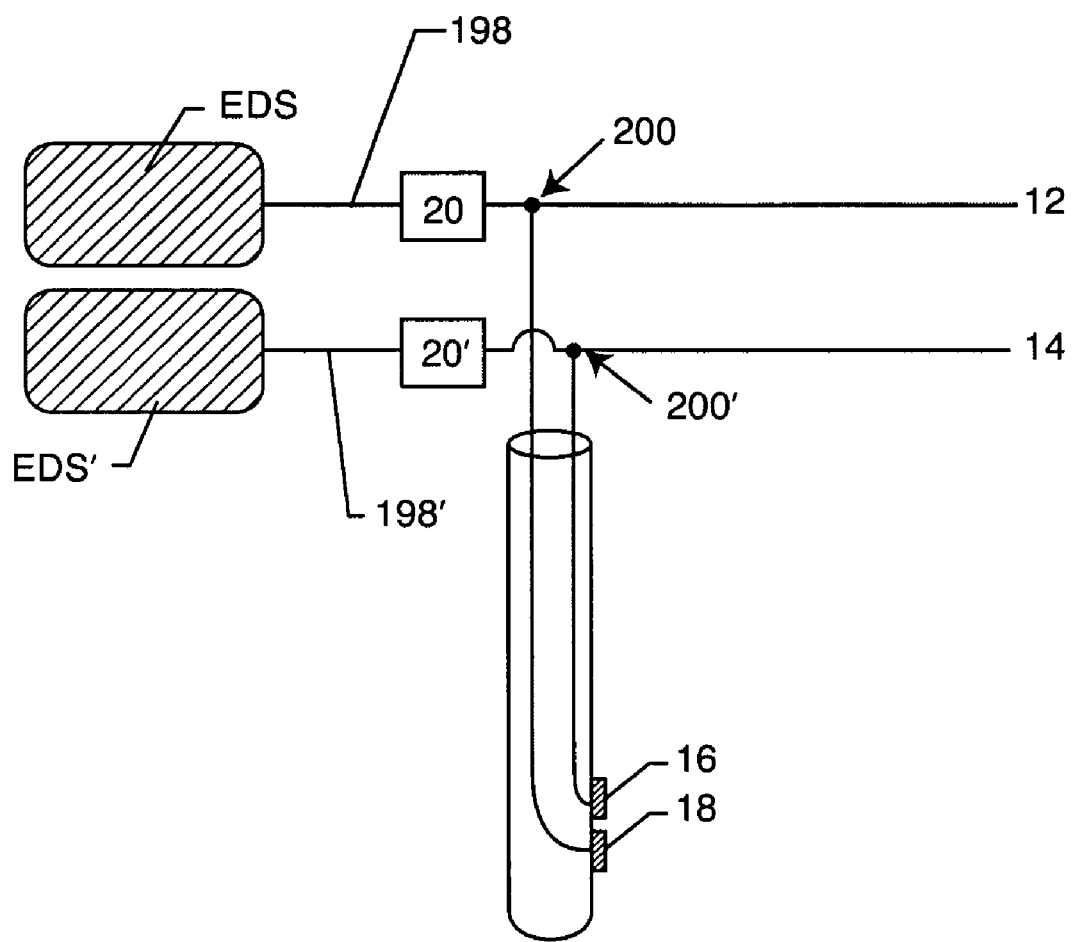
FIG. 71 is an enlarged, somewhat schematic illustration of the components found within the area designated by the line 71-71 in FIG. 70.

FIG. 69 is very similar to FIG. 28 in that it shows a section of human head with a deep brain stimulator disposed therein. There is a plurality of leadwires 12 and 14 which are connected to an AIMD or pulse generator (not shown). The pulse generator would typically be placed in the pectoral region and leadwires 12 and 14 would be routed up along the patient's neck to the deep brain electrodes 16 and 18. Referring to FIGS. 69-71, one can see that there is a novel tether 198 or wire arrangement where the leadwires 12, 14 are not only connected to the distal electrodes 16, 18, but they are also connected to a pair of energy dissipating surfaces of EDS and EDS'. In FIG. 70, one can see the tether area 198 wherein the leadwires 12, 14 connect individually to the electrodes. As shown in FIG. 71, the leadwires 12, 14 have a connection inside the tether area 198 such that the wires are routed both to the distal electrodes 16 and 18 and also through respective junctions 200 and 200' to two individual energy dissipating surfaces (EDS and EDS'). The leadwire 12 has a direct electrical connection at junction 200 to distal electrode 18. In turn, leadwire 14 has a direct connection at junction 200' to distal electrode 16. However, at the junctions 200 and 200', also connected are frequency selective elements 20 which in turn are connected respective energy dissipating pad or surfaces EDS and EDS'. Of course the separate energy dissipating pads could be one large energy dissipating pad. However, in order to maximize surface area and facilitate surgical implantation, two pads are shown. These are originally implanted by the physician underneath a skin flap which is then sewn back down in place. In this way, any heat that is generated during MRI procedures is generated on the top side of the skull well away from any brain matter.

It will be obvious to those skilled in the art that the present invention can be extended to a number of other types of implantable medical devices, including deep brain stimulators, spinal cord stimulators, urinary incontinence stimulators and many other types of devices.

Although several embodiments of the invention have been described in detail, for purposes of illustration, various modifications of each may be made without departing from the spirit and scope of the invention. Accordingly, the invention is not to be limited, except as by the appended claims.

What is claimed is:

1. A passive component network for an implantable leadwire of an active implantable medical device (AIMD), comprising:
   at least one leadwire having a length extending between and to a proximal end and a tissue-stimulating or biological-sensing electrode at a distal tip end; and
   a frequency selective energy diversion circuit for diverting high frequency energy away from the electrode to a point or an area spaced from the electrode for dissipation of said high-frequency energy, wherein the high frequency energy comprises an MRI frequency.

2. The passive component network of claim 1, wherein said MRI frequency comprises a range of MRI frequencies.

3. The passive component network of claim 1, wherein said MRI frequency in megahertz is selected from the group of frequencies comprising 42.56 times strength in Teslas of an MRI scanner.

4. A passive component network for an implantable leadwire of an active implantable medical device (AIMD), comprising:
   at least one leadwire having a length extending between and to a proximal end and a tissue-stimulating or biological-sensing electrode at a distal tip end; and
   a frequency selective energy diversion circuit for diverting high frequency energy away from the electrode to a point or an area spaced from the electrode for dissipation of said high-frequency energy, wherein the frequency selective energy diversion circuit comprises a low pass filter.

5. A passive component network for an implantable leadwire of an active implantable medical device (AIMD), comprising:
   at least one leadwire having a length extending between and to a proximal end and a tissue-stimulating or biological-sensing electrode at a distal tip end; and
   a frequency selective energy diversion circuit for diverting high frequency energy away from the electrode to a point or an area spaced from the electrode for dissipation of said high-frequency energy, wherein the frequency selective energy diversion circuit comprises at least one series resonant LC trap filter.

6. The passive component network of claims 4 or 5, including an energy dissipating surface disposed at a point or an area spaced from the electrode.

7. The passive component network of claim 6, wherein the energy dissipating surface is disposed within the blood flow of a patient.

8. The passive component network of claim 6, wherein the energy dissipating surface comprises a conductive housing.

9. The passive component network of claim 6, wherein the energy dissipating surface comprises a ring electrode.

10. The passive component network of claim 6, wherein the energy dissipating surface comprises convolutions or fins, for increasing the surface area thereof.

11. The passive component network of claim 6, wherein the energy dissipating surface includes a roughened surface.

12. The passive component network of claim 11, wherein the roughened surface is formed through plasma or chemical etching, porous or fractal coatings or surfaces, whiskers, morphologically designed columbar structures, vapor, electron beam or sputter deposition of a high surface area energy conductive material, or a carbon nanotubes.

13. The passive component network of claim 8, wherein said diversion circuit is mounted within said conductive housing.

14. The passive component network of claim 9, wherein said conductive housing protects said diversion circuit from direct contact with patient body fluids.

15. The passive component network of claim 13, wherein said conductive housing is hermetically sealed.

16. The passive component network of claim 6, wherein the energy dissipating surface is disposed within an insulative sheath.

17. The passive component network of claim 6, wherein the energy dissipating surface comprises at least a portion of a handle for a probe or catheter.

18. The passive component network of claim 17, wherein the energy dissipating surface is disposed within an insulative sheath.

19. The passive component network of claim 6, wherein the energy dissipating surface comprises a plurality of spaced-apart energy dissipating surfaces.

20. The passive component network of claim 6, including a tether disposed between and conductively coupling the electrode and the energy dissipating surface.

21. The passive component network of claim 6, wherein the energy dissipating surface comprises a material capable of being visualized during a magnetic resonance scan.

22. The passive component network of claims 4 or 5, further comprising a leadwire housing supporting said leadwire distal tip electrode at one end thereof, said leadwire housing including a conductive housing portion forming an energy dissipating surface, and an insulator housing portion between said leadwire distal tip electrode and said conductive housing portion.

23. The passive component network of claim 22, wherein said distal tip electrode cooperates with said conductive and insulator housing portions to define a hermetically sealed package having said diversion circuit mounted therein.

24. The passive component network of claim 23, wherein said hermetically sealed package has a generally tubular shape with said distal tip electrode mounted at one end thereof, and further defining a hermetic seal assembly at an opposite end thereof, said at least one leadwire extending through said hermetic seal assembly.

25. The passive component network of claim 23, further comprising an impeding circuit associated with said diversion circuit and mounted within said hermetically sealed package.

26. The passive component network of claim 25 wherein said impeding circuit comprises at least one inductor.

27. The passive component network of claim 26 wherein said at least one inductor comprises an inductor chip.

28. The passive component network of claim 23 wherein said diversion circuit comprises at least one capacitor coupled between said leadwire and said energy dissipating surface.

29. The passive component network of claim 26, wherein said at least one inductor comprises a pair of inductor elements, said diversion circuit being coupled between said pair of conductor elements and said energy dissipating surface.

30. The passive component network of claim 29 wherein said diversion circuit comprises at least one capacitor.

31. The passive component network of claims 4 or 5, including an impeding circuit associated with the diversion circuit, for raising the high-frequency impedance of the leadwire, said impeding circuit being disposed between said diversion circuit and the distal tip end of said at least one leadwire.

32. The passive component network of claim 31, wherein the impeding circuit comprises an inductor.

33. The passive component network of claim 31, wherein the impeding circuit comprises a bandstop filter.

34. The passive component network of claims 4 or 5, wherein the at least one leadwire comprises a portion of a probe or a catheter.

35. The passive component network of claim 34, wherein the energy dissipating surface is selected from the group consisting essentially of a sheath, an insulative body, and a thermally conductive element.

36. The passive component network of claims 4 or 5, wherein said at least one leadwire comprises at least a pair of leadwires each having a length extending between and to a proximal end and a tissue-stimulating or biological-sensing electrode at a distal tip end.

37. The passive component network of claim 36, wherein said diversion circuit couples each of said leadwires to an energy dissipating surface disposed at a point or an area distant from each of said electrodes.

38. The passive component network of claim 37, wherein said diversion circuit is also coupled between said pair of leadwires.

39. The passive component network of claim 36, wherein said diversion circuit is coupled between said pair of leadwires.

40. The passive component network of claims 4 or 5, further comprising an energy dissipating surface, and means for hermetically sealed mounting of said energy dissipating surface along said at least one leadwire between said proximal and distal ends thereof, said hermetically sealed means defining a chamber having said diversion circuit mounted therein.

41. The passive component network of claim 40, wherein said at least one leadwire comprises a first leadwire having a tip electrode at a distal end thereof, and a second leadwire having a ring electrode at a distal end thereof, said first and second leadwires having said energy dissipating surface mounted thereon in hermetically sealed relation therewith and extending through said chamber, said diversion circuit coupling said first and second leadwires to said energy dissipating surface.

42. The passive component network of claim 41, wherein said diversion circuit comprises a unipolar or multi-polar feedthrough capacitor.

43. The passive component network of claim 40, further comprising an impeding circuit associated with said diversion circuit and mounted within said hermetically sealed chamber.

44. The passive component network of claims 4 or 5, wherein the active implantable medical device (AIMD) comprises a probe.

45. The passive component network of claim 44, wherein said electrode comprises an ablation tip electrode at or near said leadwire distal end.

46. The passive component network of claim 45, further comprising a probe housing having said ablation tip electrode at or near a distal end thereof, and an energy dissipating surface carried by said probe housing at a point or an area distant from said ablation tip electrode, said diversion circuit diverting high frequency energy away from said ablation tip electrode to said energy dissipating surface.

47. The passive component network of claim 45, wherein said at least one leadwire comprises a first leadwire having said ablation tip electrode at or near a distal end thereof, and at least one second leadwire having a ring electrode at or near a distal end thereof, and an energy dissipating surface carried by said probe housing at a point or an area distant from said ablation tip electrode and said ring electrode, said diversion circuit diverting high frequency energy away from said ablation tip and said ring electrodes to said energy dissipating surface.

48. The passive component network of claim 4, wherein the low pass filter comprises a capacitor, an inductor, a Pi filter, a T filter, an LL filter, or an "n" element filter.

49. The passive component network of claim 5, wherein the frequency selective energy diversion circuit comprises a plurality of LC trap filters resonant respectively at different MRI frequencies.

50. A passive component network for an implantable leadwire of an active implantable medical device (AIMD), comprising:
    at least one leadwire having a length extending between and to a proximal end and a tissue-stimulating or biological-sensing electrode at a distal tip end;
    a frequency selective energy diversion circuit for diverting high frequency energy away from the electrode to a point or an area spaced from the electrode for dissipation of said high-frequency energy; and
    an energy dissipating surface disposed at a point or an area spaced from the electrode;
    wherein the energy dissipating surface comprises a conductive housing;
    wherein said diversion circuit is mounted within said conductive housing; and
    wherein said active implantable medical device (AIMD) comprises a deep brain stimulator.

51. The passive component network of claim 50, wherein said conductive housing is adapted for mounting in thermal communication with a patient's skull.

52. The passive component network of claim 50, further comprising an electrode shaft assembly having a proximal end carried by said conductive housing, said at least one leadwire extending through said electrode shaft assembly and having said distal tip end electrode for contacting patient brain tissue.

53. A passive component network for an implantable leadwire of an active implantable medical device (AIMD), comprising:
    at least one leadwire having a length extending between and to a proximal end and a tissue-stimulating or biological-sensing electrode at a distal tip end;
    a frequency selective energy diversion circuit for diverting high frequency energy away from the electrode to a point or an area spaced from the electrode for dissipation of said high-frequency energy;
    a leadwire housing supporting said leadwire distal tip electrode at one end thereof, said leadwire housing including a conductive housing portion forming an energy dissipating surface, and an insulator housing portion between said leadwire distal tip electrode and said conductive housing portion, wherein said distal tip electrode cooperates with said conductive and insulator housing portions to define a hermetically sealed package having said diversion circuit mounted therein; and
    an impeding circuit associated with said diversion circuit and mounted within said hermetically sealed package;
    wherein said at least one inductor comprises an inductor wire wound onto a ferromagnetic or non-ferromagnetic mandrel.

54. A passive component network for an implantable leadwire of an active implantable medical device (AIMD), comprising:
    at least one leadwire having a length extending between and to a proximal end and a tissue-stimulating or biological-sensing electrode at a distal tip end;
    a frequency selective energy diversion circuit for diverting high frequency energy away from the electrode to a point or an area spaced from the electrode for dissipation of said high-frequency energy; and
    a leadwire housing supporting said leadwire distal tip electrode at one end thereof, said leadwire housing including a conductive housing portion forming an energy dissipating surface, and an insulator housing portion between said leadwire distal tip electrode and said conductive housing portion;
    wherein said distal tip electrode cooperates with said conductive and insulator housing portions to define a hermetically sealed package having said diversion circuit mounted therein; and
    wherein said diversion circuit comprises at least one LC trap filter coupled between said leadwire and said energy dissipating surface.

55. A passive component network for an implantable leadwire of an active implantable medical device (AIMD), comprising:
    at least one leadwire having a length extending between and to a proximal end and a tissue-stimulating or biological-sensing electrode at a distal tip end;
    a frequency selective energy diversion circuit for diverting high frequency energy away from the electrode to a point or an area spaced from the electrode for dissipation of said high-frequency energy;
    a leadwire housing supporting said leadwire distal tip electrode at one end thereof, said leadwire housing including a conductive housing portion forming an energy dissipating surface, and an insulator housing portion between said leadwire distal tip electrode and said conductive housing portion, wherein said distal tip electrode cooperates with said conductive and insulator housing portions to define a hermetically sealed package having said diversion circuit mounted therein; and
    an impeding circuit associated with said diversion circuit and mounted within said hermetically sealed package, wherein said impeding circuit comprises at least one inductor;
    wherein said at least one inductor comprises a pair of inductor elements, said diversion circuit being coupled between said pair of inductor elements and said energy dissipating surface; and
    wherein said diversion circuit comprises a plurality of LC trap filters resonant respectively at different MRI frequencies.

56. A passive component network for an implantable leadwire of an active implantable medical device (AIMD), comprising:
    at least one leadwire having a length extending between and to a proximal end and a tissue-stimulating or biological-sensing electrode at a distal tip end;
    a frequency selective energy diversion circuit for diverting high frequency energy away from the electrode to a point or an area spaced from the electrode for dissipation of said high-frequency energy; and an energy dissipating surface disposed at a point or an area spaced from the electrode;

wherein the electrode comprises a paddle electrode disposed on one side of a paddle.

57. The passive component network of claim 56, wherein the energy dissipating surface is disposed on a second side of the paddle.

58. The passive component network of claim 57, where the frequency selective diversion circuit comprises a capacitive element disposed within the paddle between the electrode and the energy dissipating surface.

59. The passive component network of claim 58, wherein the capacitive element comprises a discrete capacitor.

60. The passive component network of claim 58, wherein the capacitive element comprises parasitic capacitance.

61. The passive component network of claim 56, wherein the energy dissipating surface is attached to the paddle.

* * * * *

UNITED STATES PATENT AND TRADEMARK OFFICE
CERTIFICATE OF CORRECTION

PATENT NO.       : 7,751,903 B2                        Page 1 of 1
APPLICATION NO.  : 12/489921
DATED            : July 6, 2010
INVENTOR(S)      : Robert A Stevenson et al.

It is certified that error appears in the above-identified patent and that said Letters Patent is hereby corrected as shown below:

On the Title page, Item [60] under the "Related U.S. Application Data" should read -- Provisional application No. 61/074,816, filed on June 23, 2008. --.

Signed and Sealed this
Third Day of July, 2012

David J. Kappos
*Director of the United States Patent and Trademark Office*